US012622973B2

(12) United States Patent
Low et al.

(10) Patent No.: US 12,622,973 B2
(45) Date of Patent: May 12, 2026

(54) REJUVENATION OF CAR T CELL

(71) Applicant: Purdue Research Foundation, West Lafayette, IN (US)

(72) Inventors: Philip Stewart Low, West Lafayette, IN (US); Boning Zhang, West Lafayette, IN (US); John V. Napoleon, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 18/392,939

(22) Filed: Dec. 21, 2023

(65) Prior Publication Data

US 2024/0148880 A1 May 9, 2024

Related U.S. Application Data

(63) Continuation of application No. 17/266,509, filed as application No. PCT/US2019/042726 on Jul. 21, 2019, now abandoned.

(60) Provisional application No. 62/715,666, filed on Aug. 7, 2018.

(51) Int. Cl.

| | |
|---|---|
| ***A61K 47/55*** | (2017.01) |
| ***A61K 31/437*** | (2006.01) |
| ***A61K 31/4535*** | (2006.01) |
| ***A61K 31/4545*** | (2006.01) |
| ***A61K 31/7076*** | (2006.01) |
| ***A61K 40/11*** | (2025.01) |
| ***A61K 40/31*** | (2025.01) |
| ***A61K 40/42*** | (2025.01) |
| ***A61K 47/62*** | (2017.01) |
| ***A61K 47/68*** | (2017.01) |
| ***A61K 49/00*** | (2006.01) |

(52) U.S. Cl.

CPC ............ *A61K 47/55* (2017.08); *A61K 31/437* (2013.01); *A61K 31/4535* (2013.01); *A61K 31/4545* (2013.01); *A61K 31/7076* (2013.01); *A61K 40/11* (2025.01); *A61K 40/31* (2025.01); *A61K 40/4211* (2025.01); *A61K 47/62* (2017.08); *A61K 47/6835* (2017.08); *A61K 49/0043* (2013.01); *A61K 49/0052* (2013.01); *A61K 2239/48* (2023.05)

(58) Field of Classification Search

CPC ........ A61K 47/55; A61K 47/62; A61K 47/64; A61K 47/6835

See application file for complete search history.

(56) References Cited

U.S. PATENT DOCUMENTS

| | | | |
|---|---|---|---|
| 12,343,403 | B2 | 7/2025 | Low et al. |
| 2003/0185840 | A1 | 10/2003 | Ioannides et al. |
| 2007/0077197 | A1 | 4/2007 | Wedeking et al. |
| 2008/0260812 | A1 | 10/2008 | Matsuyama et al. |
| 2012/0076728 | A1 | 3/2012 | Wu et al. |
| 2017/0073423 | A1 | 3/2017 | Cellectis |
| 2021/0308267 | A1 | 10/2021 | Low et al. |
| 2025/0262313 | A1 | 8/2025 | Low et al. |

FOREIGN PATENT DOCUMENTS

| | | | |
|---|---|---|---|
| AU | 2019317278 | | 9/2025 |
| CN | 105814083 | A | 7/2016 |
| CN | 105829349 | A | 8/2016 |
| CN | 106163547 | A | 11/2016 |
| CN | 106459924 | | 2/2017 |
| CN | 112543651 | A | 3/2021 |
| CN | 112543651 | B | 6/2023 |
| CN | 116763943 | A | 9/2023 |
| EP | 3833400 | | 6/2022 |
| HK | 40049545 | | 12/2023 |
| IN | 202117002059 | A | 3/2021 |
| IN | 421235 | | 2/2023 |
| JP | 2021533166 | A | 12/2021 |
| JP | 7623935 | | 1/2025 |
| WO | 2011079227 | | 6/2011 |
| WO | 2014100615 | | 6/2014 |
| WO | WO-2015057834 | A1 | 4/2015 |
| WO | WO-2015057852 | A1 | 4/2015 |
| WO | 2015164594 | | 10/2015 |
| WO | 2016098078 | | 6/2016 |
| WO | 2016164745 | | 10/2016 |
| WO | WO-2017035117 | A1 | 3/2017 |
| WO | WO-2017177137 | A1 | 10/2017 |
| WO | WO-2017177149 | A2 | 10/2017 |
| WO | WO-2017205661 | A1 | 11/2017 |
| WO | WO-2018111989 | A1 | 6/2018 |
| WO | WO-2018152451 | A1 | 8/2018 |
| WO | 2018160622 | | 9/2018 |
| WO | 2019144091 | | 7/2019 |
| WO | 2019144095 | | 7/2019 |
| WO | 2019165237 | | 8/2019 |
| WO | WO-2020033129 | A1 | 2/2020 |
| WO | 2021178887 | | 9/2021 |
| WO | 2024086563 | | 4/2024 |

OTHER PUBLICATIONS

"U.S. Appl. No. 17/266,509, Non Final Office Action mailed Jul. 19, 2023", 12 pgs.

(Continued)

*Primary Examiner* — James W Rogers

(74) *Attorney, Agent, or Firm* — Schwegman Lundberg & Woessner, P.A.

(57) ABSTRACT

A payload of drug conjugated to a targeting ligand specifically designed to deliver to exhausted CAR T cells to rejuvenate these CAR T cells is provided herein. The targeted CAR T cells are modified with a fusion receptor which can bind to the targeting ligand and internalize the conjugated payload of drug to execute its regulatory function to exhausted CAR T cell.

18 Claims, 15 Drawing Sheets

(56) References Cited

OTHER PUBLICATIONS

"U.S. Appl. No. 17/266,509, Response filed Apr. 19, 2023 to Restriction Requirement mailed Mar. 14, 2023", 13 pgs.
"U.S. Appl. No. 17/266,509, Response filed Nov. 14, 2023 to Non Final Office Action mailed Jul. 19, 2023", 15 pgs.
"U.S. Appl. No. 17/266,509, Restriction Requirement mailed Mar. 14, 2023", 9 pgs.
"Chinese Application Serial No. 201980052586.7, Notice of Preliminary Examination mailed Mar. 1, 2021", (w/ English Translation), 2 pgs.
"Chinese Application Serial No. 201980052586.7, Office Action mailed Aug. 8, 2022", (w/ English Translation), 16 pgs.
"Chinese Application Serial No. 201980052586.7, Response filed Dec. 23, 2022 to Office Action mailed Aug. 8, 2022", w/ English claims, 22 pgs.
"Chinese Application Serial No. 201980052586.7, Response to Examiner Telephone Interview filed Feb. 14, 2023", w/ English claims, 15 pgs.
"Chinese Application Serial No. 202310525133.X, Notification to Make Rectification mailed Jul. 21, 2023", w/ machine English Translation, 2 pgs.
"Chinese Application Serial No. 202310525133.X, Response filed Aug. 16, 2023 to Notification to Make Rectification mailed Jul. 21, 2023", w/ English claims, 42 pgs.
"Chinese Application Serial No. 202310525133.X, Voluntary Amendment filed Nov. 30, 2023".
"European Application Serial No. 19847190.6 Response filed May 6, 2021 to Office Action Mailed May 4, 2021", 21 pgs.
"European Application Serial No. 19847190.6, Extended European Search Report mailed May 12, 2022", 12 pgs.
"European Application Serial No. 19847190.6, Response filed Mar. 29, 2021 to Communication pursuant to Rules 161(2) and 162 EPC mailed Mar. 16, 2021", 18 pgs.
"European Application Serial No. 19847190.6, Response filed Nov. 30, 2022 to Extended European Search Report mailed May 12, 2022", 6 pgs.
"Indian Application Serial No. 202117002059, First Examination Report mailed Aug. 204, 22", 7 pgs.
"Indian Application Serial No. 202117002059, Response filed Feb. 2, 2023 to First Examination Report mailed Aug. 4, 2022", 76 pgs.
"International Application Serial No. PCT/US2019/042726, International Preliminary Report on Patentability mailed Feb. 18, 2021", 6 pgs.
"International Application Serial No. PCT/US2019/042726, International Search Report mailed Oct. 4, 2019", 2 pgs.
"International Application Serial No. PCT/US2019/042726, Written Opinion mailed Oct. 4, 2019", 2 pgs.
"Japanese Application Serial No. 2021-506492, Notification of Reasons for Rejection mailed Aug. 7, 2023", W/English Translation, 8 pgs.
"Japanese Application Serial No. 2021-506492, Voluntary Amendment filed Jul. 20, 2022", w/English claims, 26 pgs.
"Korean Application Serial No. 10-2021-7006445, Voluntary Amendment filed Jul. 21, 2022", w/English claims, 63 pgs.
"Singaporean Application Serial No. 11202100616V, Voluntary Amendment filed Feb. 3, 2023", w/ English claims, 25 pgs.
Alfei, Francesca, et al., "TOX reinforces the phenotype and longevity of exhausted T cells in chronic viral infection", Nature, 571, (2019), 265-269.
Bandara, N. Achini, et al., "Effect of receptor occupancy on folate receptor internalization", Molecular Pharmaceutics, 11(3), (2014), 1007-1013.
Bhattacharyya, Sibaprasad, et al., "Metallic radionuclides in the development of diagnostic and therapeutic radiopharmaceuticals", Dalton Transactions, 40(23), (2011), 6112-6128.
Bruno, R., et al., "Sodium iodide symporter expression and radio iodine distribution in extrathyroidal tissues", J Endocrinol Invest., 27(11), (2004), 1010-1014.
Caron, Gersende, et al., "Direct stimulation of human T cells via TLR5 and TLR7/8: flagellin and R-848 up-regulate proliferation and IFN-gamma production by memory CD4+ T cells", Journal of Immunology, 175(3), (2005), 1551-1557.
Chae, Y. K., et al., "Current landscape and future of dual anti-CTLA4 and PD-1/PD-L1 blockade immunotherapy in cancer; lessons learned from clinical trials with melanoma and non-small cell lung cancer (NSCLC)", J Immunother Cancer, 6(1), (2018), 39.
Cheadle, E. J., et al., "A TLR7 agonist enhances the antitumor efficacy of obinutuzumab in murine lymphoma models via NK cells and CD4 T cells.", Leukemia, 31(10), (2017), 1611-1621.
Chen, Joyce, et al., "NR4A transcription factors limit CAR T cell function in solid tumours", Nature, 567 (7749), (2019), 530-534.
Chong, Elise A, et al., "Phase I/II Study of Pembrolizumab for Progressive Diffuse Large B Cell Lymphoma after Anti-CD19 Directed Chimeric Antigen Receptor Modified T Cell Therapy", Blood, vol. 130 (Supplement 1): 4121, (Dec. 8, 2017), 4 pages.
Chua, Brendon Y., et al., "The use of a TLR2 agonist-based adjuvant for enhancing effector and memory CD8 T-cell responses", Immunology and Cell Biology, 92(4), (2014), 377-383.
Dobrenkov, Konstantin, et al., "Monitoring the efficacy of adoptively transferred prostate cancer-targeted human T lymphocytes with PET and bioluminescence imaging", Journal of Nuclear Medicine, 49(7), (2008), 1162-1170.
Dotti, Gianpietro, et al., "Design and development of therapies using chimeric antigen receptor-expressing T cells", Immunol. Rev., vol. 257, No. 1, (Dec. 13, 2013), 107-126.
Dudek, Arkadiusz Z., et al., "First in human phase I trial of 852A, a novel systemic toll-like receptor 7 agonist, to activate innate immune responses in patients with advanced cancer", Clinical Cancer Research, 13(23), (2007), 7119-7125.
Dummer, Reinhard, et al., "An Exploratory Study of Systemic Administration of the Toll-like Receptor-7 Agonist 852A in Patients with Refractory Metastatic Melanoma", Clinical Cancer Research, 14(3), (2008), 856-864.
Emami-Shahri, Nia, et al., "Clinically compliant spatial and temporal imaging of chimeric antigen receptor T-cells", Nature Communications, 9(1), Article No. 1081, (2018), 1-12.
Ghoneim, Hazem E., et al., "Cell-Intrinsic Barriers of T Cell-Based Immunotherapy", Trends in Molecular Medicine, vol. 22, No. 12, (Dec. 2016), 1000-1011.
Gorelik, Leonid, et al., "Immune-mediated eradication of tumors through the blockade of transforming growth factor-P signaling in T cells", Nature Medicine, 7(10), (2001), 1118-1122.
Harrison, Lester, et al., "Pharmacokinetics of 852A, an Imidazoquinoline Toll-Like Receptor 7-Specific Agonist, Following Intravenous, Subcutaneous, and Oral Administrations in Humans", Journal of Clinical Pharmacology, 47(8), (2007), 962-969.
Hasham, M., et al., "Systemic autoimmunity induced by the TFR7/8 agonist Resiquimod causes myocarditis and dilated cardiomyopathy in a new mouse model of autoimmune heart disease", Dis Model Mech., 10(3), (2017), 259-270, (2017), 22 pages.
Hebeisen, Michael, et al., "SHP-1 phosphatase activity counteracts increased T cell receptor affinity", The Journal of Clinical Investigation, 123(3), (2013), 1044-1056.
Hemmi, Hiroaki, et al., "Small anti-viral compounds activate immune cells via the TLR7 MyD88-dependent signaling pathway", Nature Immunology, 3(2), (2002), 196-200.
Hengge, Ulrich R., et al., "Topical immunomodulation in dermatology: potential of toll-like receptor agonists", Dermatol Surg, 30(8), (2004), 1101-1112.
Henne, Walter A., et al., "Imaging sites of infection using a 99mTc-labeled folate conjugate targeted to folate receptor positive macrophages", Molecular Pharmaceutics, 9(5), (2012), 1435-1440.
Herbertz, Stephen, et al., "Clinical development of galunisertib (LY2157299 monohydrate), a small molecule inhibitor of transforming growth factor-beta signaling pathway", Drug Design, Development and Therapy, 9, (2015), 4479-4499.
Hornung, Veit, et al., "Quantitative expression of toll-like receptor 1-10 mRNA in cellular subsets of human peripheral blood mononuclear cells and sensitivity to CpG oligodeoxynucleotides", Journal of Immunology, 168(9), (2002), 4531-4537.

(56) References Cited

OTHER PUBLICATIONS

Ignacio, Bob J., et al., "Toll-like Receptor Agonist Conjugation: A Chemical Perspective", Bioconjugate Chemistry, 29(3), (2016), 587-603.
Iversen, Lars F., et al., "Structure Determination of T Cell Protein-tyrosine Phosphatase", The Journal of Biological Chemistry, 277(22), (2002), 19982-19990.
Jiang, Y., et al., "T-cell exhaustion in the tumor microenvironment", Cell Death Dis., 6, e1792, (2015), 1-9.
Jin, Cheng H., et al., "Discovery of N-((4-([1,2,4]Triazolo[1,5-a]pyridin-6-yl)-5-(6-methylpyridin-2-yl)-1H-imidazol-2-yl)methyl)-2-fluoroaniline (EW-7197): A Highly Potent, Selective, and Orally Bioavailable Inhibitor of TGF-ß Type I Receptor", Kinase as Cancer Immunotherapeutic/Antifibrotic Agent, Journal of Medicinal Chemistry, 57(10), (2014), 4213-4238.
Jones, Peter, et al., "Discovery of a highly potent series of TLR7 agonists", Bioorganic & Medicinal Chemistry Letters, 21(19), (2011), 5939-5943.
Kaczanowska, Sabina, et al., "TLR agonists: our best frenemy in cancer immunotherapy", Journal of leukocyte Biology, 93(6), (2013), 847-863.
Kahan, Shannon M., et al., "T cell exhaustion during persistent viral infections", Virology, 479-480, (2015), 180-193.
Kawai, Taro, et al., "Signaling to NF-kappaB by Toll-like receptors", Trends in Molecular Medicine, 13(11), (2007), 460-469.
Khan, Omar, et al., "TOX transcriptionally and epigenetically programs CD8(+) T cell exhaustion", Nature, 571(7764), (2019), 211-218.
Kim, Min Soo, et al., "Redirection of Genetically Engineered CAR-T Cells Using Bifunctional Small Molecules", Journal of the American Chemical Society, vol. 137, No. 8, (Feb. 18, 2015), 2832-2835.
Kniess, Torsten, et al., "Technetium-99m based small molecule radiopharmaceuticals and radiotracers targeting inflammation and infection", Dalton Transactions, 46(42), (2017), 14435-14451.
Knochelmann, H. M., et al., "CAR T Cells in Solid Tumors: Blueprints for Building effective Therapies", Frontiers in Immunology vol. 9: Article1490, (2018), 1-20.
Kularatne, S. A., et al., "Design, Synthesis, and Preclinical Evaluation of Prostate-Specific Membrane Antigen Targeted 99mTc-Radioimaging Agents", Molecular Pharmaceuticals, 6(3), (2009), 790-800.
Larkin, Bridget, et al., "Cutting Edge: Activation of STING in T Cells Induces Type IIFN Responses and Cell Death", Journal of Immunology, 199(2), (2017), 397-402.
Li, Ping, et al., "Clinical Application of Chimeric Antigen Receptor T Cells in the Treatment of Hematological Malignancies", (w/ English Abstract), Journal of Internal Intensive Medicine, vol. 22, No. 2, (Dec. 31, 2016), 91-93.
Lorenz, Ulrike, et al., "SHP-1 and SHP-2 in T cells: two phosphatases functioning at many levels", Immunological Reviews 228(1), (2009), 342-359.
Mackall, Crystal L., et al., "Enhancing the Efficacy of CAR T Cells", Blood Journal, vol. 130 (Supplement 1): SCI-15, (2017), 2 pages.
Mackall, Crystal L., "Enhancing the Efficacy of CART Cells", Blood, vol. 130 (Suppl. 1): SCI-15, (2017), 2 pages.
Matsuzaki, Junko, et al., "Tumor-infiltrating NY-ESO-1-specific CD8+ T cells are negatively regulated by LAG-3 and PD-1 in human ovarian cancer", Proc. Natl. Acad. of Sci. USA, 107(17), (2010), 7875-7880.
Moon, Edmund K., et al., "Blockade of Programmed Death 1 Augments the Ability of Human T Cells Engineered to Target NY-ESO-1 to Control Tumor Growth after Adoptive Transfer", Clinical Cancer Research, 22(2), (2016), 436-437.
Moon, Edmund K., et al., "Multifactorial T-cell hypofunction that is reversible can limit the efficacy of chimeric antigen receptor-transduced human T cells in solid tumors", Clinical Cancer Research, 20(16), (2014), 4262-4273.
Napoleon, John Victor, et al., "Design, Synthesis, and Targeted Delivery of an Immune Stimulant that Selectively Reactivates Exhausted CAR T Cell", Angew. Chem. Int. Ed, vol. 61, (Jan. 27, 2022), 1-8.
Ott, Patrick A., et al., "Combination immunotherapy: a road map", J Immunother Cancer, 5, Article No. 16, (2017), 15 pages.
Parente-Pereira, Ana C., et al., "Trafficking of CAR-engineered human T cells following regional or systemic adoptive transfer in SCID beige mice", J Clin Immunol., 31(4), (2011), 710-718.
Park, Jae H., et al., "Long-Term Follow-up of CD19 CAR Therapy in Acute Lymphoblastic Leukemia", N. Engl. J. of Med., 378, (2018), 449-459.
Perkins, Hannah, et al., "Therapy with TFR7 agonists induces lymphopenia: correlating pharmacology to mechanism in a mouse model", J Clin Immunol., 32(5), (2012), 1082-1092.
Pike, K. A., et al., "TC-PTP regulates the IL-7 transcriptional response during murine early T cell development", Scientific Reports, 7(1): 13275, (2017), 1-12.
Poh, Alissa, et al., "Engineering CAR T Cells with Biomaterials", Cancer Discovery, vol. 7, No. 7, (Jul. 2017), 656-657.
Prinz, Petra U., et al., "High DGK-alpha and disabled MAPK pathways cause dysfunction of human tumor-infiltrating CD8+ T cells that is reversible by pharmacologic intervention", Journal of Immunology, 188(12), (2012), 5990-6000.
Pryde, David C., et al., "The discovery of a novel prototype small molecule TFR7 agonist for the treatment of hepatitis C virus infection", MedChemComm, 2(3), (2011), 185-189.
Rhee, Elizbeth G., et al., "TLR4 ligands augment antigen-specific CD8+ T lymphocyte responses elicited by a viral vaccine vector", Journal of Virology, 84(19), (2010), 10413-10419.
Smith, Tyrel T., et al., "Biopolymers codelivering engineered T cells and STING agonists can eliminate heterogeneous tumors", The Journal of Clinical Investigation, vol. 127, No. 6, (Jun. 2017), 2176-2191.
Stefanova, Irema, et al., "TCR ligand discrimination is enforced by competing ERK positive and SHP-1 negative feedback pathways", Nature Immunology, 4(3), (2003), 248-254.
Strominger, N. L., et al., "Imiquimod-elicited emesis is mediated by the area postrema, but not by direct neuronal activation", Brain Res Bull., 55(3), (2001), 445-451.
Tang, C. A., et al., "Targeting endoplasmic reticulum-resident proteins for the treatment of B cell cancer", Abstract M138, Cell Biology 2016, ASCB Annual Meeting, San Francisco, CA (Dec. 3-7, 2016), (2016), 2 pages.
Vedvyas, Yogindra, et al., "Longitudinal PET imaging demonstrates biphasic CAR T cell responses in survivors", JCI insight, 1(19), e90064, (2016), 1-17.
Wang, David, et al., "Targeting EZH2 Reprograms Intratumoral Regulatory T Cells to Enhance Cancer Immunity", Cell Reports, 23(11), (2018), p. 3262-3274.
Watson, H. Angharad, et al., "Purity of transferred CD8(+) T cells is crucial for safety and efficacy of combinatorial tumor immunotherapy in the absence of SHP-1", Immunology and Cell Biology, 94(8), (2016), 802-808.
Watson, H. Angharad, et al., "SHP-1: the next checkpoint target for cancer immunotherapy?", Biochemical Society Transactions, 44(2), (2016), 356-362.
Wiede, Florian, et al., "T cell protein tyrosine phosphatase attenuates T cell signaling to maintain tolerance in mice", The Journal of Clinical Investigation, 121(12), (2011), 4758-4774.
Wiedemann, Gabriela M., et al., "A novel TLR7 agonist reverses NK cell anergy and cures RMA-S lymphoma-bearing mice", Oncoimmunology, 5(7), ell89051, (2016), 11 pages.
Wille-Reece, Ulrike, et al., "Toll-like receptor agonists influence the magnitude and quality of memory T cell responses after prime-boost immunization in nonhuman primates", The Journal of Experimental Medicine, 203(5), (2006), 1249-1258.
Wilson, Douglas P., et al., "Structure-based optimization of protein tyrosine phosphatase IB inhibitors: from the active site to the second phosphotyrosine binding site", Journal of Medicinal Chemistry, 50(19), (2007), 4681-4698.
Zarember, Kol A., et al., "Tissue expression of human Toll-like receptors and differential regulation of Toll-like receptor mRNAs in

(56) References Cited

OTHER PUBLICATIONS leukocytes in response to microbes, their products, and cytokines", Journal of Immunology, 168(2), (2002), 554-561.
Zhang, Hanwen, et al., "Imaging Expression of the Human Somatostatin Receptor Subtype-2 Reporter Gene with 68Ga-DOTATOC", Journal of Nuclear Medicine, 52(1), (2011), 123-131.
"Canadian Application Serial No. 3,108,710, Voluntary Amendment Filed Jul. 19, 2024", 22 pgs.
"New Zealand Application Serial No. 772992, Voluntary Amendment filed Jul. 19, 2024", 70 pgs.
"Korean Application Serial No. 10-2021-7006445, Notice of Preliminary Rejection mailed Aug. 30, 2024", w English translation, 10 pgs.
"Japanese Application Serial No. 2021-506492, Response filed Sep. 27, 2024 to Notification of Reasons for Refusal mailed Apr. 1, 2024", w English claims, 26 pgs.
"Australian Application Serial No. 2019317278, Response filed Nov. 11, 2024 to First Examination Report mailed May 28, 2024", 19 pgs.
"Australian Application Serial No. 2019317278, Subsequent Examination Report mailed Nov. 20, 2024", 2 pgs.
"Korean Application Serial No. 10-2021-7006445, Response filed Nov. 26, 2024 to Notice of Preliminary Rejection mailed Aug. 30, 2024", w English claims, 38 pgs.
"Japanese Application Serial No. 2021-506492, Response filed Dec. 13, 2023 to Notification of Reasons for Rejection mailed Aug. 7, 2023", w current English claims, 33 pgs.
"U.S. Appl. No. 17/266,509, Final Office Action mailed Dec. 26, 2023", 8 pgs.
"Japanese Application Serial No. 2021-506492, Notification of Reasons for Refusal mailed Apr. 1, 2024", w English translation, 8 pgs.
"Australian Application Serial No. 2019317278, First Examination Report mailed May 28, 2024", 4 pgs.
"Australian Application Serial No. 2019317278, Response filed May 1, 2025 to Subsequent Examination Report mailed Nov. 20, 2024", 3 pgs.
"Chinese Application Serial No. 202310525133.X, Office Action mailed Jun. 17, 2025", w English translation, 14 pgs.
"Korean Application Serial No. 10-2021-7006445, Final Office Action mailed Jun. 25, 2025", w English translation, 9 pgs.
"Canadian Application Serial No. 3,108,710, Examiners Rule 862 Report mailed Jul. 17, 2025", 6 pgs.
"Chinese Application Serial No. 202310525133.X, Response filed Oct. 16, 2025 to Office Action mailed Jun. 17, 2025", w English claims, 29 pgs.
Doucette, Michele M, "Point Mutations Alter the Cellular Distribution of the Human Folate Receptor in Cultured Chinese Hamster Ovary Cells", J. Nutr. 134, 2004, 9 pgs.
James, John R, "Biophysical mechanism of T-cell receptor triggering in a reconstituted system", HHMI Author Manuscript, published as Nature, vol. 487, No. 7405, 64-69, Jul. 5, 2012, 18 pgs.
Nam, Hyun-Joo, "Structural basis for the function and regulation of the receptor protein tyrosine phosphatase CD45", JEM, The Rockefeller University Press, vol. 201, No. 3, Feb. 7, 2005 441-452., Feb. 7, 2005, 12 pgs.
Porter, D.L., "Chimeric antigen receptor-modified T cells in chronic lymphoid leukemia", The New England Journal of Medicine 365, Aug. 25, 2011, 725-733.
Shillingford, Jonathan M., "Folate-Conjugated Rapamycin Slows Progression of Polycystic Kidney Disease", J. Am Soc Nephrol, vol. 23, No. 10, Sep. 28, 2012, 1674-1681.
Suen, WL, "Size-Dependent Internalisation of Folate-Decorated Nanoparticles via the Pathways of Clathrin and Caveolae-Mediated Endocytosis in ARPE-19 Cells", J. Pharm. Pharmacol. 2014, 66, 564-573., 2014, 10 pgs.
Wilbowo, "Structures of human folate receptors reveal biological trafficking states and diversity in folate and antifolate recognition", PNAS, 2013, 15180-15188.
Xia, Wei, "Folate-Targeted Therapies for Cancer", Journal of Medicinal Chemistry, 5319, Oct. 14, 2010, 14 pgs.
Zhang, Boning, "Sensitive manipulation of CAR T cell activity using a chimeric endocytosing receptor", Journal for Immuno Therapy of Cancer, 2020, 12 pgs.
Zhou, Xiaoou, "Improving the safety of T-Cell therapies using an inducible caspase-9 gene", Experimental Hematology, Elsevier Inc, US, vol. 44, No. 11, Jul. 26, 2016, 1013-1019.
"Canadian Application Serial No. 3,108,710, Response filed Nov. 17, 2025 to Examiners Rule 86(2) Report mailed Jul. 17, 2025", 35 pgs.
"European Application Serial No. 19847190.6, Communication Pursuant to Article 94(3) EPC mailed Dec. 22, 2025", 4 pgs.
"Singaporean Application Serial No. 11202100616V, Office Action mailed Jan. 18, 2026", 3 pgs.
"Chinese Application Serial No. 202310525133.X, Response filed Mar. 3, 2026 to Office Action mailed Jan. 7, 2026", w English Claims, 23 pgs.

TLR7 AGONIST

CHEMICAL FORMULA $C_{20}H_{24}F_3N_7O$
MOLECULAR WEIGHT 435.46

IMIQUIMOD

RESIQUIMOD

TLR7 AGONIST

JTLR7

TLR7 AGONIST

PTP1b INHIBITOR

A

B

C

D

E

PEPTIDE

SACCHARO-PEPTIDE

ALKYL

POLY ETHEYLENE GLYCOL (PEG)

POLYPROLINE

OLIGO-(4-PIPERIDINE CARBOXYLIC ACID)

OLIGO PIPERIDINE

REJUVENATION OF CAR T CELL

RELATED APPLICATIONS

This application is a continuation of U.S. application Ser. No. 17/266,509, filed on 5 Feb. 2021, which is a U.S. national stage filing under 35 U.S.C. 371 from International Application No. PCT/US2019/042726, filed on 21 Jul. 2019, and published as WO 2020/033129 on 13 Feb. 2020, which claims the benefit of U.S. Provisional Application Ser. No. 62/715,666, filed 7 Aug. 2018, the contents of which are specifically incorporated herein by reference in their entirety.

FIELD OF INVENTION

This disclosure provides a system to rejuvenate cancer antigen exhausted chimeric antigen receptor T (CAR T) cells. Specifically, the system comprising a fusion receptor in a classical CAR construct, wherein the fusion receptor provides a ligand binding module that recognizes a high affinity ligand-payload drug conjugate to deliver payload of drugs that are designed to either block the inhibitory signaling in the exhausted CAR T, or to re-activate CAR T through an antigen independent pathway.

BACKGROUND

The field of chimeric antigen receptor (CAR) T cell therapy has made tremendous progress over the last two decades. The CAR construct consists of four parts: (1) an extracellular binding moiety against tumor specific antigen, (2) a hinge domain, (3) a transmembrane domain and (4) a combination of various activation domains, for example, CD28, 4-1BB and CD3ζ chain. The most impressive successes have been seen in CAR T therapy against CD19 positive B cell leukemias, where more than 80% complete remission rate has been achieved in several clinical trials.

In contrast, the treatment of solid tumor by CAR T has so far proven to be more challenging. Great successes have been achieved in preclinical study using syngeneic mice model or xenograft tumor model in immunodeficient mice. However, none of the clinical trials involving solid tumor, for example, breast cancer, ovarian cancer or lung cancer has shown improvement compare to control. In general, it suffers from the same limitations that are faced by other adoptive cell therapies, including (1) poor tumor penetration; (2) hypoxic pressure; (3) are immunosuppressive tumor microenviroment which includes tumor associated macrophages, fibroblasts and suppressive cytokines[1]. CAR T cells, as same as tumor infiltrated lymphocytes (TIL), can be re-educated by this suppressive microenviroment and turn to a "hypofunctional" status, which is characterized by overexpression of co-inhibitory molecules (i.e., PD-1, Tim-3, LAG-3 etc.) decreased INFγ secretion and killing capability. Data from the patient samples of ovarian cancer shows that the majority of $PD-1^+CD8^+$ T cell lacked expression of CD127 which is known to be important for the effector-to-memory transition in T cell. Overexpression of LAG-3 also negatively correlated with the effector function of TCR specific $CD8^+$ TIL. In addition, $PD-1^+$ $LAG-3^+$ double positive T cell exhibited lower $INF_\gamma$ production[2]. Similarly, NY-ESO-1 TCR specific human T cell became hypofunctional in mice solid tumor model, showing high expression of the co-inhibitory molecules and less efficient anti-tumor effect, due to both the microenvironment and the constant activation of T cell by the continuous exposure to antigen[3]. Therefore, a reversion of the suppressive microenviroment, more importantly, a rejuvenation of the exhausted CAR T cell is highly desired for a better solid tumor treatment.

SUMMARY OF THE INVENTION

This disclosure provides system to rejuvenate an exhausted classical CAR T cell. The system comprises at least two components: a first component is a conjugate comprising a targeting ligand covalently linked to a payload of drug; and a second component is a targeting ligand binding module linked to membrane-anchoring module. The targeting ligand binding module of the second component recognizes the targeting ligand in the first component with high affinity to form a complex, and the payload drug either blocks the inhibitory signaling of the exhausted CAR T, or re-activates said CAR T through an antigen independent pathway. The membrane-anchoring module mediates internalization of the two component complex into the exhausted CAR T cell.

In some preferred embodiment, the aforementioned targeting ligand of the first component is folate, FITC or FK506.

In some preferred embodiment, the aforementioned targeting ligand binding module of the second component comprises a folate receptor, an anti-FITC antibody fragment or FKBP.

In some preferred embodiment, the aforementioned membrane-anchoring module is a folate receptor.

In some preferred embodiment, the aforementioned first component comprises a releasable linker between the targeting ligand and the payload drug.

In some preferred embodiment, the aforementioned first component comprises a non-releasable linker between the targeting ligand and the payload drug.

In some preferred embodiment, the binding affinity between aforementioned targeting ligand and the targeting ligand-binding module is in sub-nanomolar range.

In some preferred embodiment, the aforementioned payload of drug is a Toll Like Receptor 7 (TLR7) agonist or Simulator of interferon genes (STING) agonist.

In some preferred embodiment, the aforementioned payload of drug is an inhibitor to following proteins: SHP1/2, TC-PTP or DGKα, TGFβ.

In some preferred embodiment, the aforementioned TLR7 agonist has the structure of or

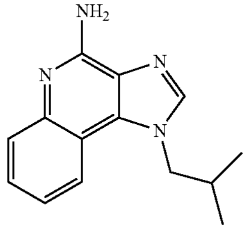

Imiquimod

-continued
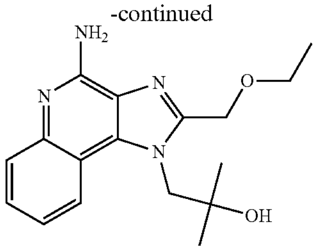
Resiquimod
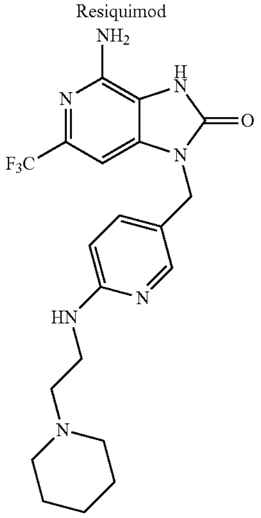
TLR7 agonist
-continued
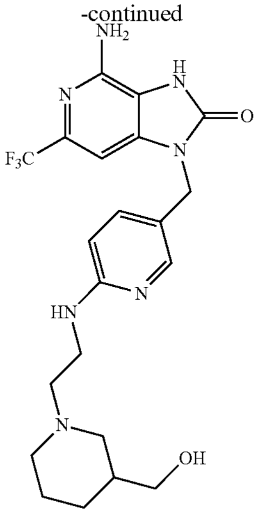
JTLR7
In some preferred embodiment, the aforementioned first component is a Fluorescein-TLR7 agonist having the structure of
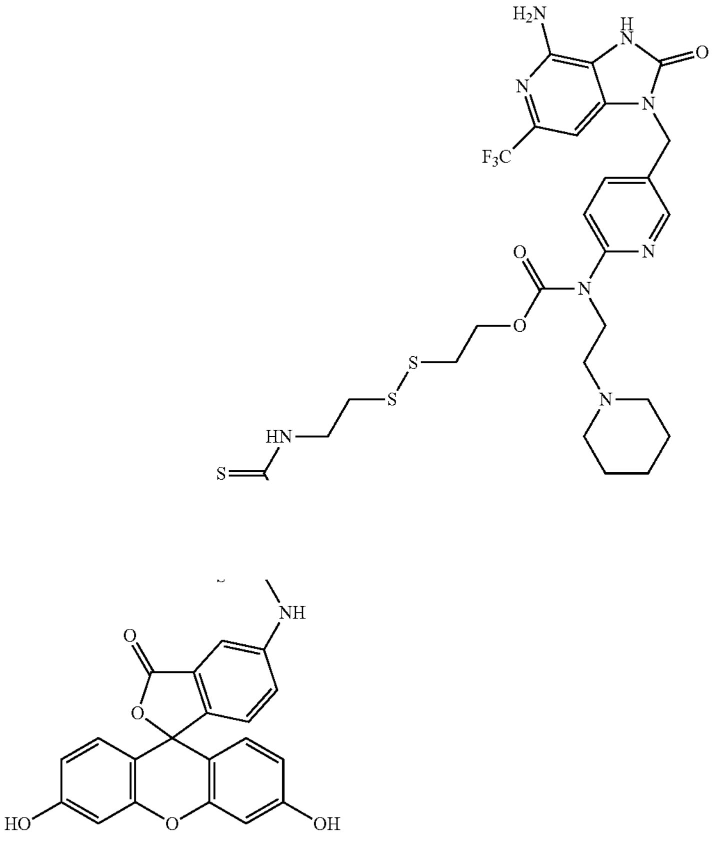
or -continued
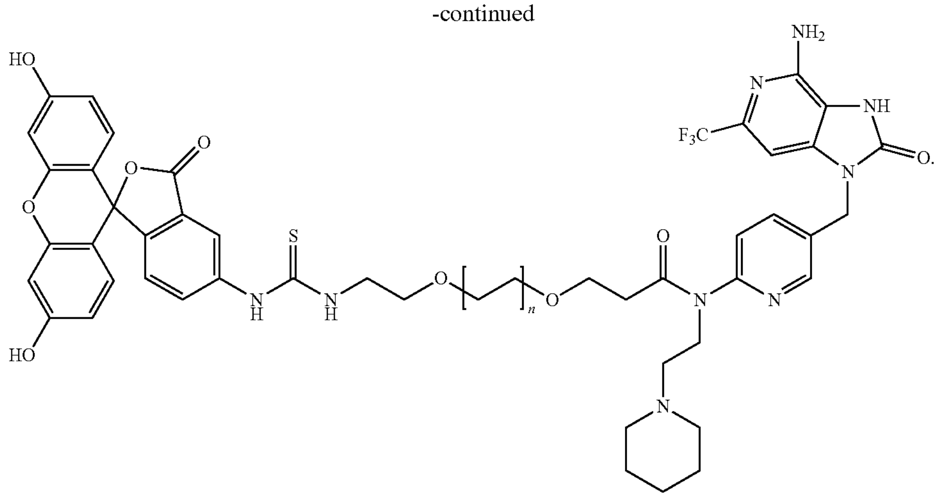
n = 0-12
In some preferred embodiment, the aforementioned first component is a FK506-TLR7 agonist having the structure of
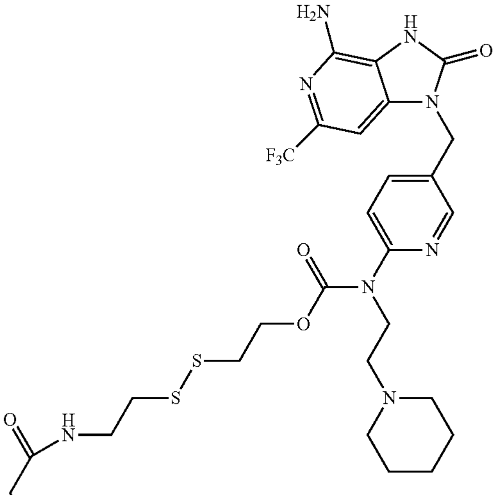
or
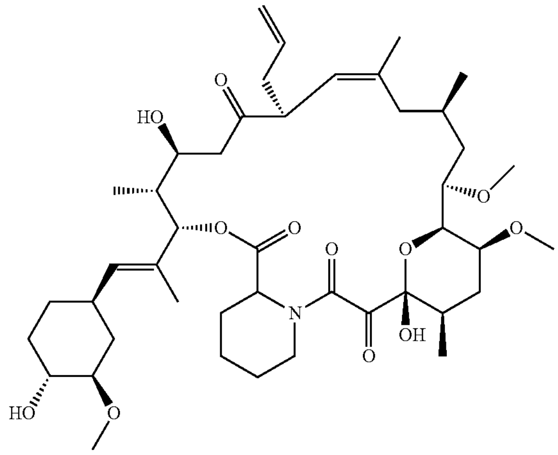

-continued
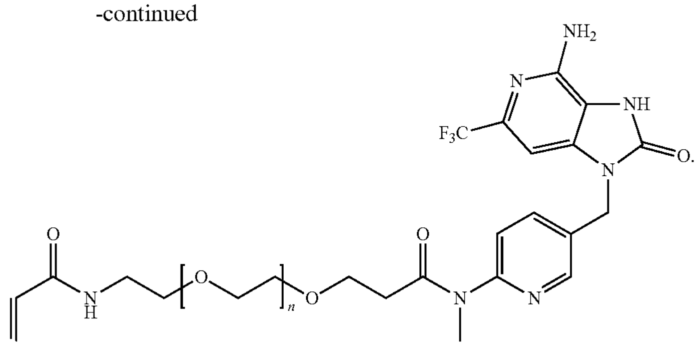
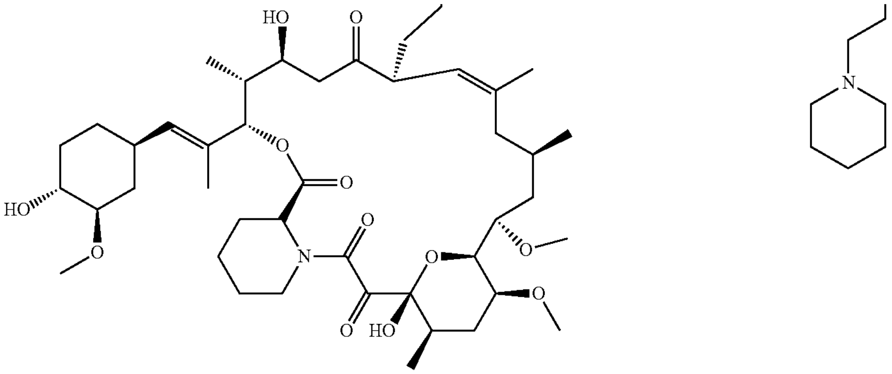
n = 0-12
In some preferred embodiment, the aforementioned first component is one of the following:
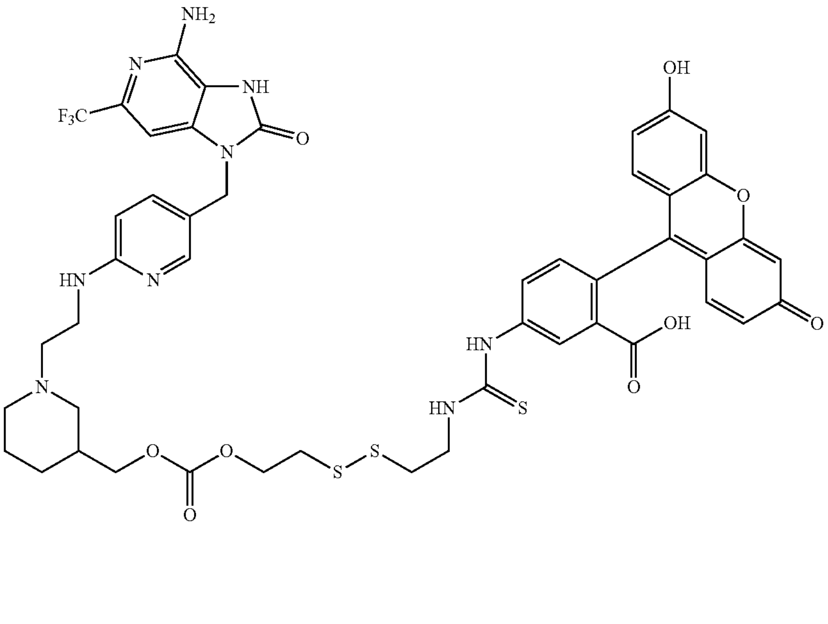

-continued
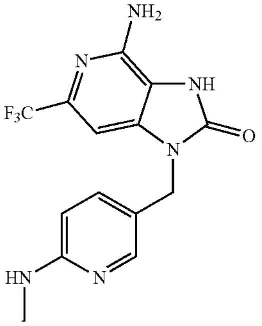
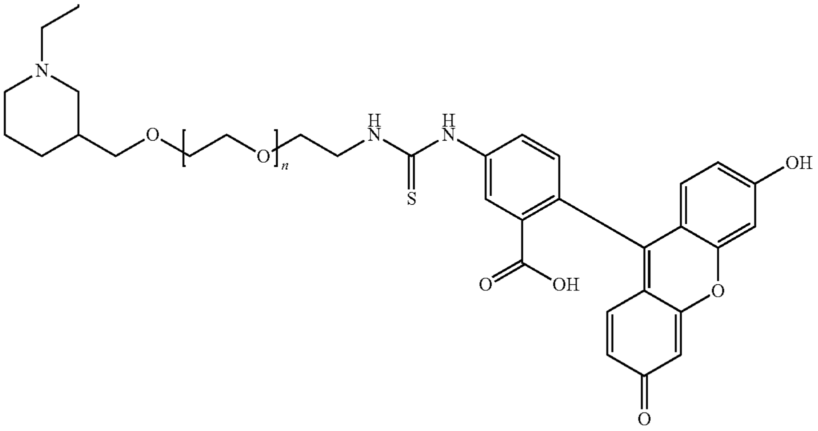
n = 0-16
In some preferred embodiment, the aforementioned first component comprising the payload drug selected from the group consisting of following TC-PTP phosphatase inhibitors:
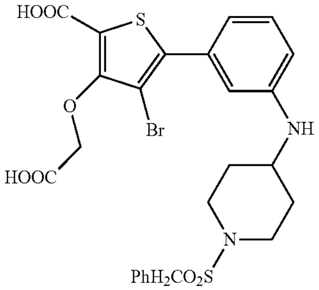
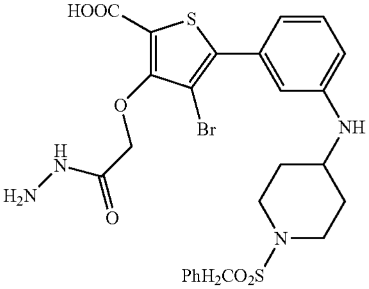
-continued
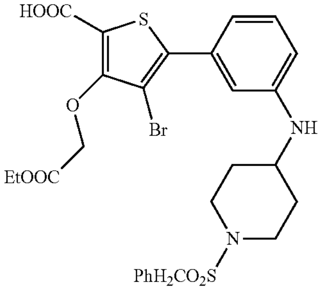
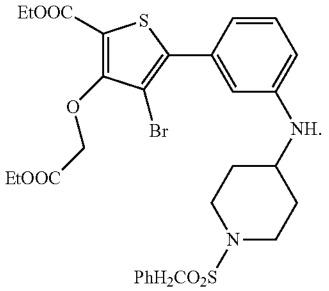
In some preferred embodiment, the aforementioned phosphatase inhibitor is connected to the fluorescein or FK506 (tacrolimus) to form the following structures:

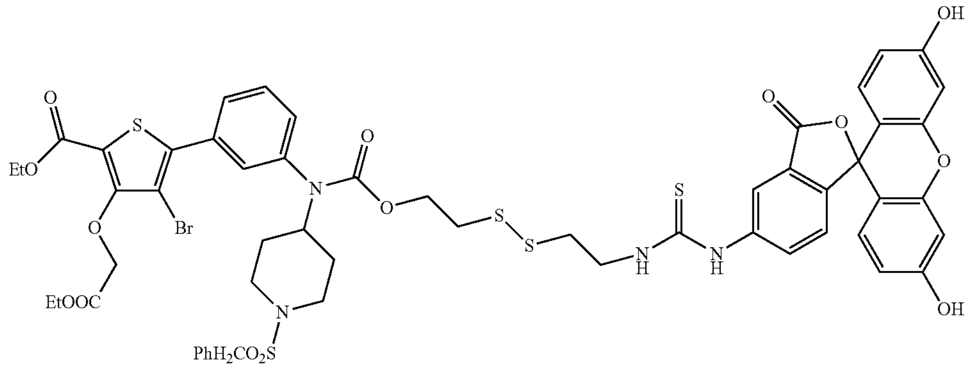

or

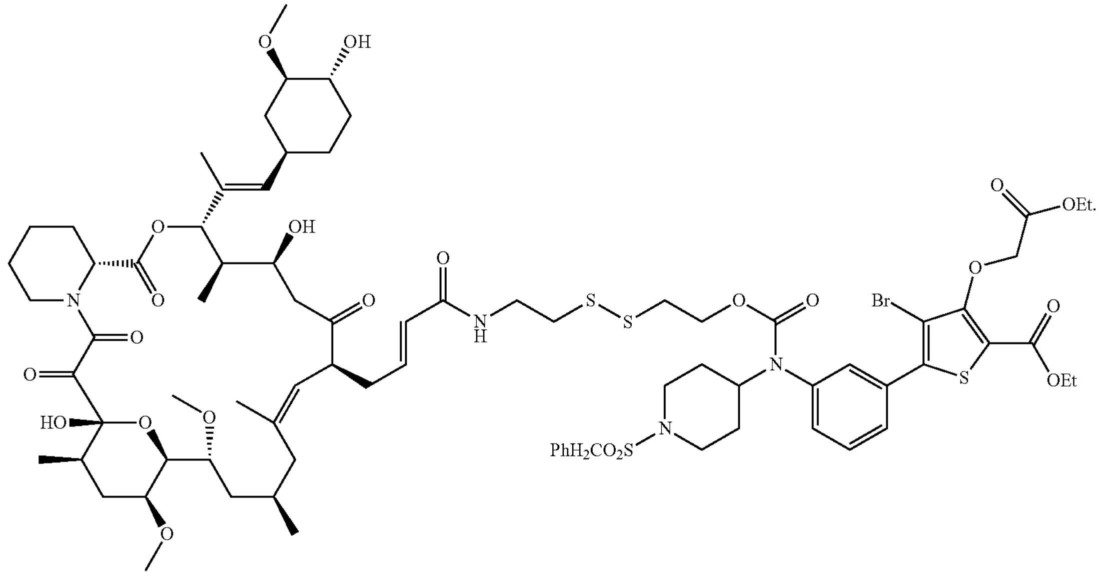

In some preferred embodiment, the aforementioned payload drug in the first component comprises a STING agonist of one of the following structures.

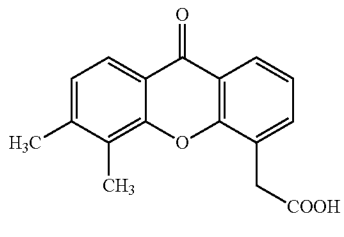

DMXAA

-continued

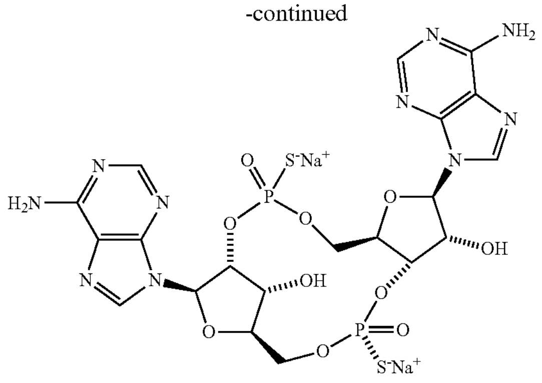

ADU-S100

In some preferred embodiment, the aforementioned first component comprises a spacer between the targeting ligand and the payload drug selected from the group consisting of the following structures:

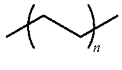

alkyl

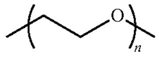

poly ethylene glycol (PEG)

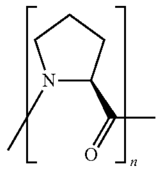

polyproline

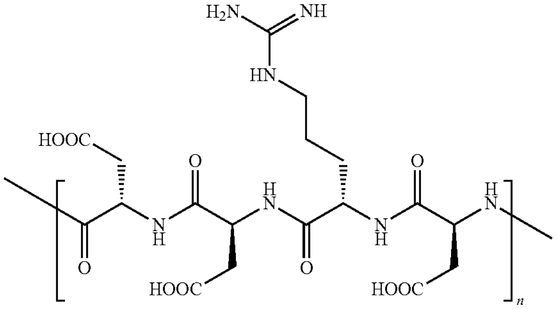

peptide

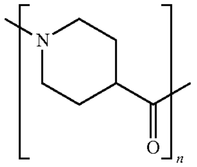

oligo-(4-piperidine carboxylic acid)

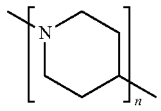

oligo piperidine

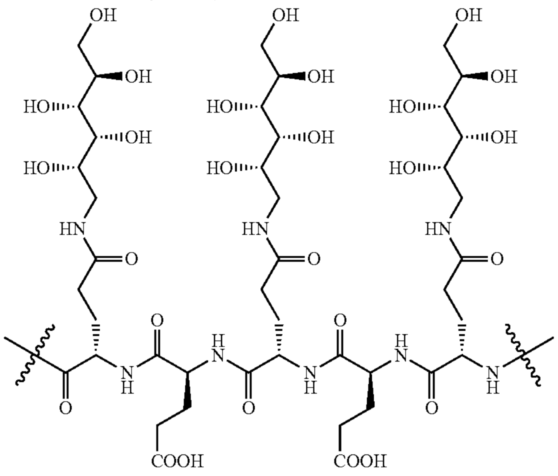

saccharo-peptide

This disclosure further provides a method to rejuvenate an exhausted CAR T cell. The method comprises the steps of:

a. providing the exhausted CAR T cell a first component comprising a conjugate, wherein the conjugate comprises a targeting ligand covalently linked to a payload of drug through a releasable or non-releasable linker;

b. providing said exhausted CAR T cell a second component comprising a fusion receptor linked to the exhausted CAR construct, wherein the fusion receptor comprises a targeting ligand binding module and a membrane-anchoring module;

c. letting the targeting ligand binding module of the second component bind to the targeting ligand in the first component to form a complex, d. letting the membrane-anchoring module mediate internalization of the complex into the exhausted CAR T cell;

e. letting the payload drug either block the inhibitory signaling of the exhausted CAR T, or re-activate said CAR T through an antigen independent pathway.

In some preferred embodiment, the aforementioned method carries a payload drug executing its function within the endosome of the exhausted CAR T, and the targeting ligand and the payload drug are linked by a nonreleasable linker.

In some preferred embodiment, the aforementioned method carries a payload drug executing its function as a free drug in the cytosol of the exhausted CAR T, and the targeting ligand and the payload drug are linked by a releasable linker.

In some preferred embodiment, the targeting ligand of the first component is folate, FITC or FK506 in aforementioned method.

In some preferred embodiment, the targeting ligand-binding module of the second component in aforementioned method is anti-FITC, folate receptor, or FKBP.

In some preferred embodiment, the targeting ligand-binding module of the second component in aforementioned method is Folate Receptor alpha (FRa).

In some preferred embodiment, the payload of drug of the first component in aforementioned method is a Toll Like Receptor 7 (TLR7) agonist or Simulator of interferon genes (STING) agonist.

In some preferred embodiment the payload of drug the first component in aforementioned method is an inhibitor to following proteins: SHP1/2, TC-PTP or DGKα, TGFβ.

In some preferred embodiment the Tur agonist in aforementioned method has the structure of

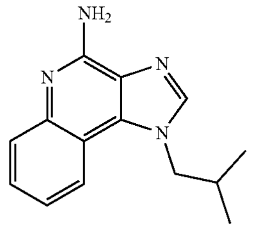

Imiquimod

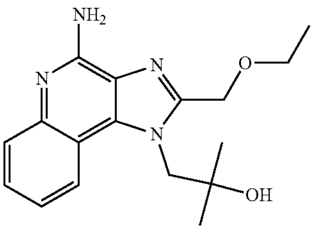

Resiquimod

-continued
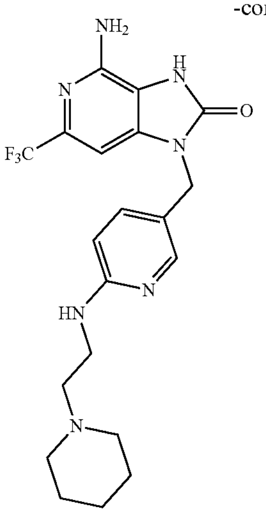
TLR7 agonist
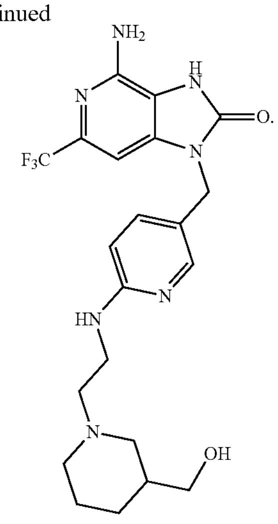
JTLR7
In some preferred embodiment, the first component in aforementioned method is a Fluorescein-TLR7 agonist having the structure of
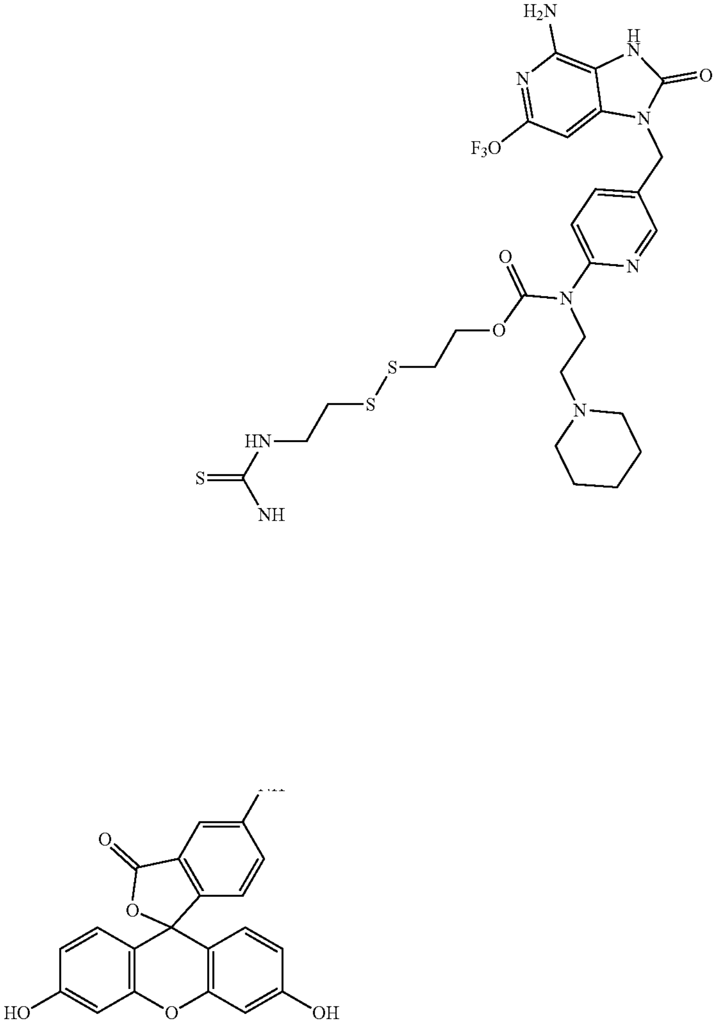
or -continued
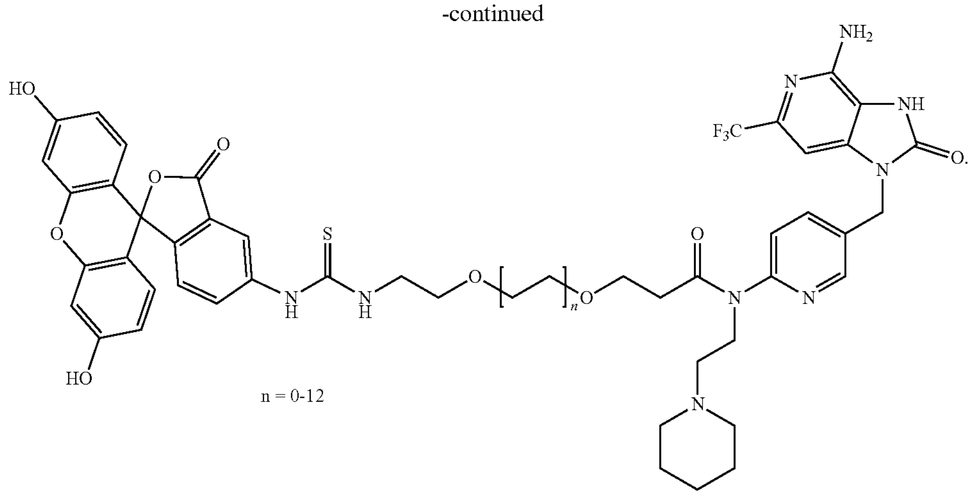
n = 0-12
In some preferred embodiment, the first component in aforementioned method is a FK506-TLR7 agonist having the structure of
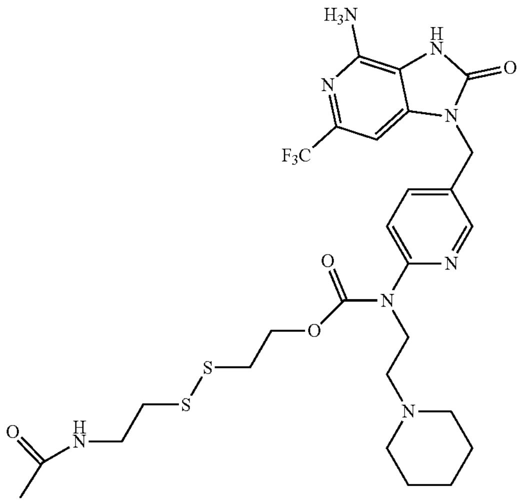
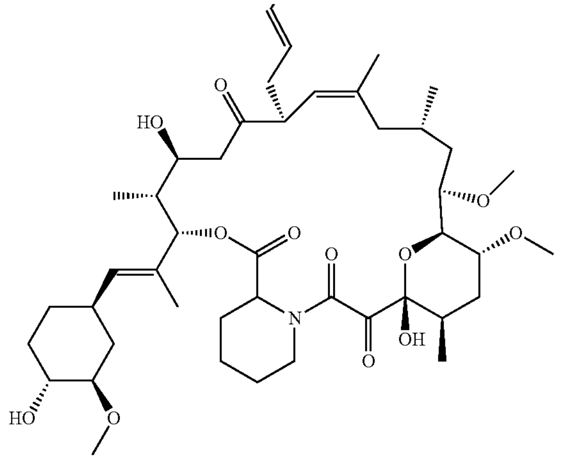
or -continued
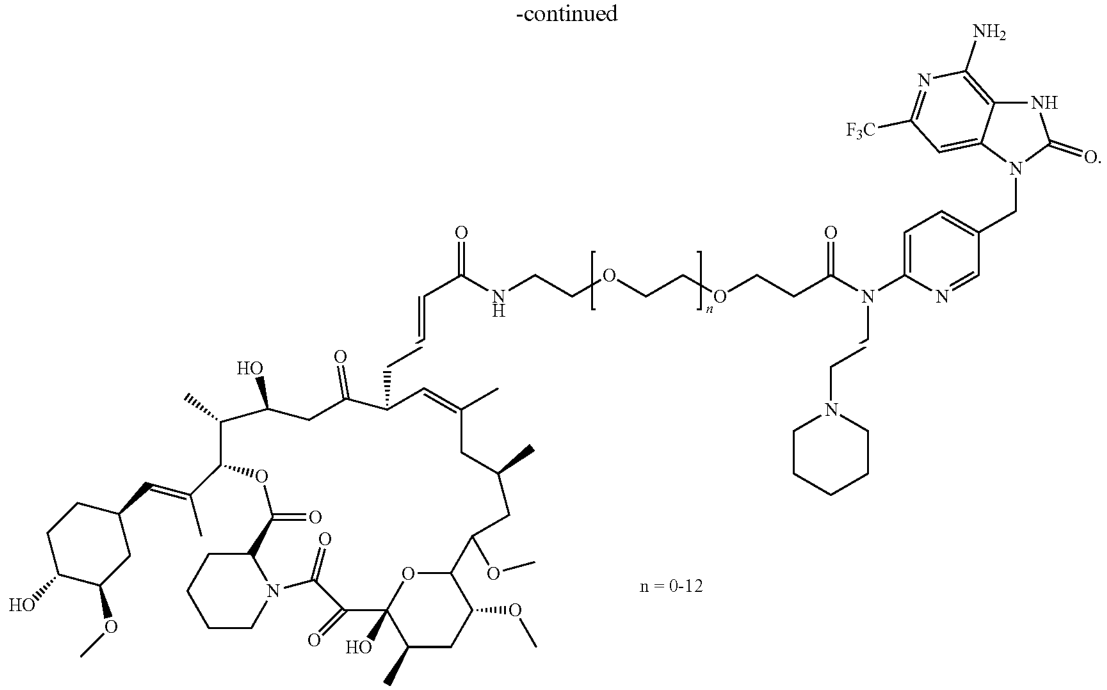
n = 0-12
In some preferred embodiment, the first component in aforementioned method is
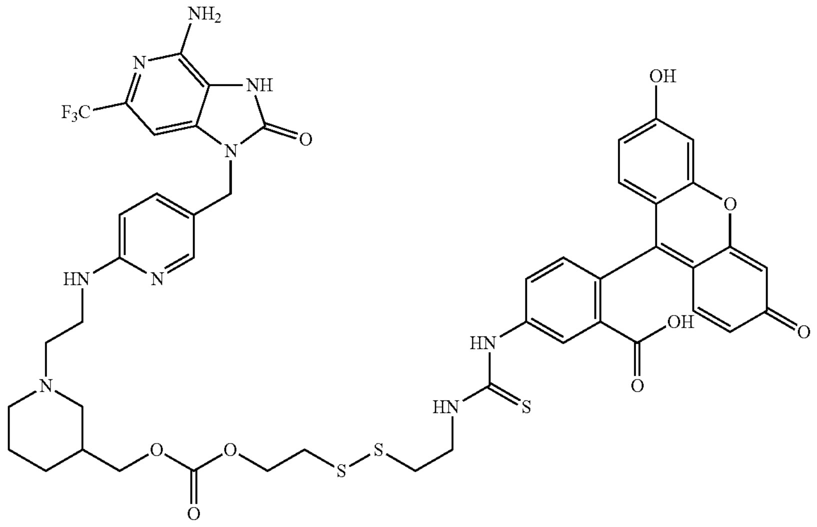
or
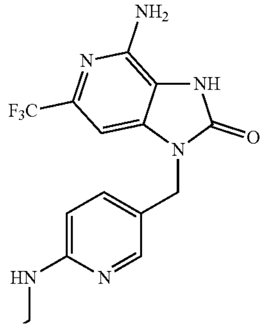

-continued

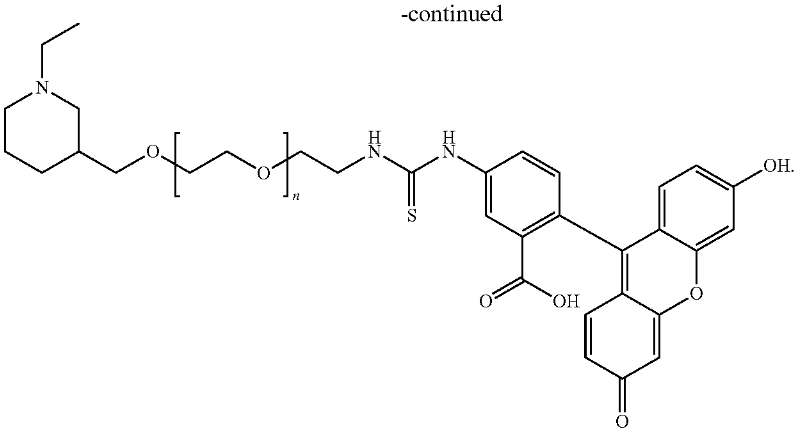

In some preferred embodiment, the first component in aforementioned method comprising payload drug selected from the group consisting of following TC-PTP phosphatase inhibitors:

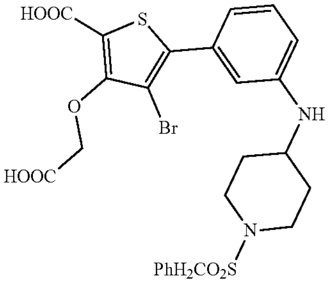

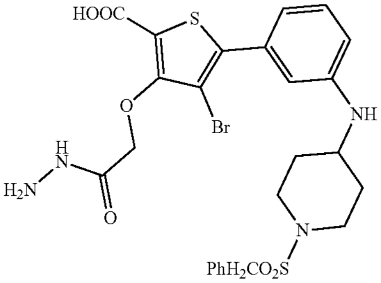

-continued

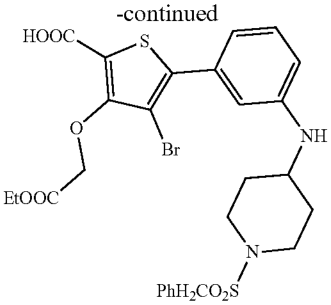

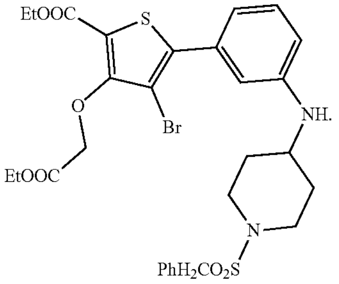

In some preferred embodiment, the first component in aforementioned method comprising the Phosphatase inhibitor connected to the fluorescein or FK506 (tacrolimus) to form the following structures:

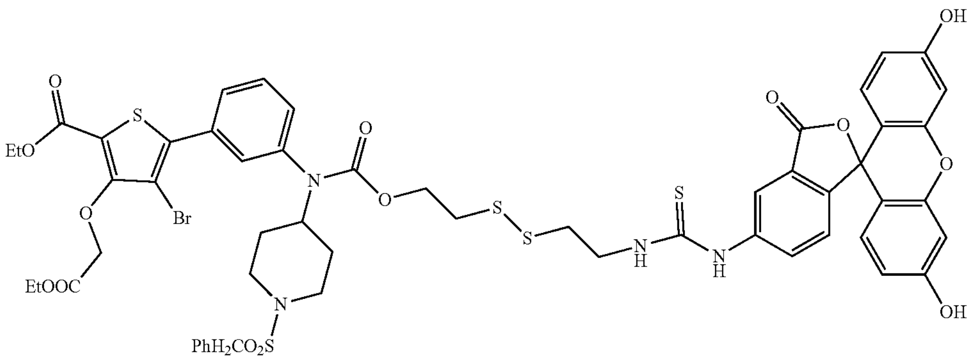

or

-continued

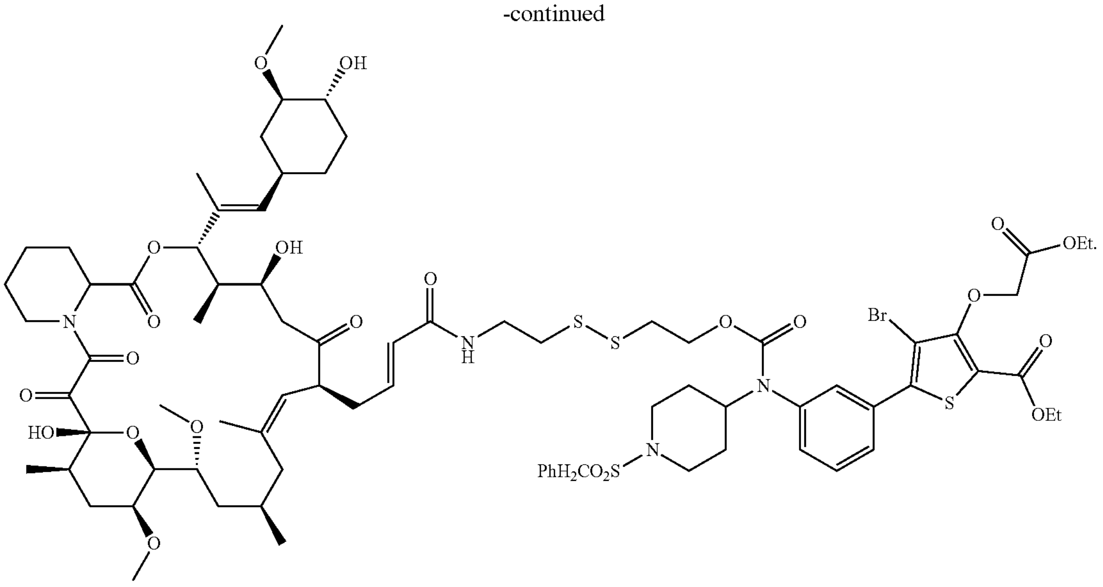

In some preferred embodiment, the first component in aforementioned method comprising a payload drug of a STING agonist of the following structures.

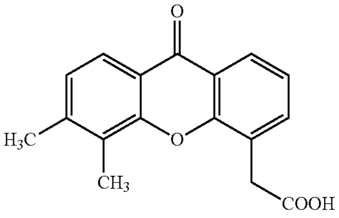

DMXAA

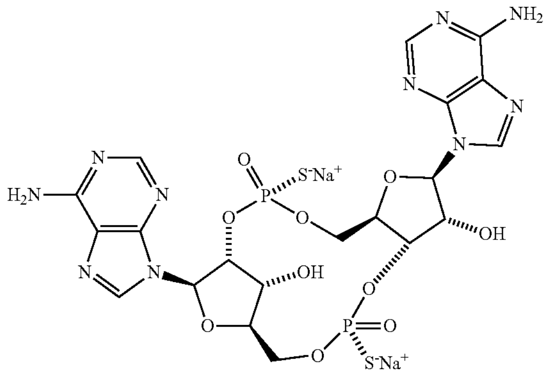

ADU-S100

In some preferred embodiment, the first component in aforementioned method comprising a spacer between the targeting ligand and the payload drug that is selected from the group consisting of the following structures:

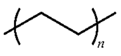

alkyl

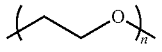

poly ethylene glycol (PEG)

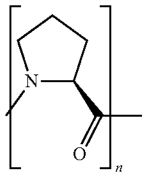

polyproline

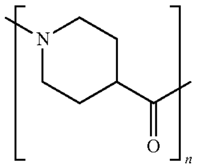

oligo-(4-piperidine carboxylic acid)

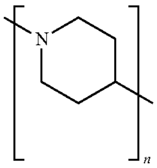

oligo piperidine

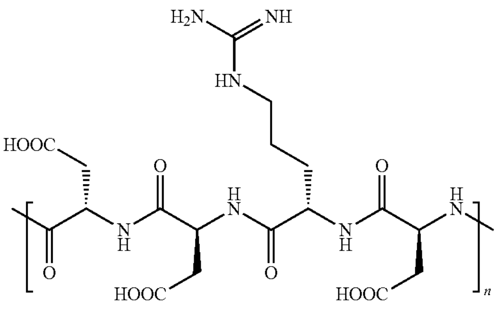

peptide

-continued

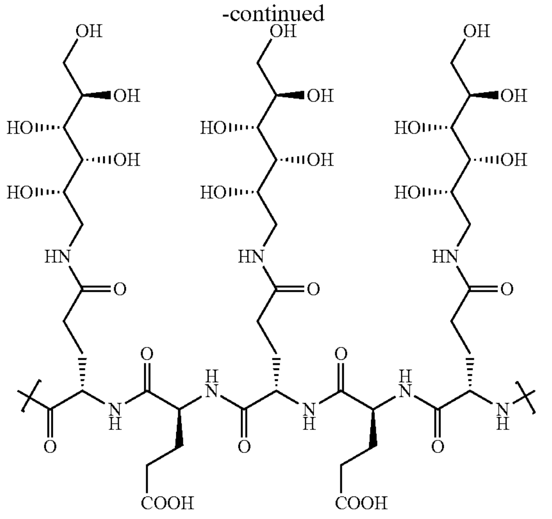

saccharo-peptide

These and other features, aspects and advantages of the present invention will become better understood with reference to the following figures, associated descriptions and claims.

DETAILED DESCRIPTION

Figure 1A:
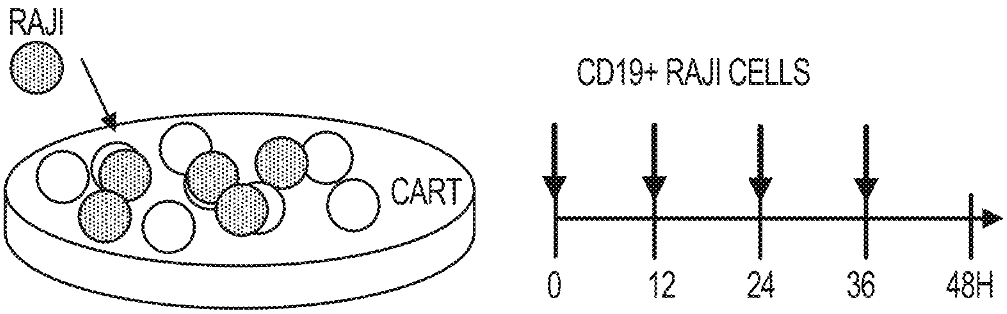
FIG. 1. 1*a*, Graph illustration of the exhaustion model. 1*b*, antiCD19 CART cell became exhausted after 3 times of stimulation of fresh Raji cell in vitro as shown by decreased killing effect.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Chimeric antigen receptor (CAR) T cell therapies have recently experienced substantial success in the treatment of several types of hematopoietic cancers. In the meantime, one should also recognize that some of the lymphoma and most solid tumor cases still have a very low response rate or a high relapse rate with CAR T cell therapies. This mainly result from one or combinations of the following three reasons: 1. Emergence of antigen negative cancer cell colonies under the selection pressure of CAR T cells, as seen in the case of CD19 negative ALL relapse treated with anti-CD19 CAR T cells; 2. Hindered initial homing, and proliferation of CART cells in solid tumor due to the aberrant tumor vasculature, dense stromal barrier and suppressive microenvironment; 3. Gradual exhaustion and lowered lysis effect of CAR T cells after continuous tumor antigen exposure. Assuming loss of antigen is not present for a given solid tumor patient (validated by biopsy sampling), the causes of a potential failure of a CAR T cell therapy are most likely to result from the latter two reasons. Therefore, to increase CAR T cells efficacy in solid tumors, practical methods for in vivo evaluation and rejuvenation of CAR T cells are highly desired.

Here we describe the novel design of a private passageway fusion receptor in CAR T cells as a universal platform to achieve both objectives: This FITC-FR fusion receptor is composed of two parts, scFv against FITC as the ligand binding domain at the N terminal and FRα as the GPI anchoring and internalizing domain at the C terminal. When independently expressed on CAR T cells, the FITC-FR fusion receptor can be specifically targeted by a FITC-immuno agonist to overcome the exhaustion status of CAR T cells in the suppressive tumor microenvironment. These immuno-agonists normally cause strong autoimmunity side effects, and can now be systemically dosed in a MC targeted form; and safely delivered to MC-FR positive CAR T cells. In the last few decades, great advances have been made in this field regarding the cell types, delivery methods and suitable diseases models: In terms of cell types, current cell therapies can be roughly categorized as chimeric antigen receptors (CARs), cell for tumor model and stem cell based regenerative medicine.

CAR T also known as chimeric T cell receptors, chimeric immunoreceptors or artificial T cell receptors, enable immune effector cells (usually T cells or NK cells) to recognize target cells with corresponding antigen and exercise their cytotoxic activity. The emergence and development of CAR-T technology provides promises to certain types of cancers which turns CAR-T into a superstar in the field of both biomedical research and clinical studies. Some traditional and improved CAR T cell design are disclosed in U.S. application Ser. No. 15/296,666, the content of which is incorporated herein entirely. In '666 application, a CAR system is produced by providing a cytotoxic lymphocytes expressing CARS that target a moiety that is not produced or expressed by cells of the subject being treated. This CAR system thus allows for focused targeting of the cytotoxic lymphocytes to target cells, such as cancer cells. The targeted moiety is part of a small conjugate molecule (SCM) that also comprises a ligand of a tumor cell receptor. Administration of a SCM along with the CAR-expressing cytotoxic lymphocytes results in the tailing of the cytotoxic lymphocyte response to only those cells expressing the tumor receptor to which the SCM is bound.

Despite the rapid progress of CAR T cell therapy in both research and clinical use field, there are concerns accompanied with CAR T therapy. One lethal side effect is cytokine storm generated from the fast lysis of tumor cells as well as it kills normal cells bearing CAR. In order to address such side effects, targeted delivery of CAR T cell with specific payload of drug to the target tumor cells to control such side effect is developed in PCT/US2018/018557, the content of which is incorporated herein entirely. Briefly, an engineered protein is coupled with a high affinity targeting ligand, wherein the targeting ligand carries at least one payload of drug to be internalized by the CAR T cell through the engineered protein to regulate transplanted cell therapy effects.

Another limitation of CAR T therapy is their tendency to get exhausted after repeated stimulation of cancer antigen. The reversibility of the exhausted phenotype of T cell is proven as T cells isolated from the solid tumor tissue show higher INFγ secretion and killing effect if kept away from antigens ("rested") overnight before re-stimulation[4]. However, it will be more appealing if rejuvenation can be achieved in a more clinical relevant way using drugs: either to block the inhibitory signaling or to activate the T cell through other pathways. Antibodies targeting checkpoint inhibitors (i.e. PD-1 CTLA-4 etc.) have shown some success in solid tumors in clinic, however, two or more targets in combination are often found to be necessary[5 6]. Moreover, antibody therapy also suffers from poor penetration in solid tumor. Therefore, less reports have been seen for the combination therapy of CAR T and antibody for checkpoint inhibitors in solid tumor. Inhibiting the phosphatases, such as SHP1/2[7] and TC-PTP[8], that mediates TCR deactivating, is another way to block the inhibitory pathways. Both knockout experiments and small molecules inhibitors of these phosphatases have shown potent effect on lowering TCR threshold and increasing T cell activity, but none of them have been used in CAR T therapy. DGKα is another physiological inhibitor of TCR signaling and it's overexpressed in exhausted TIL. DGKα catabolize DAG to PA thereby reducing DAG levels, which results in attenuation of Ras and MARK ERK signaling. Inhibitor of DGKα recovers the degranulation and increases the killing effect of TIL and CAR T[3 9]. Another approach to rejuvenate the T cell is to activate it through an antigen independent pathway. It has been known that certain pathogen pattern recognition (PPR) receptors, including Toll like receptors (TLR), do express on non-myeloid cell populations, including T cells, and can be activated in a similar way. Research has also shown that TLR2[10], 4[11] and 7/8[12 13] agonists can activate CD8 T cells and increase INFγ secretion. However, due to the strong side effects of systemic dosing of TLR agonists[14], none of these agonists have been used in CAR T therapy to re-activate the T cell or change the immunosuppressive microenviroment. It's also hindered by the controversial effect of TLR agonists on tumor cell itself[15]. Stimulator of interferon genes (STING) is a cytosolic DNA sensor (CDS) that widely expressed in hematopoietic cells in peripheral lymphoid tissues, including T cell, myeloid cells and monocytes. STING agonists have been used as an immune stimulator for many immunotherapies, and may also have a profound effect in CAR T therapy. However, although the mentioned inhibitors and agonists may have a profound rejuvenation effect on CAR T cell, ifs also highly possible that it may induce severe side effects if systematically dosed due to their highly potent pro-inflammatory functions. Therefore, a targeted delivery of the potential payloads to the CAR T cell is highly desired.

To solve the specific delivery problem, we designed a secret passageway platform, which can be expressed in T cell together with the CAR construct, so that certain payloads can be systemically dosed and specifically accumulated within the CAR T cell only, rendering other cells untouched. The system consists a fusion receptor and a classical CAR construct, linked through a T2A self-cleavable sequence. The fusion receptor contains two parts: (1) a ligand binding module, which can recognize a high affinity ligand-payload conjugate; (2) a membrane bound receptor module, which can mediate the internalization of the receptor/conjugate complex into the cell. Two protein/ligand pairs have been chosen for part 1, FKBP/FK506 and scFv against FITC (4M5.3)/FITC, for the following reasons: (1) the absence of FKBP or 4M5.3 on natural cell membrane guarantees the specific delivery of payload to fusion receptor positive CAR T cell, thus reduces the side effects to other cells; (2) the sub-nanomolar binding affinity between protein/ligand pairs promote sufficient payload accumulation inside the targeted cells. For the membrane bound receptor in part 2, Folate Receptor alpha (FRa) was chosen for its constitutive internalization properties regardless of Folate Acid binding[16]. We also designed a target-payload linkage system, where payload can be linked to targeting ligands with either non-releasable linker or a disulfide releasable linker, depending on the target. More specifically, since TLR7 locates in the endosome, secret passageway delivered TLR7 agonist can exert its function as soon as it enters the endosome through receptor mediated internalization. Therefore, releasable linker is not necessary in this case. While for other targets that are located in the cytosol instead of the endosome, such as SHP1/2, TC-PTP, DGK, TGFβ and STING, release of the free drug from the target-payload conjugate is necessary for its escape from the endosome.

Together, this secret passageway system provides a versatile platform for specific in vivo delivery of numerous payloads to the exhausted CAR T cell.

These and other features, aspects and advantages of the present invention will become better understood with the following experiments examples.

Methods

Exhaustion of the AntiCD19 CAR T Cell and Drug Treatment:

AntiCD1.9 CAR T cell were co-cultured with Raji at 1:1 ratio in 6 well plate, while fresh Raji cell were added every 12 h to the same well. Killing effect and co-inhibitory markers were quantified by flow cytometry counting. For drug treatment, after 4 rounds of stimulation with Raji cells, exhausted antiCD19 CAR T were further incubated with drugs at different concentration for 12 h, and then quantified similarly.

Targeting Ligand Binding Assay

Fusion receptor positive cells were incubated with certain ligand-dye molecule at different concentrations for 30 min at 4 degree. After incubation, cells were washed twice with PBS and then submitted to flow cytometry. MFI or percentage of shift is used for binding curve and calculation of Kd.

Materials

Cell Lines and Human T Cells

DMEM (Giber)) containing 10% heat-inactivated fetal bovine serum and 1% penicillin-streptomycin was used for the culture of MDAMB-231 and MDA-MB-231 $CD19^+$ cells. Peripheral blood mononuclear cells (PBMCs) were isolated by Ficoll density gradient centrifugation (GE Healthcare Lifesciences, #17-5442-02) from human whole blood obtained from healthy volunteers. Pure CD3+ T cells were enriched from PBMCs using an EasySep™ Human T Cell Isolation Kit (STEM CELL technologies, #17951).

Evaluation of Potential Payloads for In Vitro Rejuvenation of Exhausted CAR T Cells anti-CD19 CAR T cells were co-incubated with $CD19^+$ Raji cell at 1:1 ratio in 12-well plate at density of $2\times10^6$ CAR T and $2\times10^6$ Raji per well, new Raji cell were added every 12 h for 3 times, Raji cell population, lysis effect and co-inhibitory receptors were then tested to confirm the exhaustion of the CART cells. Both flow cytometry and luciferase-based assays were used to quantify the lysis effect. To test the rejuvenating efficacy of the potential payloads, this cell mixture was then transferred to 96-well plate, around $2\times10^5$ cells per well, and different concentration of drugs were added. After 12 h, Raji cell population, lysis effect and co-inhibitory receptors were tested again and compared to the PBS treatment group.

EXAMPLES

Example 1. Exhaustion of the AntiCD19 CAR T Cell In Vitro

Figure 1B:
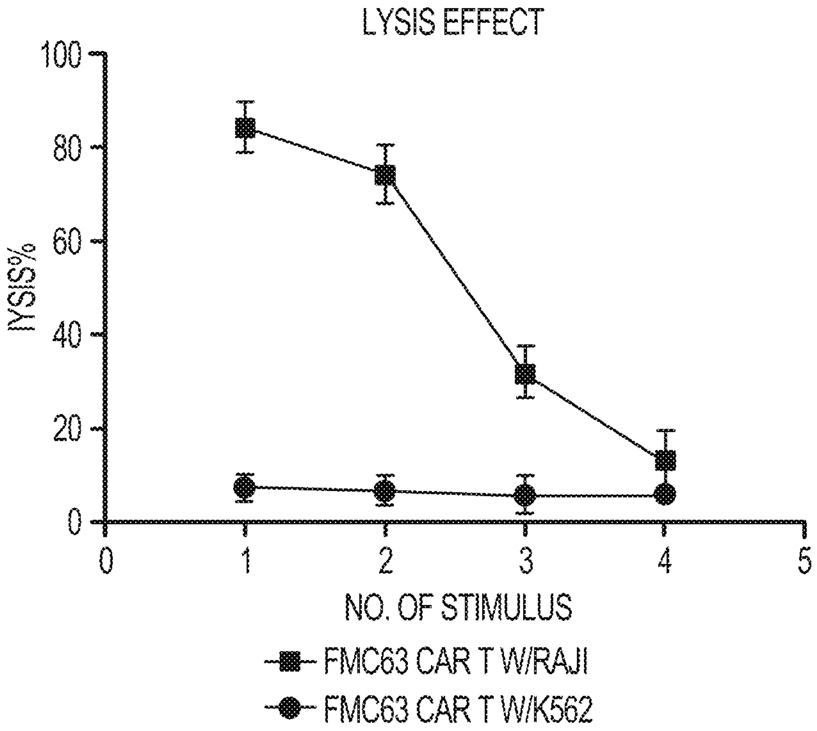
Figure 2:
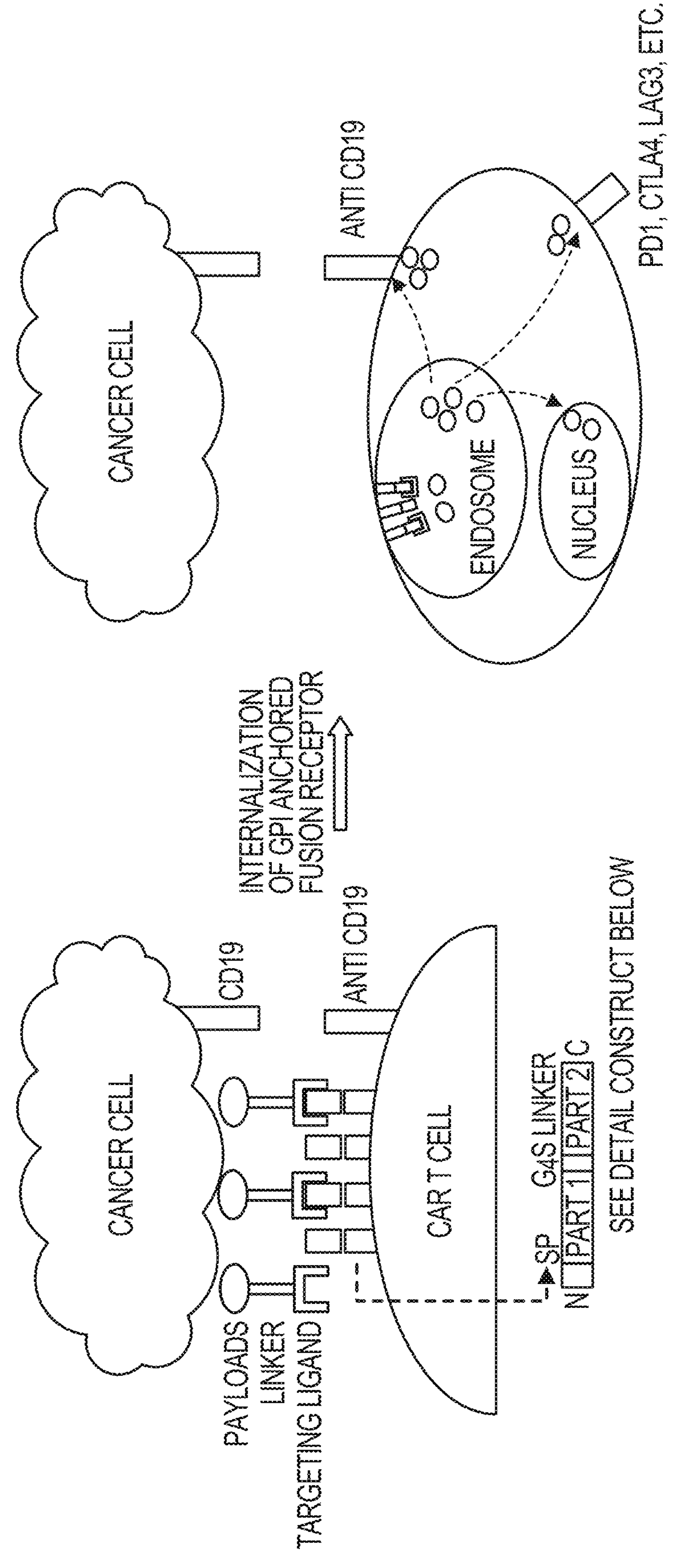
FIG. 2. Graph illustration of the secret passageway. FKBP or antiFITC is linked to FRa as a fusion receptor, which constantly internalizes and delivers FK506 or FITC linked payloads into the cell.
Figure 3:
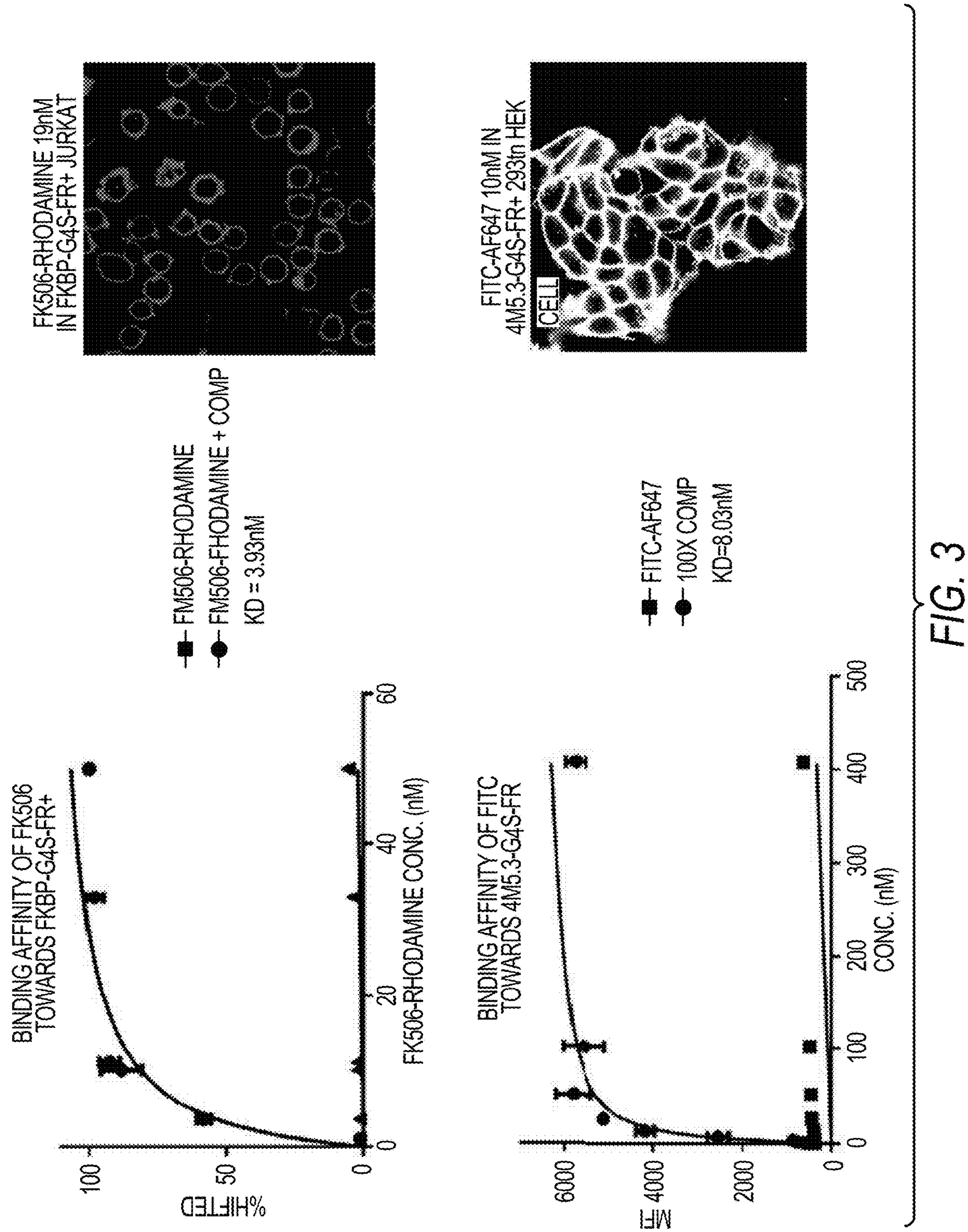
FIG. 3. Binding affinity of FK506 and FITC to the corresponding fusion receptors. FK506-Rhodamine shows Kd=3.39 nM towards FKBP-FR fusion receptor, while FITC-AF647 shows Kd=8.03 nM towards antiFITC-FR.
Figure 4A:
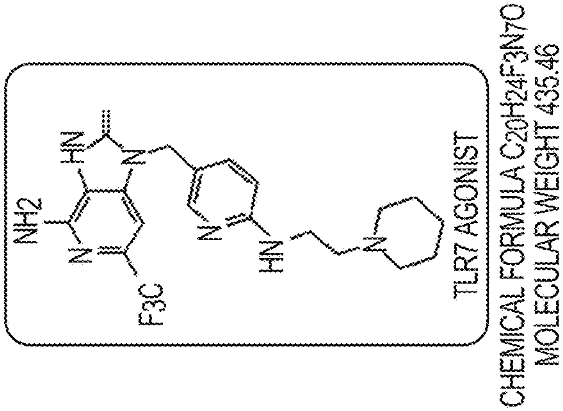
FIG. 4. 4*a*. Structure of the TLR7 agonist. 4*b*. rejuvenation effect of TLR7 agonist on exhausted antiCD19 CART cell, shown as the increased killing effect, INFr level and decreased co-inhibitory molecule level.
Figure 4B:
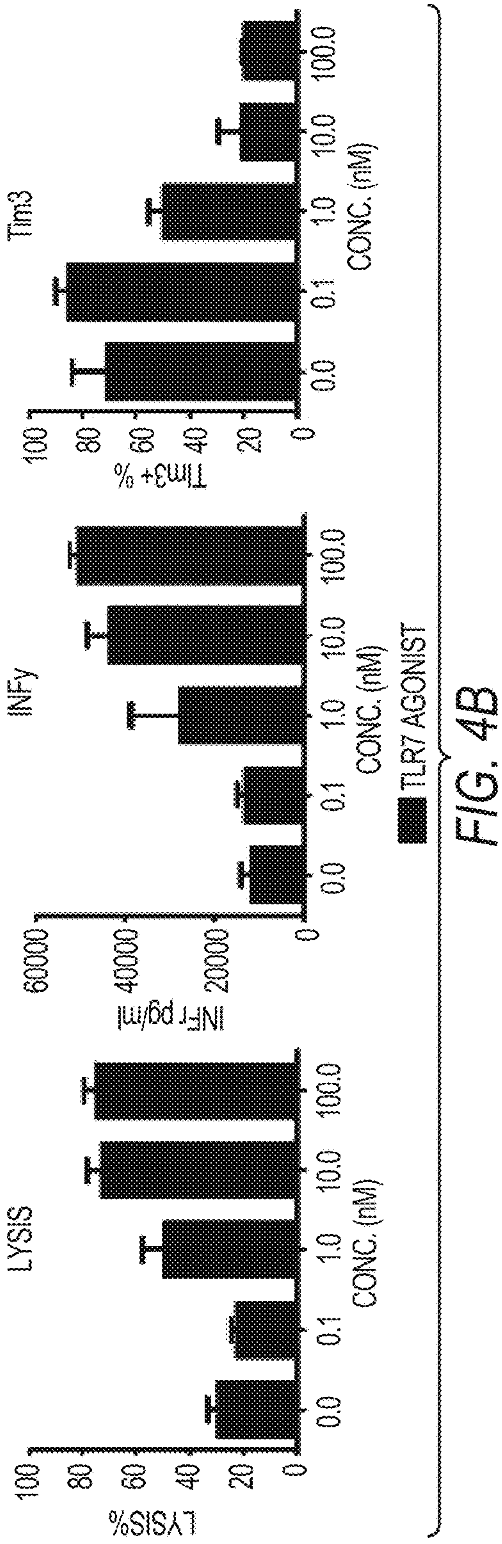
Figure 5:
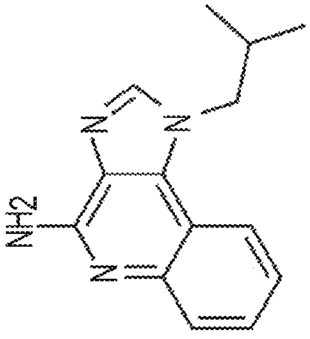
FIG. 5. Chemical Structure of TLR7 agonists.
Figure 5:
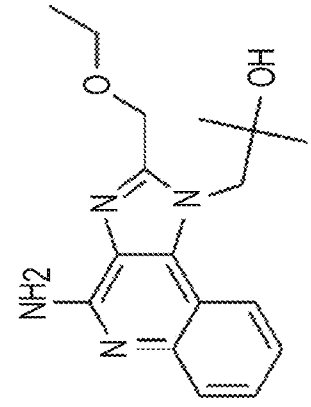
Figure 5:
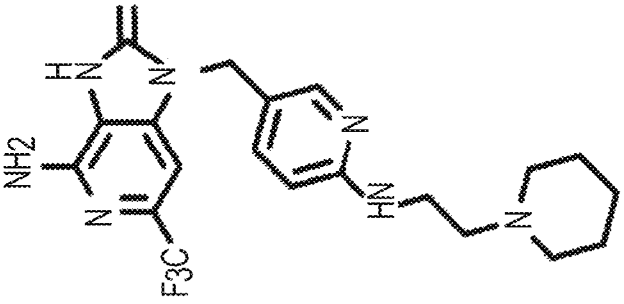
Figure 5:
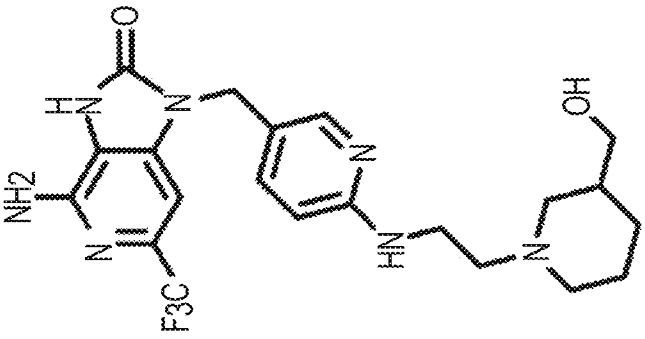

In this Example, we illustrated a model of exhausted CAR T cell. Briefly, FIG. 1*a* shows Raji cells, a type of B-lymphoma cells were co-cultured with FMC63 CAR T cells, a type of anti CD19 CAR T cells as described in the method section, and fresh Raji cells were added to the co-culture every 12 hours for consecutive three days. FIG. 1*b* shows these CAR T cells became exhausted after 3 times of stimulation by fresh Raji cells in vitro, indicated by decreased killing effect. Co cultured K562 cells served as negative control.

Example 2. Design of the Secret Passageway

In this Example, we show a graphic illustration of the secret passageway of delivery payload drug to targeted cell types. FKBP or antiFITC is linked to FRa as a fusion receptor, which is able to engage a targeting ligand FK506 or FITC linked to a specific payload of drug. Due to the nature of FRa, it constantly internalizes and delivers FK506 or FITC linked payloads into the CAR T cell. Therefore, when CAR T is engaged to its target cells through CAR, in this example, anti-CD 19 molecule on the CAR T surface engages CD-19 of the cancer cell, the delivered payload drug inside of CAR T may execute its function, i.e. regulate CAR T activity based on the payload function. For example, some payload drugs may be directed to act on PD-1, CTLA4, or LAG3 T cell function regulatory molecules to rejuvenate CAR T when necessary.

Example 3. Reversion of the Exhausted AntiCD19 CAR T Cell by TLR7 Agonist

In this Example, we show that targeting ligand FK506 or FITC successfully engages its respective fusion receptor (FKBP or FITC-AF647 linked to Folate Receptor by $G_4S$). In this example the payload drug is an imaging agent Rhodamine to show the payload distribution in fusion receptor transfected Jurkat cells. The binding affinity FK506 and FITC are calculated by competitive binding and FK506-Rhodamine shows Kd=3.39 nM towards FKBP-FR fusion receptor, while FITC-AF647 shows Kd=8.03 nM towards antiFITC-FR

Example 4. Design of Potential Releasable and Non-Releasable FK506-TLR7 Agonist and FITC-TLR7 Agonist In this Example, we provided targeting ligand FK506 conjugated to a Toll Like Receptor 7 agonist with the structure below to treat exhausted CAR T cells. A dose dependent pattern of increased killing effect is observed when TLR7 agonist payload drug is targeted to exhausted CAR T cells. Accordingly, the indicator of CAR T activity, $IFN_\gamma$ expression level, increased in a dose dependent manner relative to payload drug concentration; and the expression level of a T cell effect inhibitory molecule, Tim 3, had showed a reverse dose dependence manner, i.e. Tim 3 expression decreased as the concentration of payload drug is increased.

FK506-TLR7 agonist conjugate should have one of the structures given below:
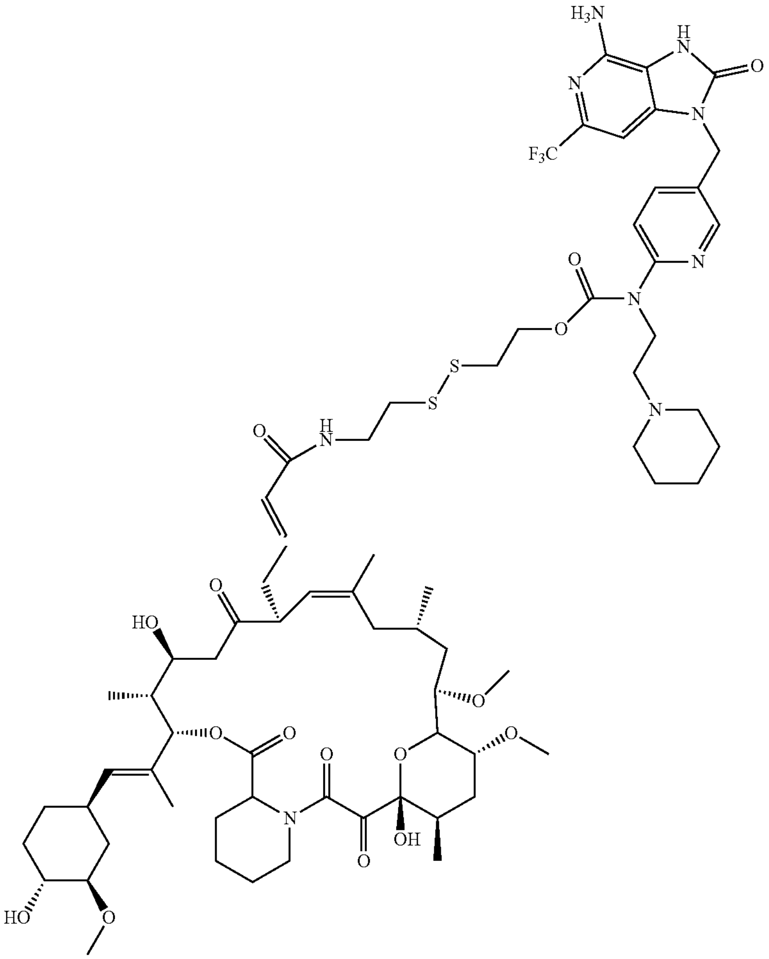
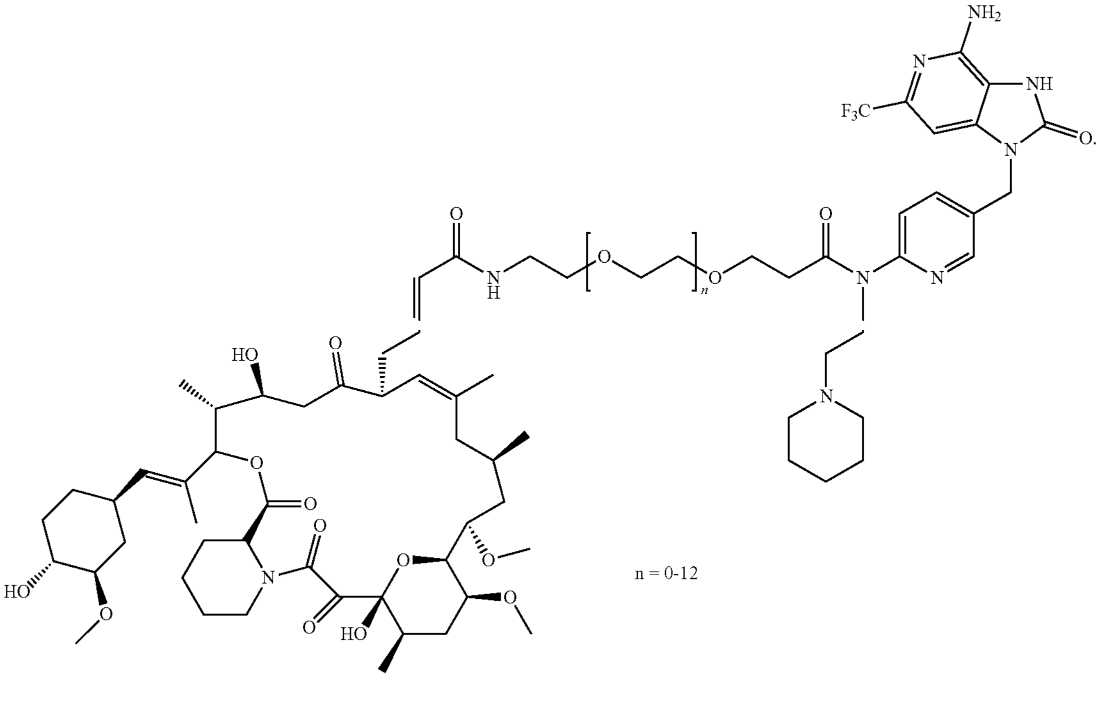
n = 0-12

Similarly, Fluorescein-TLR7 agonist conjugate should have one of the structures given below and rejuvenate exhausted CAR T if the functional CAR T has an anti-FITC fusion receptor.
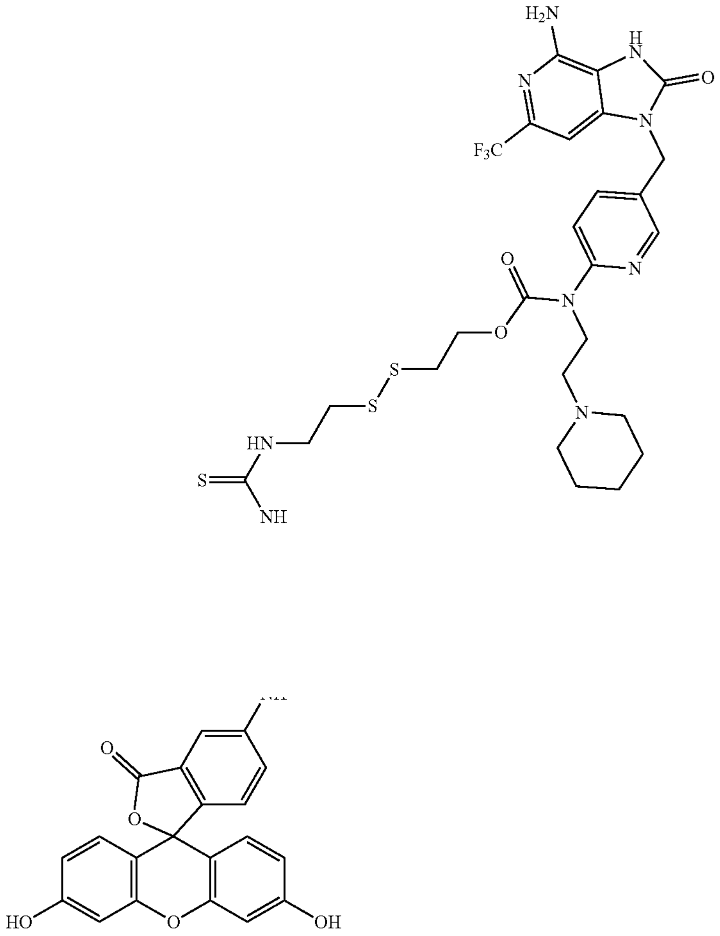
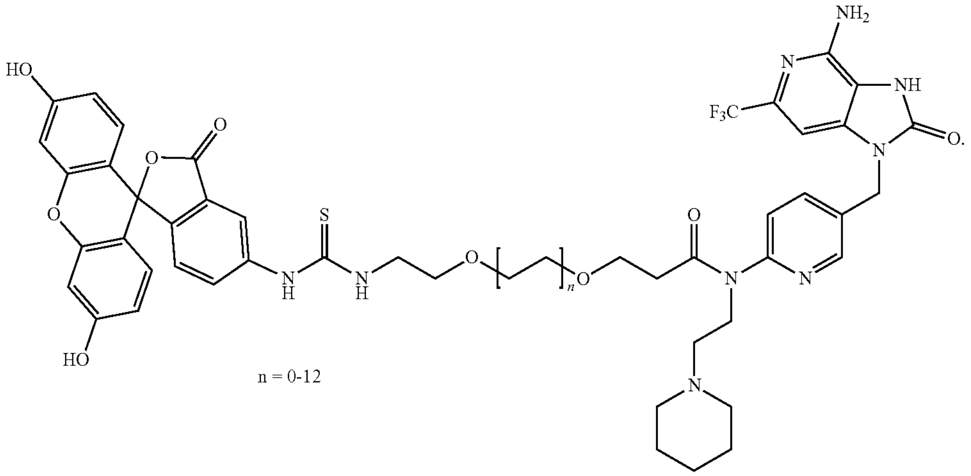
n = 0-12

Example 5. Design of Other Potential Payloads for the Rejuvenation of the Exhausted CAR T Cell In this Example we provide a list of structures of other potential payloads that may revert CAR T exhaustion with lower nanomolar range potency.

1) TC-PTP phosphatase inhibitor should have the following structures,

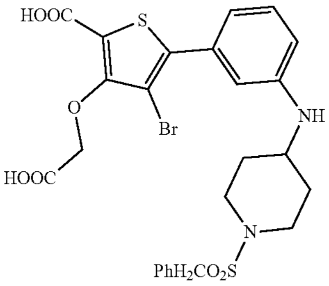

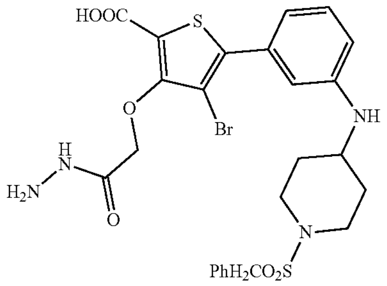

-continued

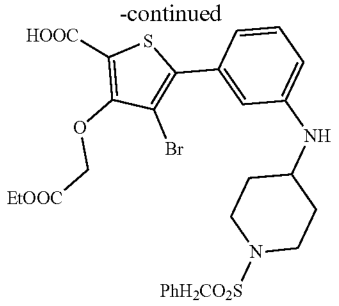

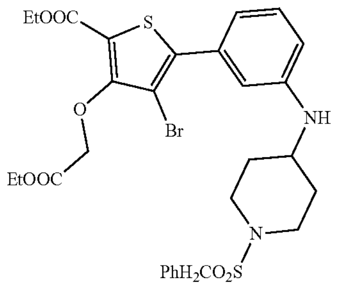

Phosphatase inhibitor mentioned above may be connected to the fluorescein or FK506 (tacrolimus) in the following way.

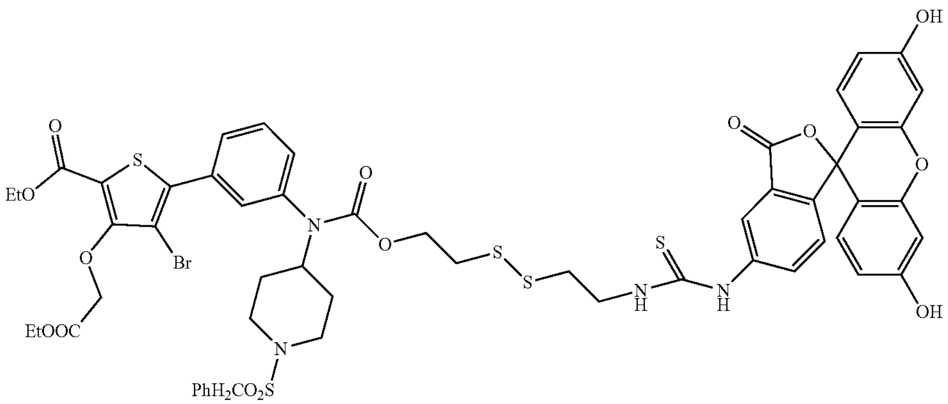

-continued

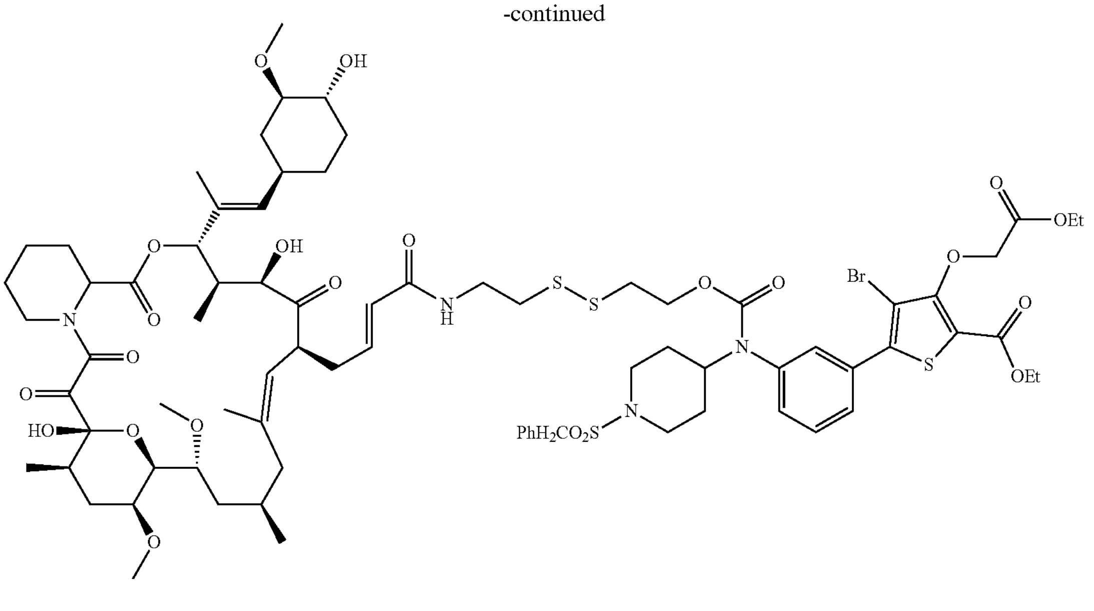

2) The STING agonist should have the following structure,

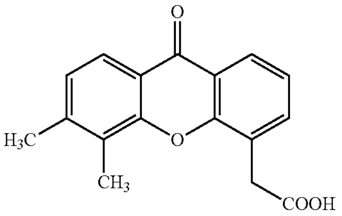

DMXAA

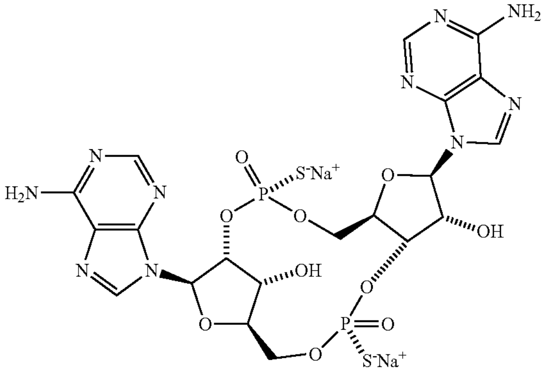

ADU-S100

Example 6. Design of Spacers Between Targeting Ligands and the Potential Payloads Below are a list of spacers that can be employed to link the targeting ligands and any potential payloads.

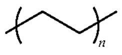

alkyl

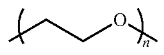

poly ethylene glycol (PEG)

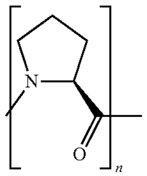

polyproline

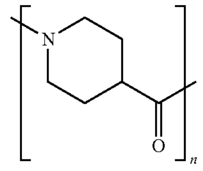

oligo-(4-piperidine carboxylic acid)

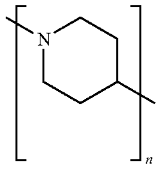

oligo piperidine

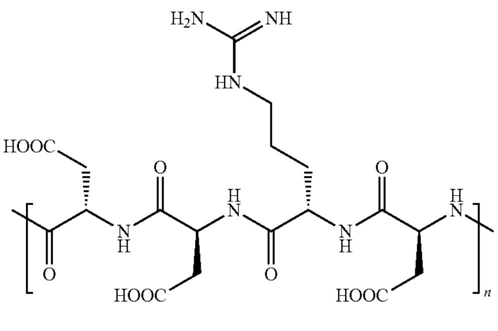

peptide

-continued

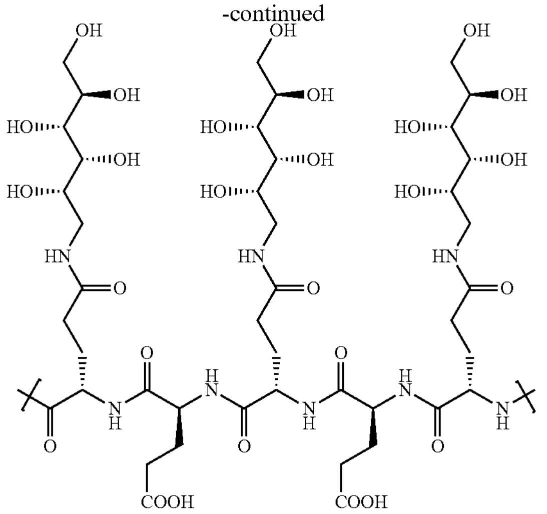

saccharo-peptide

Example 7. Evaluation of the Ability of Phosphatase Inhibitors and TLR7 Agonists to Rejuvenate Exhausted CAR T Cells One major limitation of CAR T cell therapies in solid tumors is their tendency to become exhausted after repeated stimulation with cancer antigens. This phenomenon however, is not specific to CAR T cells, but has been described in both chronic virus infections[4] and tumor infiltration lymphocytes[5]. The reversibility of the exhausted phenotype of T cells has been proven in studies where T cells isolated from the solid tumor tissue show a higher INFγ secretion and a killing effect if kept away from antigens ("rested") overnight before re-stimulation[57]. However, it would will be more appealing if rejuvenation could be achieved in a more clinically relevant way using commercially available therapeutics: either to block the inhibitory signaling or to activate the T cells through other pathways. Antibodies targeting checkpoint inhibitors (i.e. PD-1, CTLA-4, etc.) have shown some success in solid tumors in-clinic[151], however, two or more targets in combination often have been found to be necessary. Moreover, antibody therapy also suffers from poor penetration in solid tumors and this may have led to less reports for the combination therapy of CAR T cells and checkpoint blockades (ICB) in solid tumors.

The inhibition of the phosphatases, such as SHP1/2 and TC-PTP, that mediate TCR deactivation, is a potential way to block tonic CAR T signaling. SHP1/2 phosphatase is responsible for mediating the signal from PD-1 and other exhaustion markers. Data has shown that SHP1/2 phosphatase inhibitor or silencing can increase the activity of T cells and CAR T cells[6-9]. TC-PTP is known to be an important player in T cell activity signaling. Mice harboring a T cell specific TC-PTP deficiency have increased susceptibility to inflammation and autoimmunity due to heightened antigen-driven T cell activation. TC-PTP inactivates Src family kinase downstream of the TCR, thereby contributing to the threshold of TCR activation[11]. Although both knockout experiments and small molecule inhibitors of these phosphatases have shown potent effect on lowering TCR threshold and increasing T cell activity, none of them have been used in CAR T therapy. A representative SHP1/2 inhibitor has the structure of

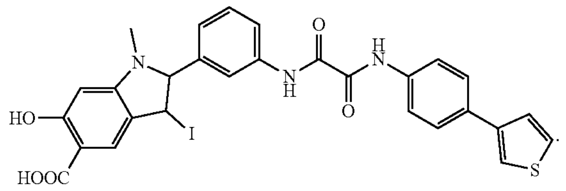

SHP1/2 inhibitor

Figure 7A:
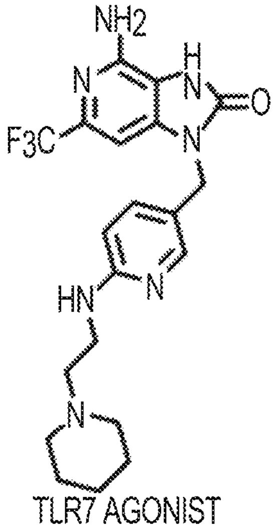
FIG. 7. Evaluation of TLR7 agonist and PTP1b inhibitor effect on rejuvenation of exhausted CAR T cells. (A) Chemical structure of TLR7 agonist and PTP1b inhibitor. (B-C) Exhausted CAR T cells were incubated with different concentrations of TLR7 agonist and PTP1b inhibitor monitored by lysis effect and $INF_\gamma$ (B) and expression level of PD-1 LAG-3 and Tim3 after incubation (C). * denotes a p-value<0.05, **<0.01, ns=not significant.
Figure 7A:
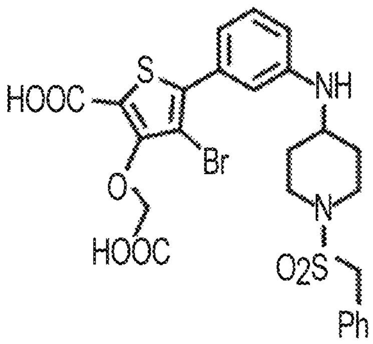
Figure 7B:
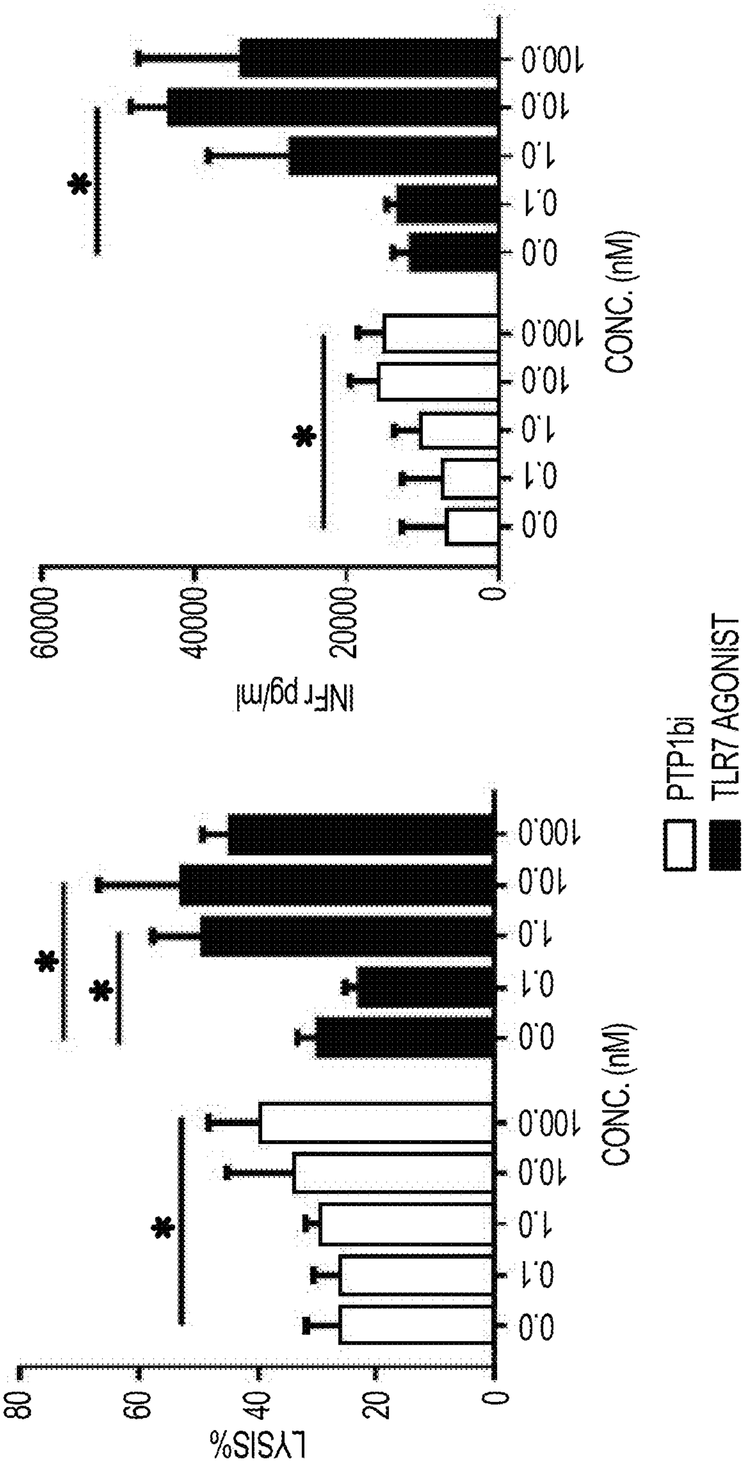
Figure 7C:
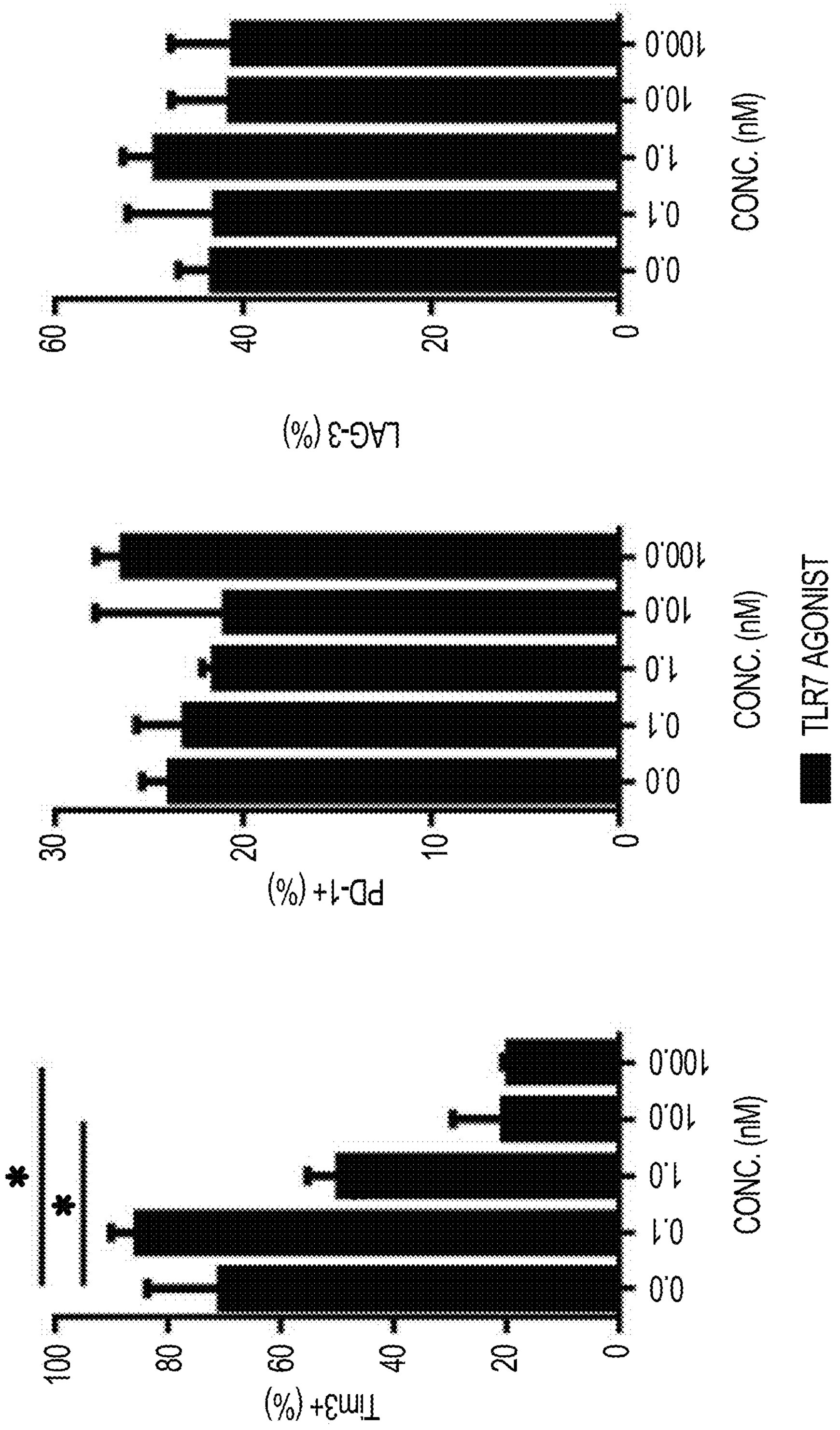
Figure 8A:
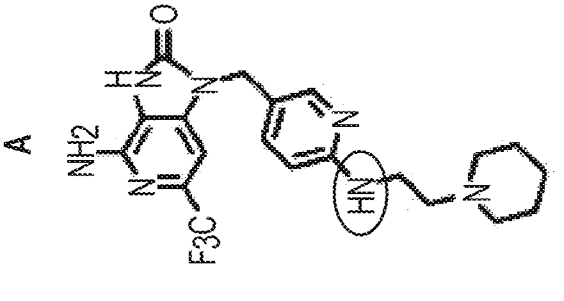
FIG. 8. Evaluation of potential derivatization sites of the TLR7 agonist for non-releasable ligand targeted delivery. (A) Chemical structure of the TLR7 agonist analogs. (B) Exhausted CAR T cells were incubated with different concentration of TLR7 analogs and lysis effect was measured and compared to non-treated group.
Figure 8A:
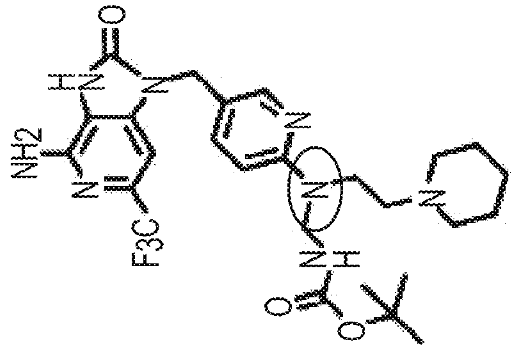
Figure 8A:
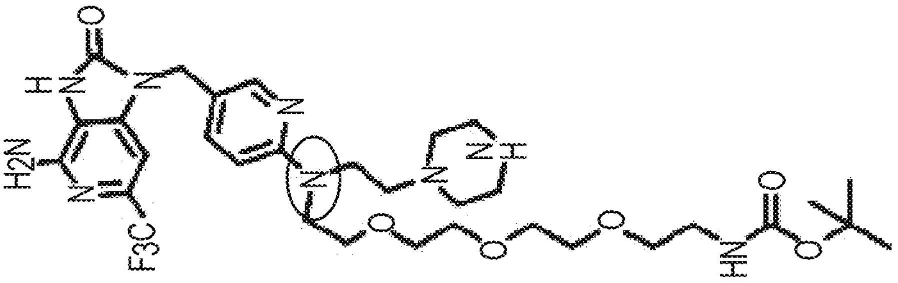
Figure 8A:
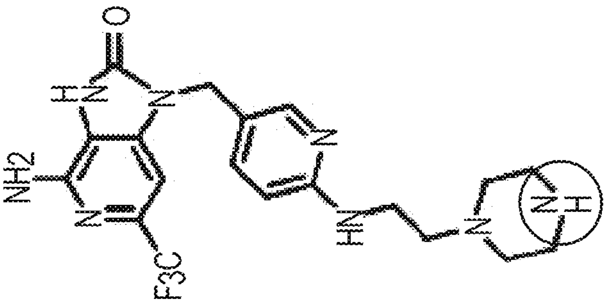
Figure 8A:
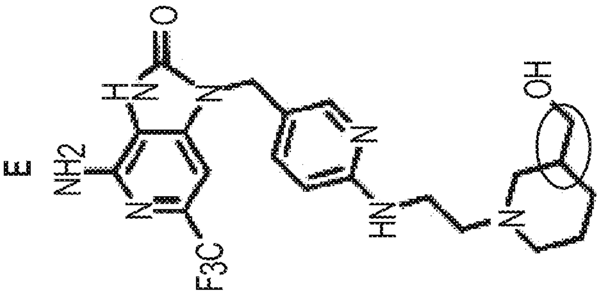
Figure 8B:
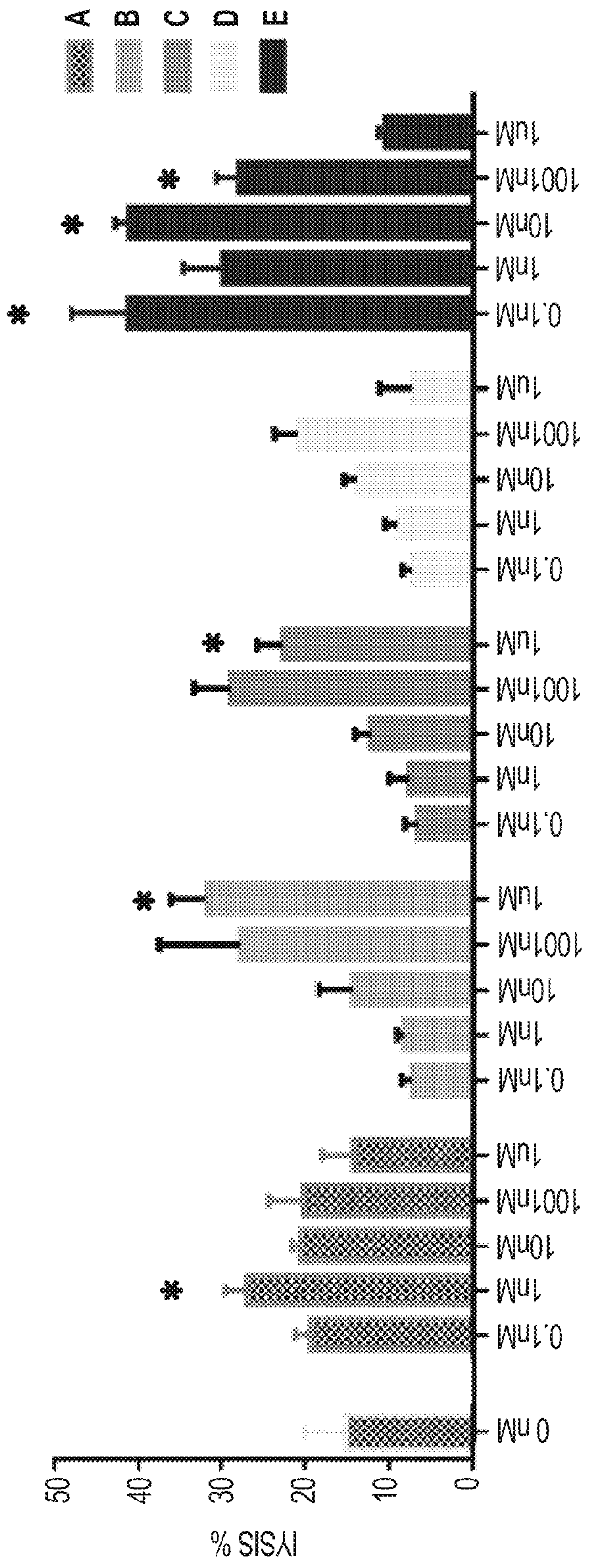
Figure 9A:
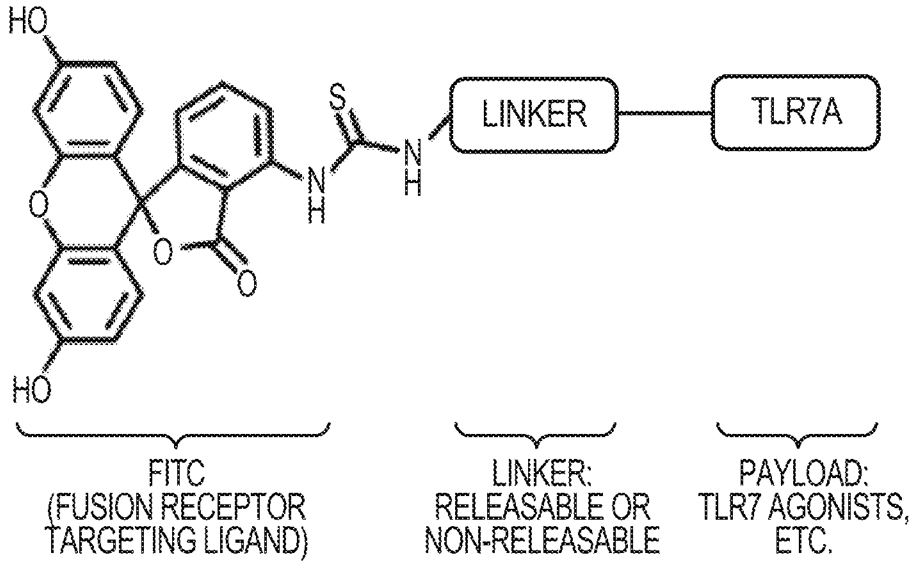
FIG. 9. Design and evaluation of releasable and non-releasable targeted delivery of TLR7 agonist using HIV as a targeting ligand. (A) Illustration of chemical structure of FITC-TLR7 agonist. (B) Exhausted CAR T cells were incubated with different concentration of releasable FITC-TLR7 and non-releasable FITC-JTLR7 agonists and lysis effect was measured and compared to non-treated group. *denotes a p-value<0.05, **<0.01, ns=not significant. (C) Left, crystal structure of FITC (green) binding with FITC scFv (grey) (PDB: 1X9Q, left), the distance between FITC to the edge of FTIC scFv is measured to be around 18 Å. Right, similarly, crystal structure of R-848 (red) binding with TLR7 (grey) (PDB:5GMF) is shown with distance between R-848 and the edge of TLR7 around 24 Å. (D) Diagram illustrating the two possible working mechanisms, "Reaching" or "Jumping" Mode, for the non-releasable FITC-TLR7 agonists.
Figure 9B:
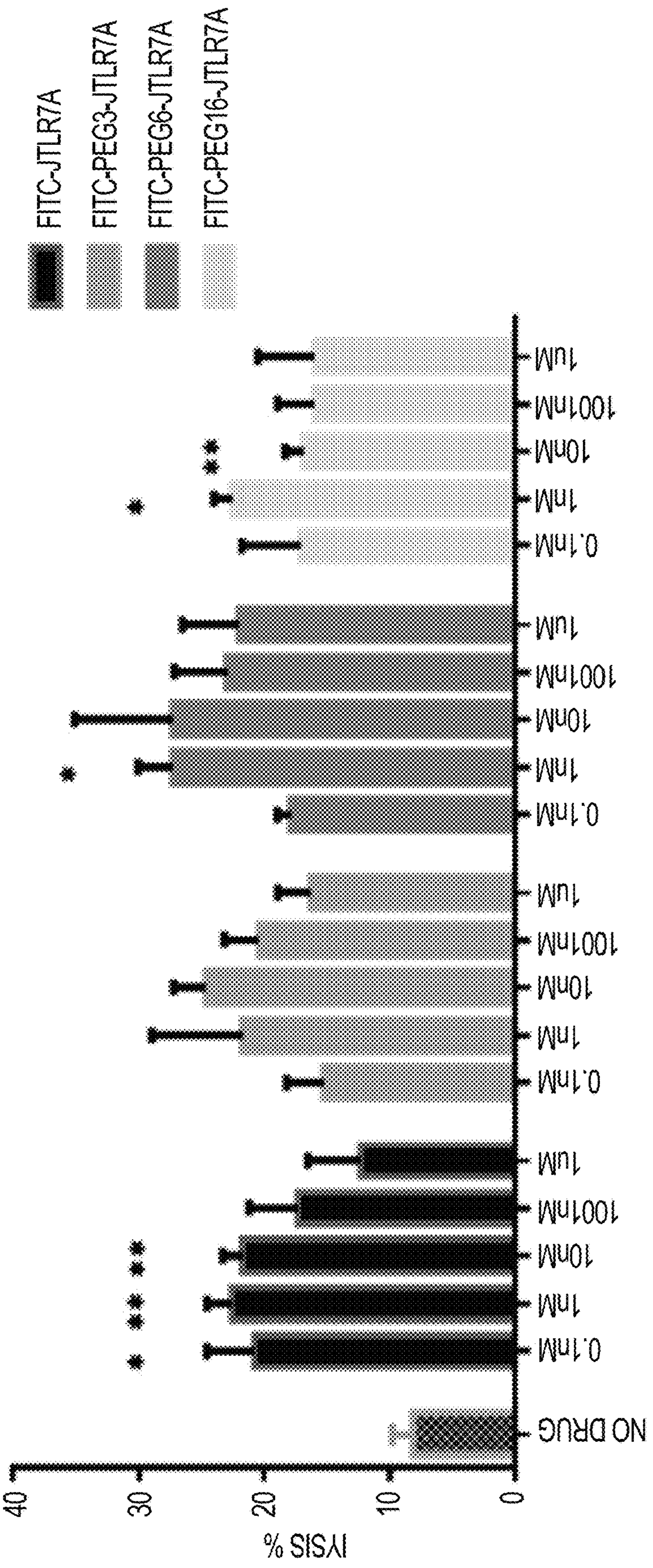
Figure 9C:
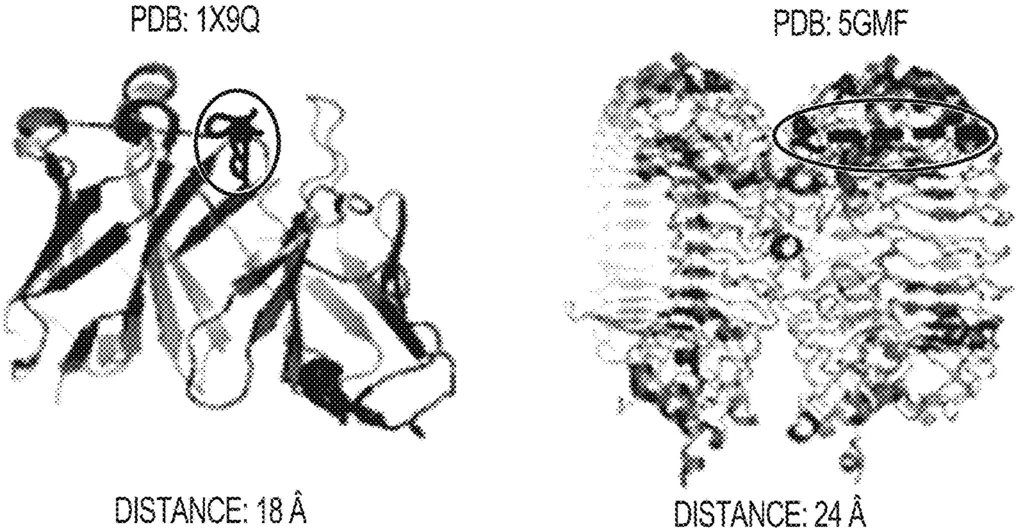
Figure 9D:
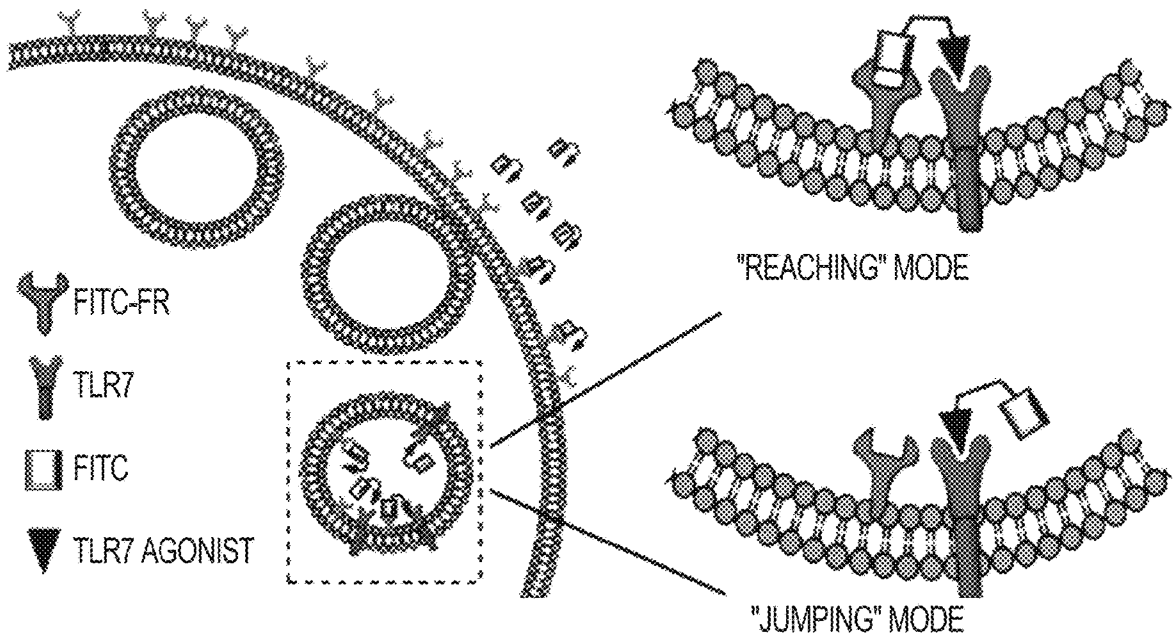
Figure 10:
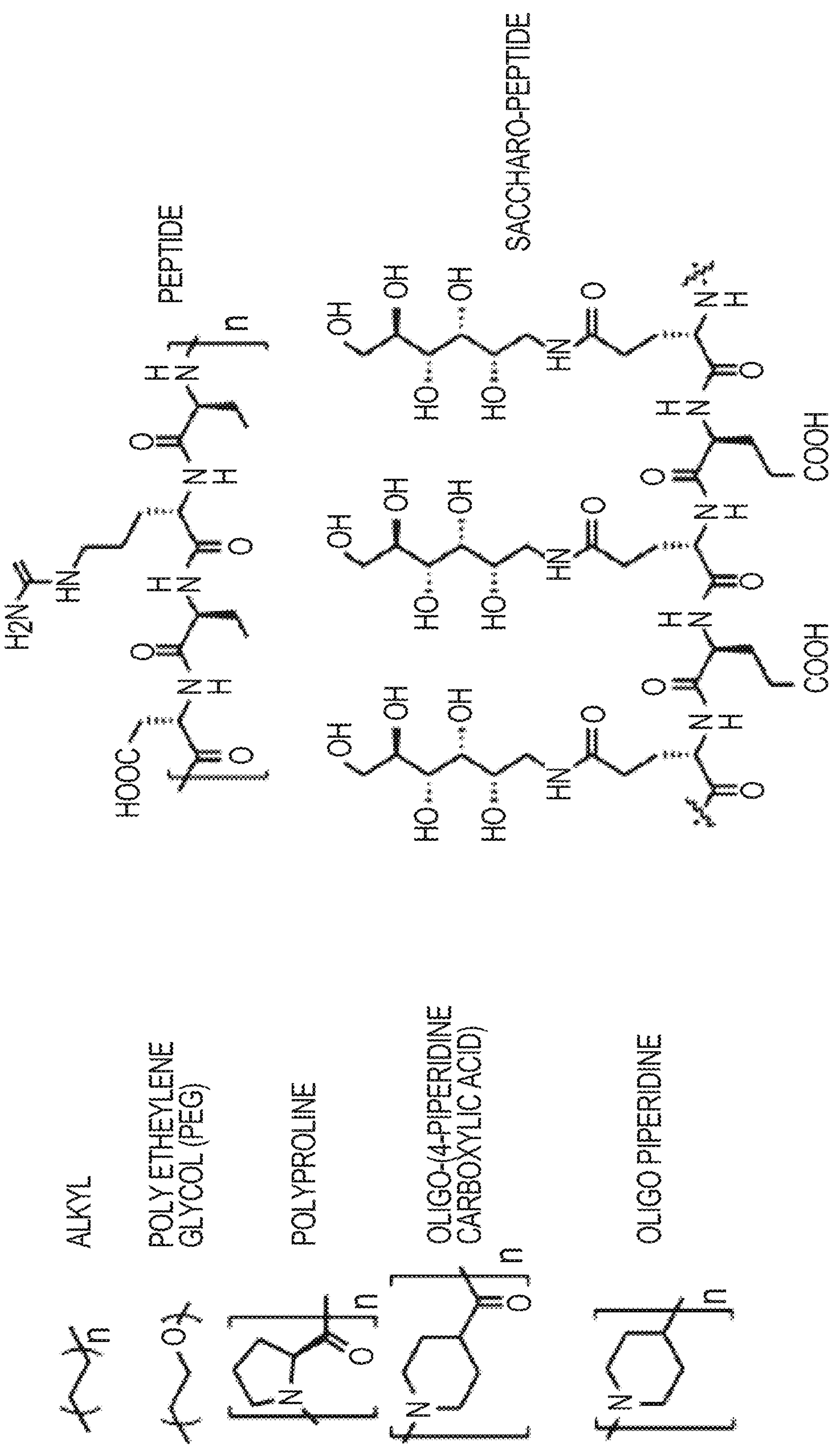
FIG. 10, Chemical linkers of variable rigidity and hydrophobicity available for usage in the design of targeting ligand-payload conjugates.

Another approach to rejuvenate the T cells is to augment their activity through the engagement of antigen independent innate immune receptors. It has been known that certain pathogen pattern recognition (PPR) receptors, including toll like receptors (TLR), do express on non-myeloid cell populations, including T cells, and can be activated in a similar way. Research has also shown that co-stimulation of TLR7/8 agonists and TCR signaling can activate CD8 T cells and increase $INF_{\gamma}$ secretion[13]. However, due to the strong side effects of systemic dosing of TLR agonists, none of these agonists have been used in CAR T therapy to reactivate the T cell or change the immunosuppressive microenvironment. The employment of TUR agonists for cancer immunotherapy is also hindered by the controversial effect of TLR agonists on the tumor cells. Therefore, a targeted delivery of the potential payloads to the CAR T cell is highly desired. A potent TLR7 agonist was found in the literature (FIG. 7A) which is around 40 fold stronger than the FDA approved imiquimod.

Figure 6B:
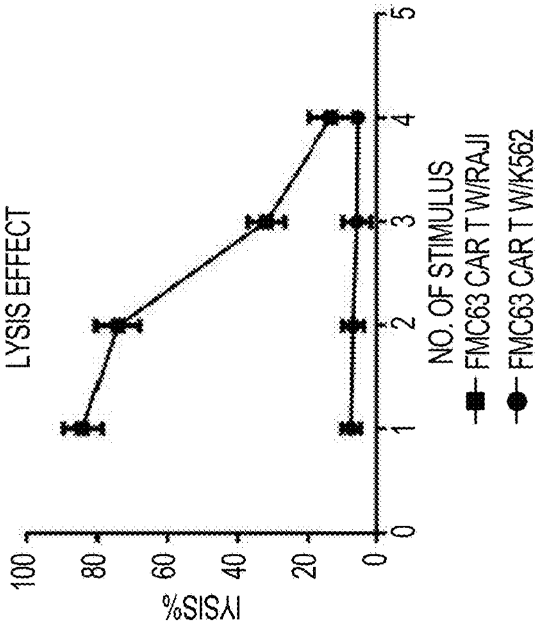
FIG. 6. in vitro model for the induction of CAR T cell exhaustion. (A) $CD19^+$ Raji and anti-CD19 CAR T cells were co-cultured at 1:1 ratio with fresh Raji cells added every 12 h. (B) Lysis effect of CART cells gradually decreased as the number of stimulus (number of Raji cell addition) increases. $CD19^-$K562 cells were used as control. (C) Expression level change of co-inhibitory molecules, PD-1, LAG3 and Tim3 for stim1 and stim3 in CD4 and CD8 positive CAR T cells.
Figure 6A:
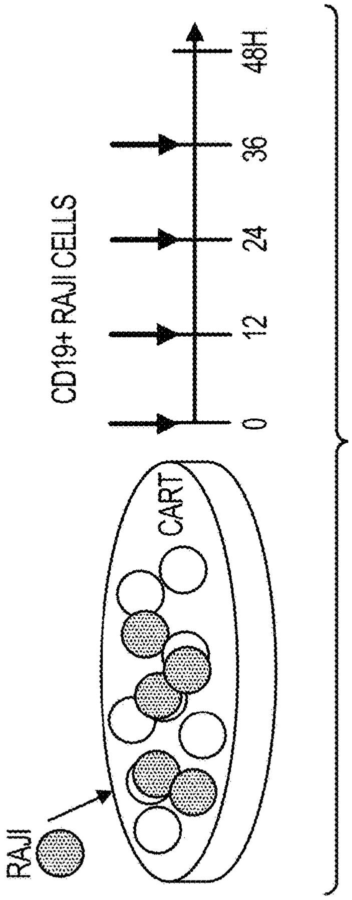
Figure 6C:
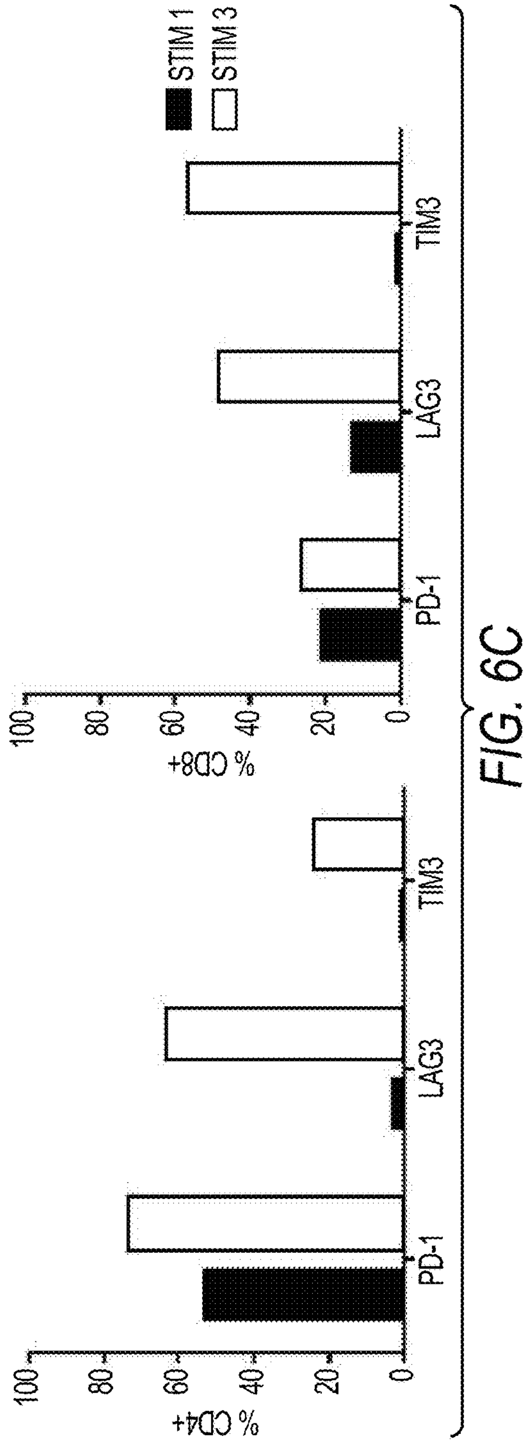

To set up an in vitro screening model, as shown in FIG. 6, anti-CD 19 CAR T cells were exposed to 4 rounds of addition of CD19 positive Raji cells, and became exhausted as marked by gradual decreased lysis activity as well as increased co-inhibitory markers in an in vitro co-culture model. It's worth noticing that the culture medium is important for the introduction of CAR T exhaustion and needs to be kept the same without new replenish or change during the whole process. It indicates that the soluble components that are released by cancer cells and/or CAR T cells into the medium, most likely immunosuppressive cytokines and modulators (adenosine etc.), play a pivotal role in this process. It also suggests that the exhaustion of CAR T cells generated by this in vitro model is at a rather pliable than irreversible status.

Treatment of the TLR7 agonist and PTP1b (highly homologous to TC-PTP[26]) inhibitor[27] of choice with the already exhausted CAR T cells was shown to be able to reactivate them compared to the no treatment group (FIG. 7). No significant changes, however, were observed in the expression level of co-inhibitory markers except for Tim3. As shown by FIG. 7C, the PTP1b inhibitor in general does not show as strong of a reactivation effect as the TLR7 agonist. Without being limited by any theory, this result could be due to the current in vitro screening model where "Reversion" rather than "Prevention" of exhaustion is studied, and the phosphatases are already "silenced" at the exhausted status, therefore their inhibition will have little to no effect. A modified screening model for a future study will test the effects of phosphatase inhibitors and other drugs with a focus on the "prevention" of exhaustion by adding the drugs at the beginning of all cultures and keeping the rest of the settings the same. In this way, it may be possible to see whether the inhibition of phosphatase can lower the tonic signaling of CAR T while still keeping a functional killing effect. We will mainly focus on TLR7 agonist for the following study.

Since TLR7 is one of the 4 TLR family members that resides inside the endosome, it is speculated that a non-releasable linker between the TLR7 agonist and our secret passageway targeting ligand would preserve its TLR7 agonist function[28]. To achieve that, several TLR7 agonist analogs were prepared and tested to find the proper derivatization sites for linkage. As shown in FIG. 8, the TLR7 agonist with a $CH_2OH$ extension at the piperidine ring has an even higher activity compared to the parent drug. Therefore, this derivative site will be used for a non-releasable conjugate. A disulfide bond linked self-immolative form also has been synthesized. In order to understand the distance needed for this TLR7 agonist to reach its own target, three different lengths of linker (PEG3, 6, 16) between the FITC and TLR7 agonist were made for the non-releasable FITC-TLR7. As shown in FIG. 9 C, all of the non-releasable forms had some effect, while the $PEG_6$ compound showed the best dose-dependent response. These results indicate that TLR7 agonists may dock with TLR7 either by reaching out while binding with FITC-FR or jumping between TLR and FITC-FR, under which conditions the length of the linker in between is not a crucial factor (FIG. 9 D-E). Since the non-releasable FITC-TLR7 is trapped inside the endosome and the volume of each endosome is much smaller than the cytosol, the intra-endosome TLR7 can get to its functional concentration much faster and quicker, resulting in a smaller $IC_{50}$.

Example 8. Other Potential Payloads for Revert/Prevent the Exhaustion of CAR T Cells Other than TLR7 agonist, there are several other potential payloads that may revert/prevent the exhaustion of CAR T cells as described below. Some of the targets may not have agonists or inhibitors with $IC_{50}$ suitable for our targeted drug delivery approach for now, but are still worth noticing and may be explored through other inhibitory mechanisms, such as CRISPR or targeted microRNA delivery approaches.

STING agonist

The Simulator of IFN Genes (STING) is a master adaptor involved in cytosolic DNA sensing and the following IFN-β production. STING associates weakly to sdDNA, but strongly binds the endogenous cyclic dinucleotide GMP-AMP (cGAMP) synthesized by the cGMP-AMP synthase (sGAS). It is predominantly expressed in macrophages, T cells, a variety of DCs, endothelial cells, and select fibroblasts and epithelial cells. Studies of STING have mainly focused on its function in macrophages and dendritic cells, and recently some groups have noticed the direct effect of STING activation in T cells[40]. It is possible that a STING agonist will have a similar pro-inflammatory effect on T cells. ADU-S100 is one of the many STING agonists that has been pursued in clinics.

DGK-α inhibitor

Diacylglycerol Kinase-α (DGK-α) converts diacylglycerol (DAG), a second messenger in TCR signaling together with IP3, to phosphatidic acid (PA). DGK is more highly expressed in CD8TIL than in CD8-NIL, and its inhibition promotes ERK phosphorylation and lytic degranulation[41]; it also restores lytic functions of CAR TIL that are isolated from in vivo[5]. Some DGK inhibitor structures are as following;

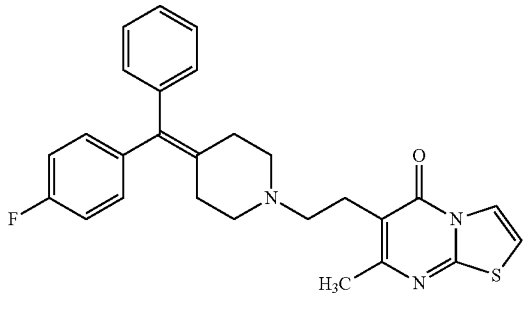

DKG I inhibitor

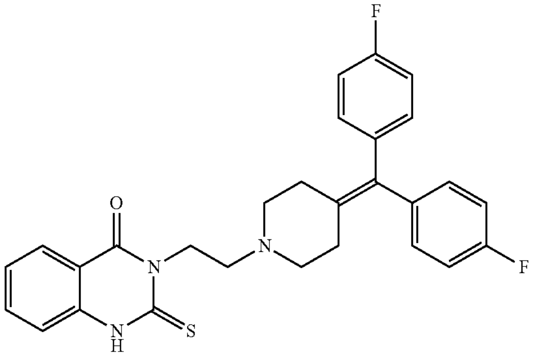

DKG II inhibitor

TGFβRI (ALK5) inhibitor

TGFβ is known for its immunosuppressive function in many immune cells, such as the T cell, B cell, and macrophages. The blockage of TGFβ type I receptor (TGFβRI, also called ALK5) in T cells reverts the immunosuppressive environment of the tumor[42]. Small molecule inhibitors have been pursued with galunisertib (LY2157299 monohydrate) and EW-7197 tested in clinics[43-44].

A TGFβ inhibitor structure is as following:

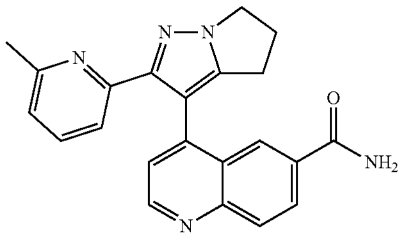

TGFβ inhibitor (LY2157299)

EZH2 inhibitor

Enhancer of Zeste Homolog 2 (EZH2) is a histone H3K27 methyltransferase with a strong correv the Treg function. Genetic or pharmacological disruption of EZH2 drove acquisition of proinflammatory function of tumor infiltrating Treg[45]. Since exhausted CTL in chronic virus infections is also characterized by unique epigenetic changes[174], it is possible that EZH2 inhibitors will be able to reverse this exhaustion status. Several small molecules of EZH2 inhibitors have been developed, including CPI1205, EPZ6438 and GSK126.

Therefore, the FITC-FR fusion receptor and the corresponding FITC targeted immune-agonists payloads provide a universal platform for the monitor and control of CAR T cells homing and persistence in solid tumor. This approach can be easily incorporated into CAR T cells for any antigen since the FITC-FR fusion receptor is independently expressed to the CAR construct. The modular design of targeting ligand-payload conjugates also makes it easier for the switching and modification. This approach combines the benefits of cell therapy and small molecule-based targeted drug delivery and may require extra characterization of both the engineered cells and the corresponding ligands.

The success of CAR T cells in solid tumor most likely requires the combination of multiple approaches targeting other players within the microenvironment as well, such as breaking down of the extracellular matrix by PI3K kinase inhibitors, reprograming of anti-inflammatory M2 macrophages to a proinflammatory M1 phenotype, and upregulation of the decreased MHC molecules level on cancer cells. Therefore, more and more combinational therapy studies will be conducted both preclinically and clinically. However, at the same time, a careful examination and control of the CAR T cell itself cannot be neglected and should be optimized by using simple but robust systems like FITC-FR fusion receptors in preclinical research first before it reaches to humans.

REFERENCES

1. Park, J. H.; Riviere, I.; Gonen, M.; Wang, X.; Senechal, B.; Curran, K. J.; Sauter, C.; Wang, Y.; Santomasso, B.; Mead, E.; Roshal, M.; Maslak, P.; Davila, M.; Brentjens, R. J.; Sadelain, M., Long-Term Follow-up of CD19 CAR Therapy in Acute Lymphoblastic Leukemia. The New England journal of medicine 2018, 378 (5), 449-459.
2. Jiang, Y.; Li, Y.; Zhu, B., T-cell exhaustion in the tumor microenvironment. Cell Death Dis 2015, 6, e1792.
3. Matsuzaki, J.; Gnjatic, S.; Mhawech-Fauceglia, P.; Beck, A.; Miller, A.; Tsuji, T.; Eppolito, C.; Qian, F.; Lele, S.; Shrikant, P.; Old, L. J.; Odunsi, K., Tumor-infiltrating NY-ESO-1-specific CD8+ T cells are negatively regulated by LAG-3 and PD-1 in human ovarian cancer. Proceedings of the National Academy of Sciences of the United States of America 2010. 107 (17), 7875-80.
4. Moon, E. K.; Ranganathan, K.; Eruslanov, E.; Kim, S.; Newick, K.; O'Brien, S.; Lo, A.; Liu, X.; Zhao, Y.; Albelda, S. M., Blockade of Programmed Death 1 Augments the Ability of Human T Cells Engineered to Target NY-ESO-1 to Control Tumor Growth after Adoptive Transfer. Clinical cancer research: an official journal of the American Association for Cancer Research 2016, 22 (2), 436-47.
5. Moon, E. K.; Wang, L. C.; Dolfi, D. V.; Wilson, C. B.; Ranganathan, K.; Sun, J.; Kapoor, V.; Scholler, J.; Pure, E.; Milone, M. C.; June, C. H.; Riley, J. L.; Wherry, E. J,; Albelda, S. M., Multifactorial T-cell hypofunction that is reversible can limit the efficacy of chimeric antigen receptor-transduced human T cells in solid tumors. Clinical cancer research: an official journal of the American Association for Cancer Research 2014, 20 (16), 4262-73.
6. Chae, Y. K.; Arya, A.; Iams, W.; Cruz, M. R.; Chandra, S.; Choi. J.; Giles, F., Current landscape and future of dual anti-CTLA4 and PD-1/PD-L1 blockade immunotherapy in cancer; lessons learned from clinical trials with melanoma and non-small cell lung cancer (NSCLC). J Immunother Cancer 2018, 6 (1), 39.
7. Ott, P. A.; Hodi, F. S.; Kaufman, H. L.; Wigginton, J. M.; Wolchok, J. D., Combination immunotherapy: a road map. J Immunother Cancer 2017, 5, 16.
8. Watson, H. A.; Dolton, G.; Ohme, J.; Ladell, K.; Vigar, M.; Wehenkel, S.; Hindley, J.; Mohammed, R. N.; Miners, K.; Luckwell, R. A.; Price, D. A.; Matthews, R. J.; Ager, A., Purity of transferred CD8(+) T cells is crucial for safety and efficacy of combinatorial tumor immunotherapy in the absence of SHP-1. Immunology and cell biology 2016, 94 (8), 802-8.
9. Wiede, F.; Shields, B. J.; Chew, S. H.; Kyparissoudis, K.; van Vliet, C.; Galic, S.; Tremblay, M. L.; Russell, S. M.; Godfrey, D. I.; Tiganis, T., T cell protein tyrosine phosphatase attenuates T cell signaling to maintain tolerance in mice. The Journal of clinical investigation 2011, 121 (12), 4758-74.
10. Prinz, P. U.; Mendler, A. N.; Masouris, I.; Durner, L.; Oberneder, R.; Noessner, E., High DGK-alpha and disabled MAPK pathways cause dysfunction of human tumor-infiltrating CD8+ T cells that is reversible by pharmacologic intervention. Journal of immunology 2012, 188 (12), 5990-6000.
11. Chua, B. Y.; Olson, M. R.; Bedoui, S.; Sekiya, T.; Wong, C. Y.; Turner, S. J.; Jackson, D. C., The use of a TLR2 agonist-based adjuvant for enhancing effector and memory CD8 T-cell responses. Immunology and cell biology 2014, 92 (4), 377-83.
12. Rhee, E. G.; Kelley, R. P.; Agarwal, I.; Lynch, D. M.; La Porte, A.; Simmons, N. L.; Clark, S. L.; Barouch, D. H., TLR4 ligands augment antigen-specific CD8+ T lymphocyte responses elicited by a viral vaccine vector. Journal of virology 2010, 84 (19), 10413-9.
13. Wiedemann, G. M.; Jacobi, S. J.; Chaloupka, M.; Krachan, A.; Hamm, S.; Strobl, S.; Baumgartner, R.; Rothenfusser, S.; Duewell, P.; Endres, S.; Kobold, S., A novel TLR7 agonist reverses NK cell anergy and cures RMA-S lymphoma-bearing mice. Oncoimmunology 2016, 5 (7), e1189051.
14. Cheadle, E. J.; Lipowska-Bhalla., G.; Dovedi, S. J.; Fagnano, E.; Klein, C.; Honeychurch, J.; Illidge, T. M., A TLR7 agonist enhances the antitumor efficacy of obinutuzumab in murine lymphoma models via NK cells and CD4 T cells. Leukemia 2017, 31 (10), 2278.
15. Hengge, U. R.; Ruzicka, T., Topical immunomodulation in dermatology: potential of toll-like receptor agonists. Dermatol Surg 2004, 30 (8), 1101-12.
16. Kaczanowska, S.; Joseph, A. M.; Davila, E., TLR agonists: our best frenemy in cancer immunotherapy. Journal of leukocyte biology 2013, 93 (6), 847-63.
17. Bandara, N. A.; Hansen, M. J.; Low, P. S., Effect of receptor occupancy on folate receptor internalization. Molecular pharmaceutics 2014, 11 (3), 1007-13.
18. Kniess, T.; Laube, M.; Wust, F.; Pietzsch, J., Technetium-99m based small molecule radiopharmaceuticals and radiotracers targeting inflammation and infection. *Dalton transactions* 2017, 46 (42), 14435-14451.
19. Kularatne, S. A.; Zhou, Z.; Yang, J.; Post, C. B.; Low, P. S., Design, synthesis, and preclinical evaluation of prostate-specific membrane antigen targeted (99m)Tc-radioimaging agents. *Molecular pharmaceutics* 2009, 6 (3), 790-800.
20. Henne, W. A.; Rothenbuhler, R.; Ayala-Lopez, W.; Kia, W.; Varghese, B.; Low, P. S., Imaging sites of infection using a 99mTc-labeled folate conjugate targeted to folate receptor positive macrophages. *Molecular pharmaceutics* 2012, 9 (5), 1435-40.

21. Kahan, S. M.; Wherry, E. J.; Zajac, A. J., T cell exhaustion during persistent viral infections. *Virology* 2015, 479-480, 180-93.

22. Stefanova, I.; Hemmer, B.; Vergelli, M.; Martin, R.; Biddison, W. E.; Germain, R. N., TCR ligand discrimination is enforced by competing ERK positive and SHP-1 negative feedback pathways. *Nature immunology* 2003, 4 (3), 248-54.

23. Lorenz, U., SHP-1 and SHP-2 in T cells: two phosphatases functioning at many *Immunological reviews* 2009, 228 (1), 342-59.

24. Watson, H. A.; Wehenkel, S.; Matthews, J.; Ager, A., SHP-1: the next checkpoint target for cancer immunotherapy? *Biochemical Society transactions* 2016, 44 (2), 356-62.

25. Hebeisen, M.; Baitsch, L.; Presotto, D.; Baumgaertner, P.; Romero, P.; Michielin, O.; Speiser, D. E.; Rufer, N., SHP-1 phosphatase activity counteracts increased T cell receptor affinity. *The Journal of clinical investigation* 2013, 123 (3), 1044-56.

26. Wiede, F.; Shields, B. J.; Chew, S. H.; Kyparissoudis, K.; van Vliet, C.; Galic, S.; Tremblay, M. L.; Russell, S. M.; Godfrey, D. I.; Tiganis, T., T cell protein tyrosine phosphatase attenuates T cell signaling to maintain tolerance in mice. *The Journal of clinical investigation* 2011, 121 (12), 4758-74.

27. Pike, K. A.; Hatzihristidis, T.; Bussieres-Marmen, S.; Robert, F.; Desai, N.; Miranda-Saavedra, D.; Pelletier, J.; Tremblay, M. L., TC-PTP regulates the IL-7 transcriptional response during murine early T cell development. *Scientific reports* 2017, 7 (1), 13275.

28. Wiedemann, G. M.; Jacobi, S. J.; Chaloupka, M.; Krachan, A.; Hamm, S.; Strobl, S.; Baumgartner, R.; Rothenfusser, S.; Duewell, P.; Endres, S.; Kobold, S., A novel TLR7 agonist reverses NK cell allergy and cures RMA-S lymphoma-bearing mice. *Oncoimmunology* 2016, 5 (7), e1189051.

29. Caron, G.; Duluc, D.; Fremaux, I.; Jeannin, P.; David, C.; Gascan, H.; Delneste, Y., Direct stimulation of human T cells via TLR5 and TLR7/8: flagellin and R-848 up-regulate proliferation and IFN-gamma production by memory CD4+ cells. *Journal of immunology* 2005, 175 (3), 1551-7.

30. Wille-Reece, U.; Flynn, B. J.; Lore, K.; Koup, R. A.; Miles, A. P.; Saul, A.; Kedl, R. M.; Mattapallil, J. J.; Weiss, W. R.; Roederer, M.; Seder, R. A., Toll-like receptor agonists influence the magnitude and quality of memory T cell responses after prime-boost immunization in nonhuman primates. *The Journal of experimental medicine* 2006, 203 (5), 1249-58.

31. Zarember, K. A.; Godowski, P. J., Tissue expression of human Toll-like receptors and differential regulation of Toll-like receptor mRNAs in leukocytes in response to microbes, their products, and cytokines. *Journal of immunology* 2002, 168 (2), 554-61.

32. Hornung, V.; Rothenfusser, S.; Britsch, S.; Krug, A.; Jahrsdorfer, B.; Giese, T.; Endres, S.; Hartmann, G., Quantitative expression of toll-like receptor 1-10 mRNA in cellular subsets of human peripheral blood mononuclear cells and sensitivity to CpG oligodeoxynucleotides. *Journal of immunology* 2002, 168 (9), 4531-7.

33. Strominger, N. L.; Brady, R.; Gullikson, G.; Carpenter, D. O., Imiquimod-elicited emesis is mediated by the area postrema, but not by direct neuronal activation. *Brain Res Bull* 2001, 55 (3), 445-51.

34. Harrison, L. I.; Astry, C.; Kumar, S.; Yunis, C., Pharmacokinetics of 852A, an imidazoquinoline Toll-like receptor 7-specific agonist, following intravenous, subcutaneous, and oral administrations in humans. *Journal of clinical pharmacology* 2007, 47 (8), 962-9.

35. Dudek, A. Z.; Yunis, C.; Harrison, L. I.; Kumar, S.; Hawkinson, R.; Cooley, S.; Vasilakos, J. P.; Gorski, K. S.; Miller, J. S., First in human phase I trial of 852A, a novel systemic toll-like receptor 7 agonist, to activate innate immune responses in patients with advanced cancer. *Clinical cancer research: an official journal of the American Association for Cancer Research* 2007, 13 (23), 7119-25.

36. Dummer, R.; Hauschild, A.; Becker, J. C.; Grob, J. J.; Schadendorf, D.; Tebbs, V.; Skalsky, J.; Kaehler, K. C.; Moosbauer, S.; Clark, R.; Meng, T. C.; Urosevic, M., An exploratory study of systemic administration of the toll-like receptor-7 agonist 852A in patients with refractory metastatic melanoma. *Clinical cancer research: an official journal of the American Association or Cancer Research* 2008, 14 (3), 856-64.

37. Perkins, H; Khodai, T.; Mechiche, Colman, P.; Burden, F.; Laxton, C.; Horscroft, N.; Corey, T.; Rodrigues, D.; Rawal, J.; Heyen, J.; Fidock, M.; Westby, M.; Bright, H., Therapy with TLR7 agonists induces lymphopenia: correlating pharmacology to mechanism in a mouse model. *J Clin Immunol* 2012, 32 (5), 1082-92.

38. Hasham, M. G.; Baxan, N.; Stuckey, D. J.; Branca, J.; Perkins, B.; Dent, O.; Duffy, T.; Hameed, T. S.; Stella, S. E.; Bellahcene, M.; Schneider, M. D.; Harding, S. E.; Rosenthal, N.; Sattler, S., Systemic autoimmunity induced by the TLR7/8 agonist Resiquimod causes myocarditis and dilated cardiomyopathy in a new mouse model of autoimmune heart disease. *Dis Model Mech* 2017, 10 (3), 259-270.

39. Katie, J.; David, N., The discovery of a novel prototype small molecule TLR7 agonist for the treatment of hepatitis C virus infection. *MedChemComm* 2011, 2 (3), 185-189.

40. Jones, P.; Pryde, D. C.; Tran, T. D.; Adam, F. M.; Bish, G.; Cabo, F.; Ciaramella, G.; Dixon, R.; Duckworth, J.; Fox, D. N.; Hay, D. A.; Hitchin, J.; Horscroft, N.; Howard, M.; Laxton, C.; Parkinson, T.; Parsons, G.; Proctor, K.; Smith, M. C.; Smith, N.; Thomas, A., Discovery of a highly potent series of TLR7 agonists. *Bioorganic & medicinal chemistry letters* 2011, 21 (19), 5939-43.

41. Hemmi, H.; Kaisho, T.; Takeuchi, O.; Sato, S.; Sanjo, H.; Hoshino, K.; Horiuchi, T.; Tomizawa, H.; Takeda, K.; Akira, S., Small anti-viral compounds activate immune cells via the TLR7 MyD88-dependent signaling pathway. *Nature immunology* 2002, 3 (2), 196-200.

42. Iversen, L. F.; Moller, K. B.; Pedersen, A. K.; Peters, G. H.; Petersen, A. S.; Andersen, H. S.; Branner, S.; Mortensen, S. B.; Moller, N. P., Structure determination of T cell protein-tyrosine phosphatase. *The Journal of biological chemistry* 2002, 277 (22), 19982-90.

43. Wilson, D. P.; Wan, Z. K.; Xu, W. X.; Kirincich, S. J.; Follows, B. C.; Joseph-McCarthy, D.; Foreman, K.; Moretto, A.; Wu, J.; Zhu, M.; Binnun, E.; Zhang, Y. L.; Tam, M.; Erbe, D. V.; Tobin, J.; Xu, X.; Leung, L.; Shilling, A.; Tam, S. Y.; Mansour, T. S.; Lee, J., Structure-based optimization of protein tyrosine phosphatase 1B inhibitors: from the active site to the second phosphotyrosine binding site. *Journal of medicinal chemistry* 2007, 50 (19), 4681-98.

44. Ignacio, B. J.; Albin, T. J.; Esser-Kahn, A. P.; Verdoes, M., Toll-like Receptor Agonist Conjugation; A Chemical Perspective. *Bioconjugate chemistry* 2018, 29 (3), 587-603.

45. Parente-Pereira, A. C.; Burnet, J.; Ellison, D.; Foster, J.; Davies, D. M.; van der Stegen, S.; Burbridge, S.; Chiapero-Stanke, L.; Wilkie, S.; Mather, S.; Maher, J., Trafficking of CAR-engineered human T cells following regional or systemic adoptive transfer in SCID beige mice. *J Clin Immunol* 2011, 31 (4), 710-8.

46. Dobrenkov, K.; Olszewska, M.; Likar, Y.; Shenker, L.; Gunset, G.; Cai, S.; Pillarsetty, N.; Hricak, H.; Sadelain, M.; Ponomarev, V., Monitoring the efficacy of adoptively transferred prostate cancer-targeted human T lymphocytes with PET and bioluminescence imaging. *Journal of nuclear medicine: official publication, Society of Nuclear Medicine* 2008, 49 (7), 1162-70.
47. Emami-Shahri, N.; Foster, J.; Kashani, R.; Gazinska, P.; Cook, C.; Sosabowski, J.; Maher, I.; Papa, S., Clinically compliant spatial and temporal imaging: of chimeric antigen receptor T-cells. *Nature communications* 2018, 9 (1), 1081.
48. Bruno, R.; Giannasio, P.; Ronga, Baudin, E.; Travagli, J. P.; Russo, D.; Filetti, S.; Schlumberger, M., Sodium iodide symporter expression and radioiodine distribution in extrathyroidal tissues. *J Endocrinol Invest* 2004, 27 (11), 1010-4.
49. Vedvyas, Y.; Shevlin, E.; Zamam, M.; Min, I. M.; Amor-Coarasa, A.; Park, S.; Park, S.; Kwon, K. W.; Smith, T.; Luo, Y.; Kim, D.; Kim, Y.; Law, B.; Ting, R.; Babich, J.; Jin, M. M., Longitudinal PET imaging demonstrates biphasic CAR T cell responses in survivors. *JCI insight* 2016, 1 (19), e90064.
50. Zhang, H.; Moroz, M. A.; Serganova, I.; Ku, T.; Huang, R.; Vider, J,; Maecke, H. R.; Larson, S. M.; Blasberg, R.; Smith-Jones, P. M., Imaging expression of the human somatostatin receptor subtype-2 reporter gene with 68Ga-DOTATOC. *Journal of nuclear medicine: official publication, Society of Nuclear Medicine* 2011, 52 (1), 123-31.
51. Bhattacharyya, S.; Dixit, M., Metallic radionuclides in the development of diagnostic and therapeutic radiopharmaceuticals. *Dalton transactions* 2011, 40 (23), 6112-28.
52. Khan, O.; Giles, J. R.; McDonald, S.; Mamie, S.; Ngiow, S. F.: Patel, K. P.; Werner, M. T.; Huang, A. C.; Alexander, K. A.; Wu, J. E.; Attanasio, J.; Yan, P.; George, S. M,; Bengsch, B.; Staupe, R. P.; Donahue, G.; Xu, W.; Amaravadi, R. K.; Xu, X.; Karakousis, G. C.; Mitchell, T. C.; Schuchter, L. M.; Kaye, J.; Berger, S. L.; Wherry, E, J., TOX transcriptionally and epigenetically programs CD8(+) T cell exhaustion. *Nature* 2019.
53. Alfei, F.; Kanev, K.; Hofmann, M.; Wu, M.; Ghoneim, H. E.; Roelli, P.; Utzschneider, D. T.; von Hoesslin, M.; Cullen, J. G.; Fan, Y.; Eisenberg, V.; Wohlleber, D.; Steiger, K.; Merkler, D.; Delorenzi, M.; Knolle, P. A.; Cohen, C. J.; Thimme, R.; Youngblood, B.; Zehn, D., TOX reinforces the phenotype and longevity of exhausted T cells in chronic viral infection. *Nature* 2019.
54. Kawai, T.; Akira, S., Signaling to NF-kappaB by Toll-like receptors. *Trends in molecular medicine* 2007, 13 (11), 460-9.
55. Chen, J.; Lopez-Moyado, I. F.; Seo, H.; Lio, C. J.; Hempleman, L. J.; Sekiya, T.; Yoshimura, A.; Scott-Browne, J. P.; Rao, A., NR4A transcription factors limit CAR T cell function in solid tumours. *Nature* 2019, 567 (7749), 530-534.
56. Larkin, B.; Ilyukha, V.; Sorokin, M.; Buzdin, A.; Vannier, E.; Poltorak, A., Cutting Edge: Activation of STING in T Cells Induces Type 1 IFN Responses and Cell Death. *Journal of immunology* 2017, 199 (2), 397-402.
57. Prinz, P. U.; Mendler, A. N.; Masouris, I.; Durner, L.; Oberneder, R.; Noessner, E., High DGK-alpha and disabled MAPK pathways cause dysfunction of human tumor-infiltrating CD8+ T cells that is reversible by pharmacologic intervention. *Journal of immunology* 2012, 188 (12), 5990-6000.
58. Gorelik, L.; Flavell, R. A., Immune-mediated eradication of tumors through the blockade of transforming growth factor-β signaling in T cells. *Nature medicine* 2001, 7 (10), 1118.
59. Herbertz, S.; Sawyer, J. S.; Stauber, A. J.; Gueorguieva, I.; Driscoll, K. E.; Estrem, S. T.; Cleverly, A. L.; Desaiah, D.; Guba, S. C.; Benhadji, K. A.; Slapak, C. A.; Lahn, M. M., Clinical development of galunisertib (LY2157299 monohydrate), a small molecule inhibitor of transforming growth factor-beta signaling pathway. *Drug design, development and therapy* 2015, 9, 4479-99,
60. Jin, C. H.; Krishnaiah, M.; Sreenu, D.; Subrahmanyam, V. B.; Rao, K. S.; Lee, H. J.; Park, S. J.; Park, H. J.; Lee, K.; Sheen, Y. Y.; Kim, D. K., Discovery of N-((4-([1,2,4]triazolo[1,5-a]pyridin-6-yl)-5-(6-methylpyridin-2-yl)-1H-imidazol-2-yl)methyl)-2-fluoroaniline (EW-7197): a highly potent, selective, and orally bioavailable inhibitor of TGF-beta type 1 receptor kinase as cancer immunotherapeutic/antifibrotic agent. *Journal of medicinal chemistry* 2014, 57 (10), 4213-38.
61. Wang, D.; Quiros, J.; Mahuron, K.; Pai, C. C.; Ranzani, V.; Young, A.; Silveria, S.; Hardin, T.; Abnousian, A.; Pagani, M.; Rosenblum, M. D.; Van Gool, F.; Fong, L.; Bluestone, J. A.; DuPage, M., Targeting EZH2 Reprograms Intratumoral Regulators T Cells to Enhance Cancer Immunity. *Cell reports* 2018, 23 (11), 3262-3274

What is claimed is:

1. A system to rejuvenate an exhausted classical CAR T cell comprising at least two components:

a first component that is a conjugate comprising a targeting ligand covalently linked to a payload drug; and a second component that is a targeting ligand binding module linked to a membrane-anchoring module, wherein:

the payload drug is a Toll Like Receptor 7 (TLR7) agonist, the targeting ligand and the targeting ligand binding molecule are fluorescein isothiocyanate (FITC) and an anti-FITC antibody or fragment thereof, respectively; or tacrolimus (FK506) and FK506-binding protein (FKBP), respectively, the membrane-anchoring module is a folate receptor, the targeting ligand binding module of the second component recognizes the targeting ligand in the first component with high affinity to form a complex, the payload drug re-activates the CAR T cell through an antigen-independent pathway, and the membrane-anchoring module mediates internalization of the at least two components complex into the exhausted classical CAR T cell.

2. The system according to claim 1, wherein the membrane-anchoring module is a folate receptor alpha (FRα).

3. The system according to claim 1, wherein the first component comprises a releasable linker between the targeting ligand and the payload drug.

4. The system according to claim 1, wherein the first component comprises a non-releasable linker between the targeting ligand and the payload drug.

5. The system according to claim 1, wherein the binding affinity between the targeting ligand and the ligand-binding module is in a sub-nanomolar range.

6. The system according to claim 1, wherein the TLR7 agonist has the structure of

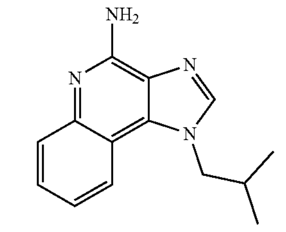
,
Imiquimod
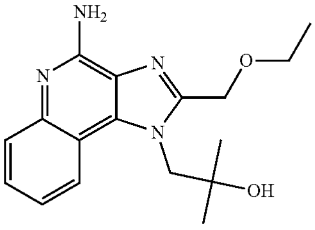
,
Resiquimod
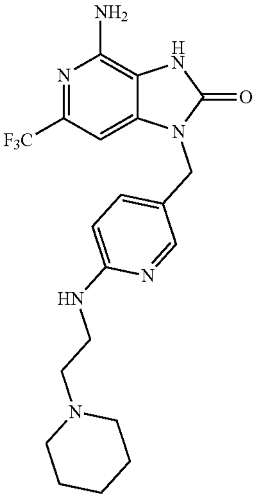
or
TLR7 agonist
-continued
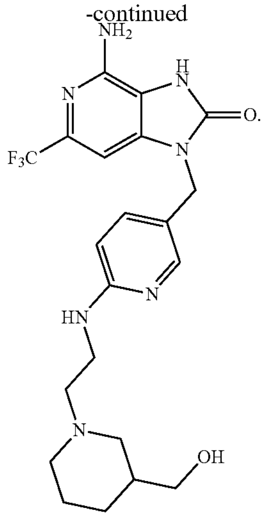
JTLR7
7. The system according to claim 1, wherein targeting ligand and the targeting ligand binding molecule are fluorescein isothiocyanate (FITC) and an anti-FITC antibody or fragment thereof, respectively, and the first component is a fluorescein isothiocyanate-TLR7 agonist having the structure:
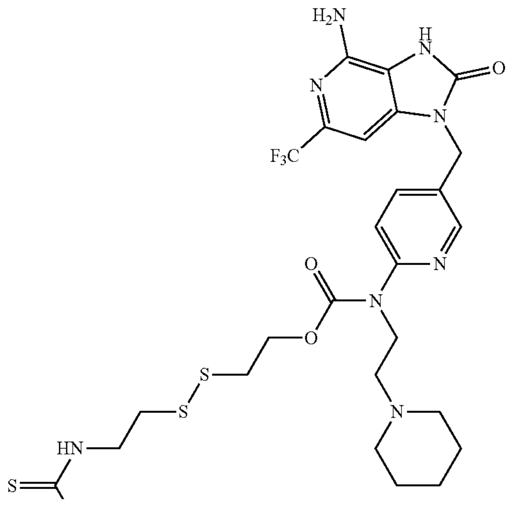

-continued
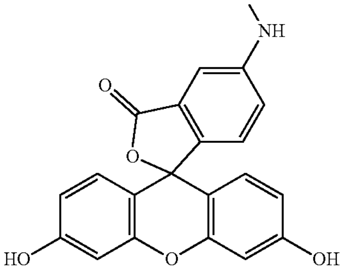
or
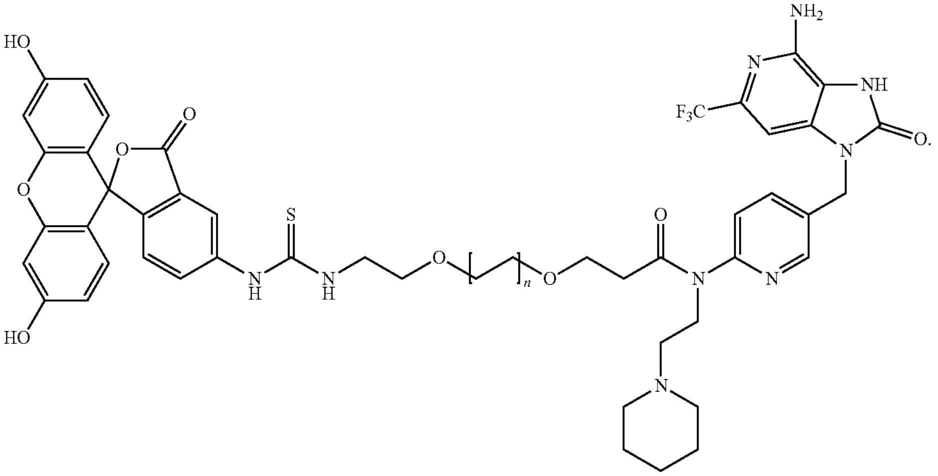
n = 0-12
8. The system according to claim 1, wherein the targeting ligand and the targeting ligand binding molecule are tacrolimus (FK506) and FK506-binding protein (FKBP), respectively, and the first component is a FK506-TLR7 agonist having the structure:
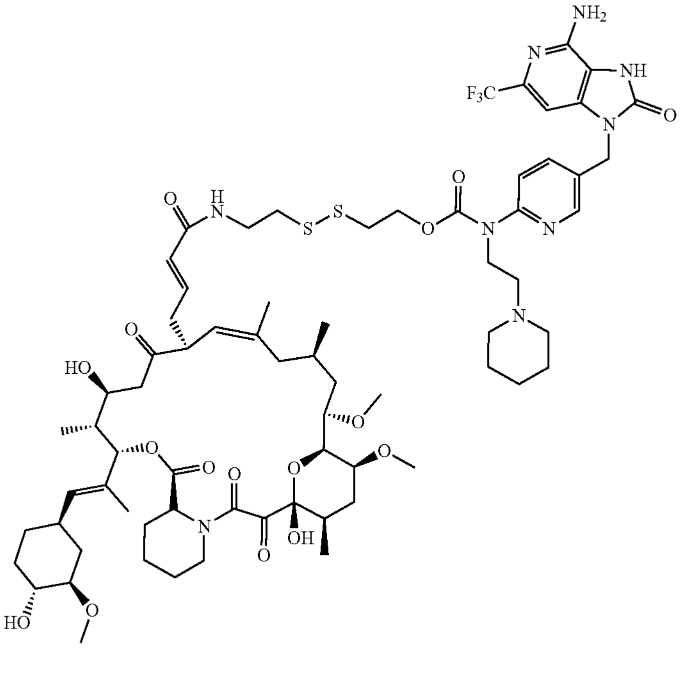
or -continued
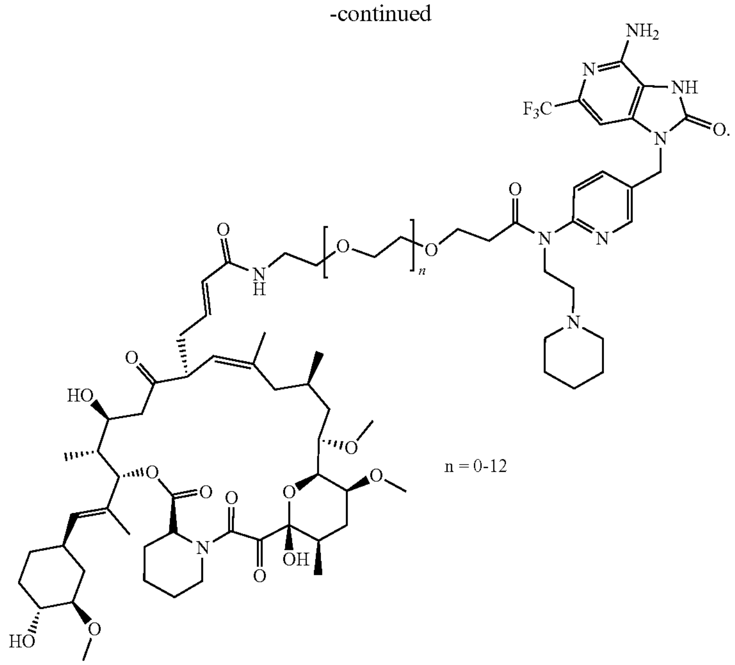
n = 0-12
9. The system according to claim 1, wherein the targeting ligand and the targeting ligand binding molecule are fluorescein isothiocyanate (FITC) and an anti-FITC scFv, respectively, and wherein the first component is one of the following:
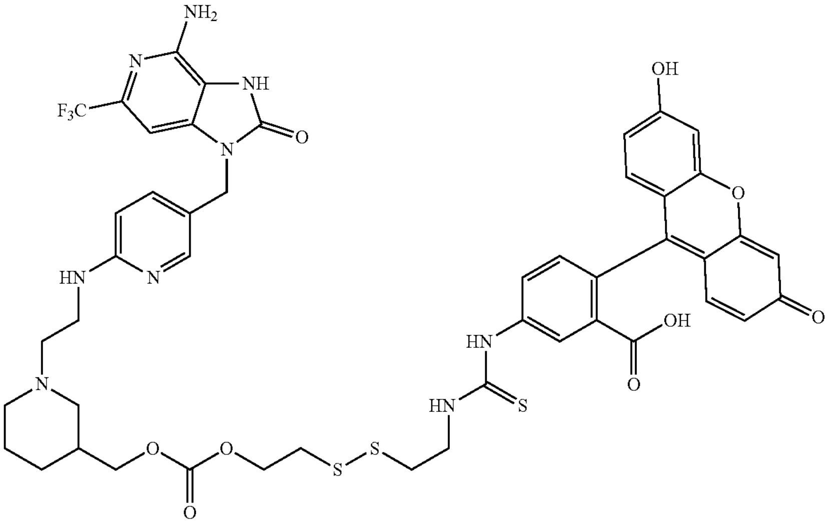
or
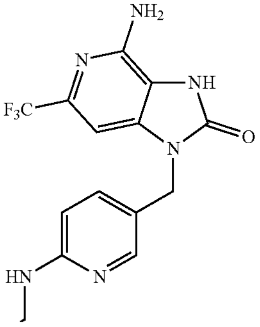

-continued

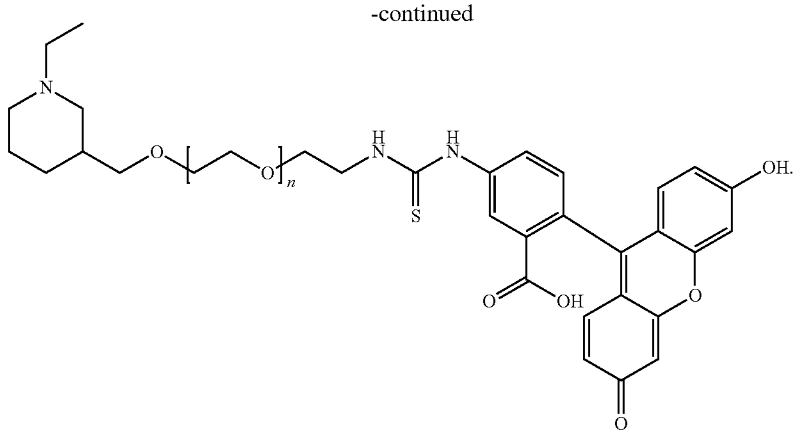

n = 0-16

10. The system according to claim 1, wherein the first component comprises a spacer between the targeting ligand and the payload drug, wherein the spacer is selected from the group consisting of the following structures:

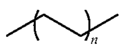

alkyl

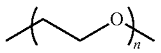

poly ethylene glycol (PEG)

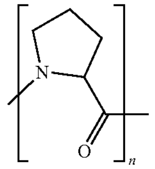

polyproline

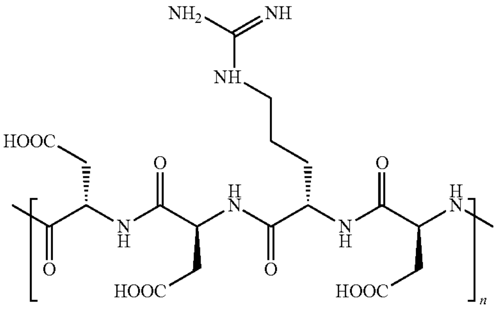

peptide

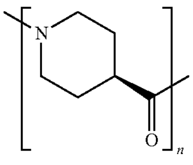

oligo-(4-piperidine carboxylic acid)

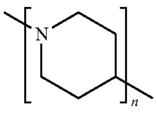

oligo piperidine

-continued

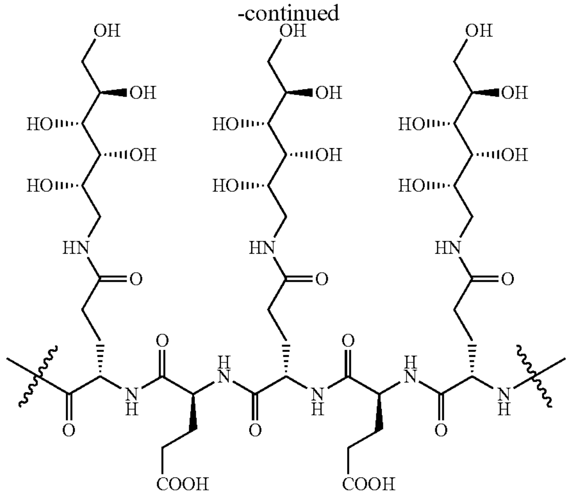

saccharo-peptide wherein n is 1-12.

11. A method to rejuvenate an exhausted CAR T cell, comprising:

a. providing to the exhausted CAR T cell a first component comprising a conjugate comprising, a targeting ligand covalently linked to a payload of drug through a releasable linker or a non-releasable linker;

b. providing said exhausted CAR T cell a second component comprising a fusion receptor, wherein the fusion receptor comprises a targeting ligand binding module linked to a membrane-anchoring module;

c. wherein the targeting ligand binding module of the second component binds to the targeting ligand in the first component to form a complex, d. the membrane-bound receptor module mediates internalization of the complex into the exhausted CAR T cell; and e. the payload drug re-activates the CAR T cell through an antigen-independent pathway;

wherein:

the payload drug is a Toll Like Receptor 7 (TLR7) agonist, the targeting ligand and the targeting ligand binding molecule are fluorescein isothiocyanate (FITC) and an anti-FITC antibody or fragment thereof, respectively, or tacrolimus (FK506) and FK506-binding protein (FKBP), respectively, and the membrane-anchoring module is a folate receptor.

12. The method according to claim 11, wherein the payload drug executes its function within the endosome of the exhausted CAR T cell, and the targeting ligand and the payload drug are linked by a non-releasable linker.

13. The method according to claim 11, wherein the payload drug executes its function as a free drug in the cytosol of the exhausted CAR T cell, and the targeting ligand and the payload drug are linked by a releasable linker.

14. The method according to claim 11, wherein the TLR7 agonist has the structure:

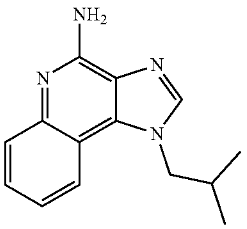

,

Imiquimod

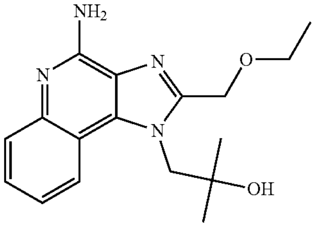

,

Resiquimod

-continued

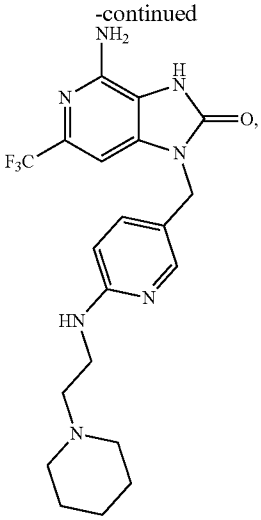

, or

TLR7 agonist

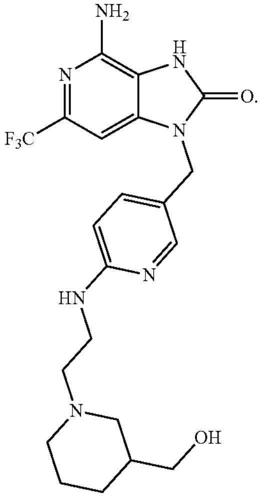

.

JTLR7

15. The method according to claim 11, wherein the first component is a targeting ligand and the targeting ligand binding molecule are fluorescein isothiocyanate (FITC) and an anti-FITC antibody or fragment thereof, respectively, and the first component is a fluorescein isothiocyanate-TLR7 agonist having the structure:

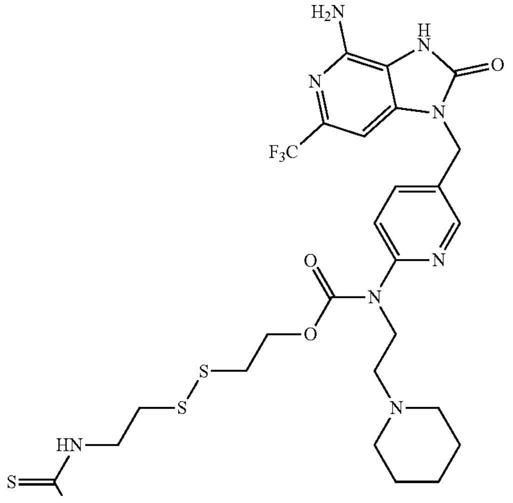
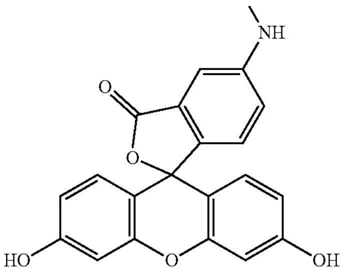
or
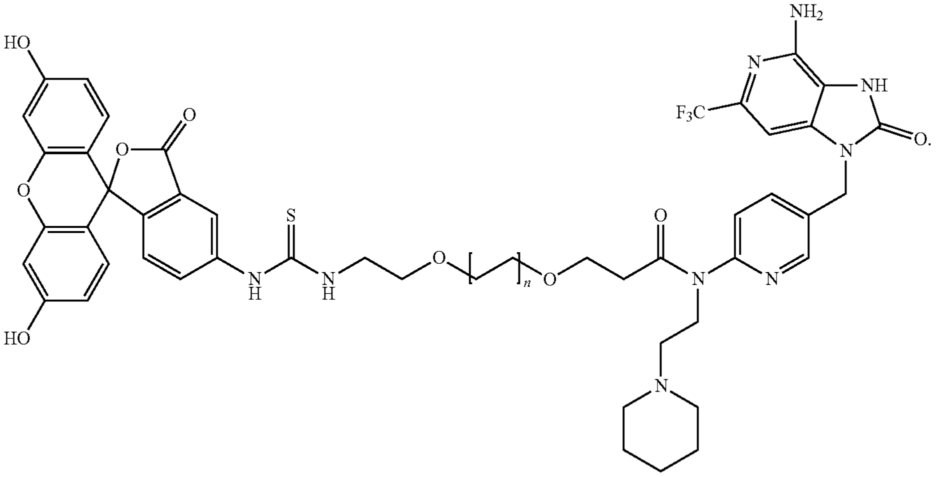
n = 0-12
16. The method according to claim 11, wherein the targeting ligand and the targeting ligand binding molecule are tacrolimus (FK506) and FK506-binding protein (FKBP), respectively, and the first component is a FK506-TLR7 agonist having the structure:

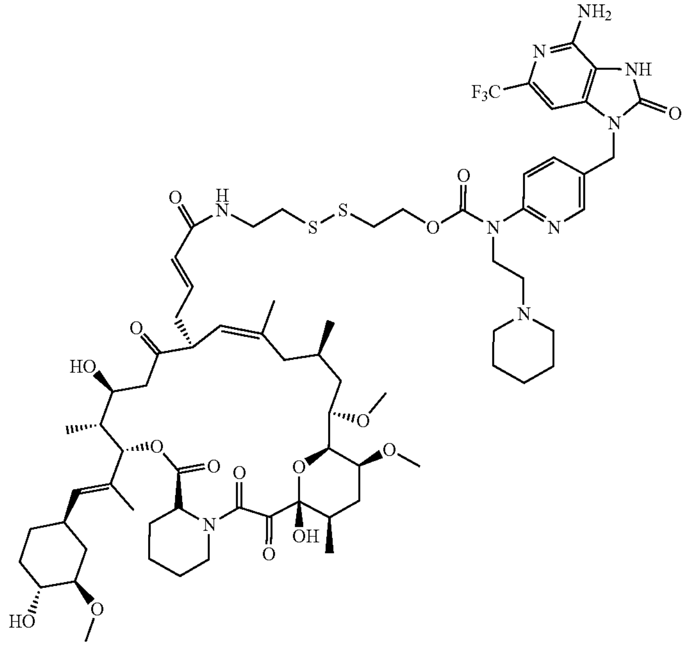
or
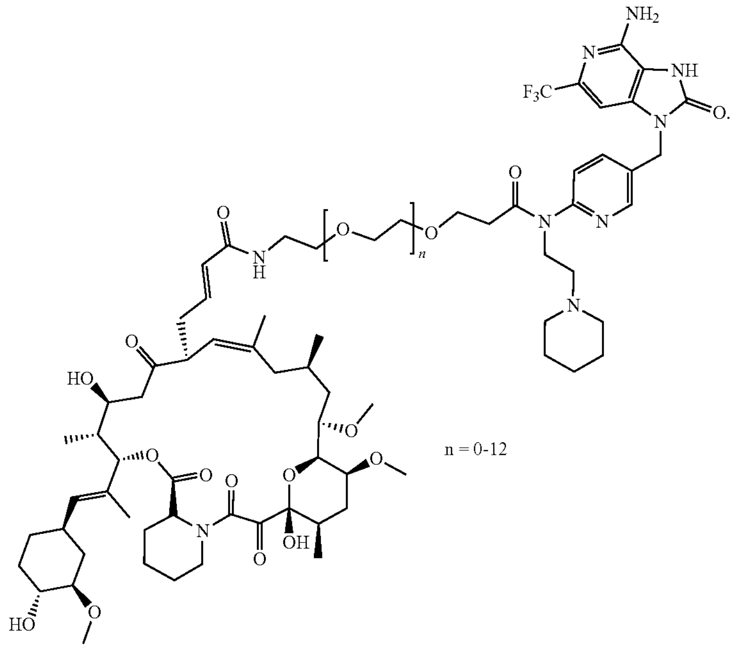
n = 0-12
17. The method according to claim 11, wherein the targeting ligand and the targeting ligand binding molecule are fluorescein isothiocyanate (FITC) and an anti-FITC scFv, respectively, and wherein the first component is one of the following;

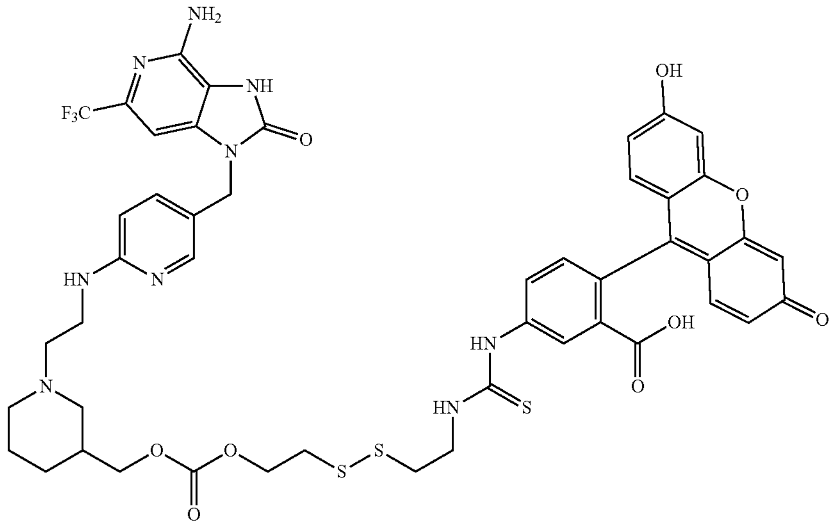
or
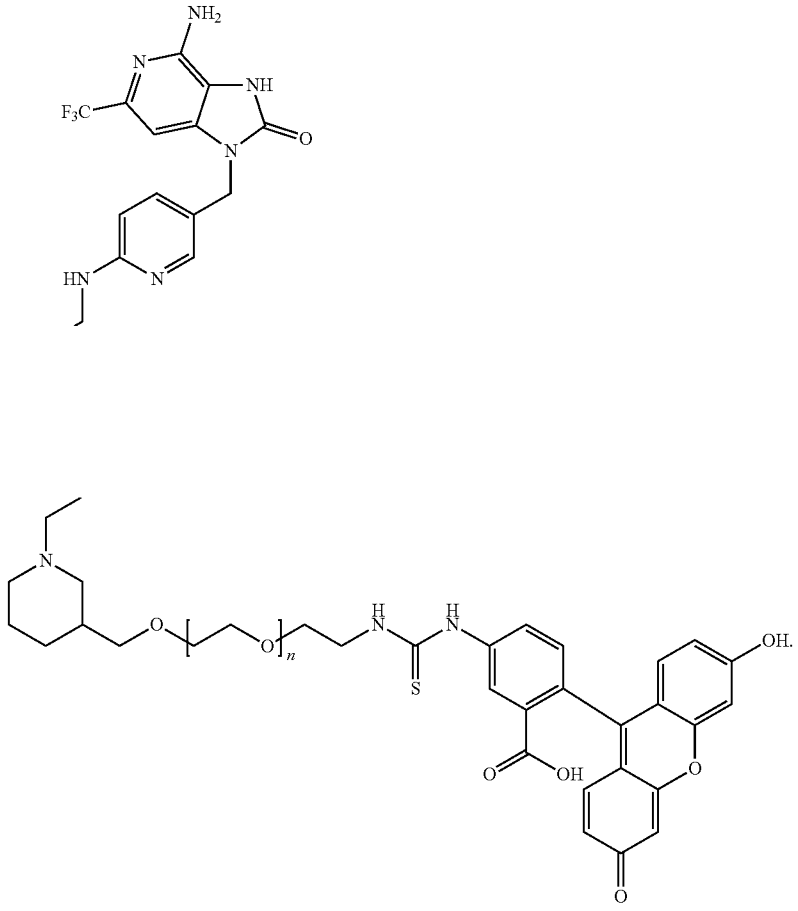
n = 0-16

18. The method according to claim 11, wherein the linker between the targeting ligand and the payload drug is selected from the group consisting of the following structures:
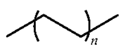
alkyl
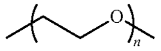
poly ethylene glycol (PEG)
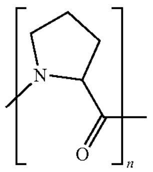
polyproline
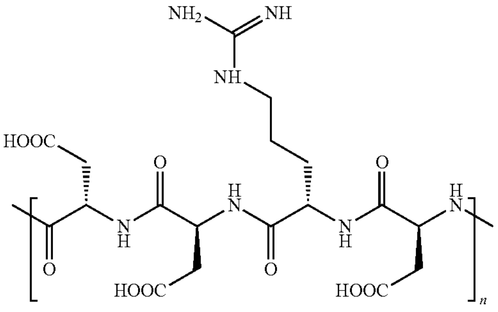
peptide
-continued
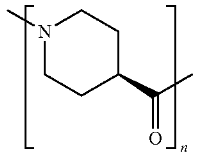
oligo-(4-piperidine carboxylic acid)
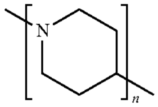
oligo piperidine
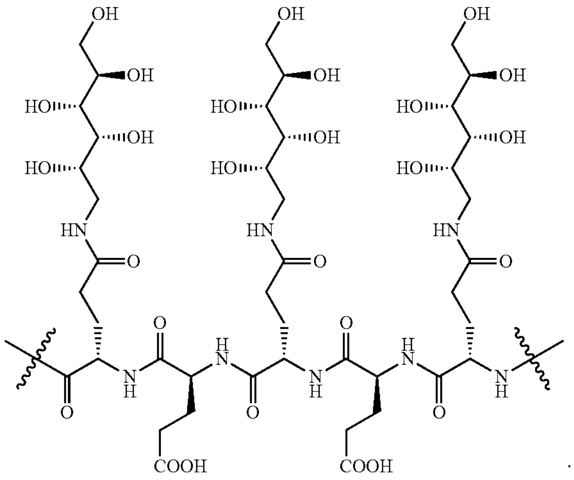
saccharo-peptide
wherein n is 1-12.
* * * * *